United States Patent
Olsson et al.

(10) Patent No.: US 12,116,634 B2
(45) Date of Patent: Oct. 15, 2024

(54) MARKER GENES FOR COLORECTAL CANCER CLASSIFICATION, METHOD FOR JUDGING LYMPH NODE METASTASIS FOR PROGNOSIS OF COLORECTAL CANCER AND KIT THEREFOR

(71) Applicant: HiloProbe AB, Umeå (SE)

(72) Inventors: Lina Olsson, Umeå (SE); Sten Hammarström, Stockholm (SE); Marie-Louise Hammarström, Umeå (SE); Gudrun Lindmark, Helsingborg (SE); Anne Israelsson, Umeå (SE)

(73) Assignee: HiloProbe AB, Umeå (SE)

( * ) Notice: Subject to any disclaimer, the term of this patent is extended or adjusted under 35 U.S.C. 154(b) by 425 days.

(21) Appl. No.: 17/210,768

(22) Filed: Mar. 24, 2021

(65) Prior Publication Data

US 2021/0246513 A1   Aug. 12, 2021

Related U.S. Application Data

(62) Division of application No. 16/093,013, filed as application No. PCT/SE2017/050368 on Apr. 12, 2017, now Pat. No. 10,988,811.

(30) Foreign Application Priority Data

Apr. 20, 2016   (SE) .................................... 1630095-6

(51) Int. Cl.
    *C12Q 1/6886*   (2018.01)
    *C12Q 1/68*   (2018.01)

(52) U.S. Cl.
    CPC ............ *C12Q 1/6886* (2013.01); *C12Q 1/68* (2013.01); *C12Q 2600/112* (2013.01); *C12Q 2600/118* (2013.01); *C12Q 2600/158* (2013.01)

(58) Field of Classification Search
    None
    See application file for complete search history.

(56) References Cited

U.S. PATENT DOCUMENTS

| | | |
|---|---|---|
| 6,773,882 B2 | 8/2004 | Hogan et al. |
| 2010/0009905 A1 | 1/2010 | Macina |
| 2011/0071049 A1 | 3/2011 | Heintz et al. |
| 2012/0015904 A1 | 1/2012 | Sharp et al. |
| 2013/0317043 A1 | 11/2013 | Wagner et al. |

FOREIGN PATENT DOCUMENTS

| | | |
|---|---|---|
| WO | 2009/057849 | 5/2009 |
| WO | 2011/018435 | 2/2011 |
| WO | 2013/033609 | 3/2013 |
| WO | 2013/033629 | 3/2013 |
| WO | 2013/052480 | 4/2013 |
| WO | 2015/120069 | 8/2015 |

OTHER PUBLICATIONS

Enard et al. (Science 2002 vol. 296 p. 340) (Year: 2002).*
International Search Report mailed in PCT/SE2017/050368 on Jul. 10, 2017.
Written Opinion of the International Searching Authority mailed in PCT/SE2017/050368 on Jul. 10, 2017.
Bao et al., "Periostin potently promotes metastatic growth of colon cancer by augmenting cell survival via the Akt/PKB pathway," Cancer Cell, vol. 5, No. 4, pp. 329-339 (2004).
Bas et al., "Utility of the Housekeeping Genes 18S rRNA, b-Actin and Glyceraldehyde-3-Phosphate-Dehydrogenase for Normalization in Real-Time Quantitative Reverse Transcriptase-Polymerase Chain Reaction Analysis of Gene Expression in Human T Lymphocytes" Scand. J. Immunol., vol. 59, Iss, 6, pp. 566-573 (2004).
Ben et al., "Circulating levels of periostin may help identify patients with more aggressive colorectal cancer," International Journal of Oncology, vol. 34, pp. 821-828 (2009).
Bockelman et al., "Risk of recurrence in patients with colon cancer stage II and III: A systematic review and meta-analysis of recent literature," Acta Oncol., vol. 54, Iss. 1, pp. 5-16 (2015).
Byrd et al., "Mucins and mucin binding proteins in colorectal cancer" Cancer Metastasis Review, vol. 23, pp. 77-99 (2004).
Chang G. J. et al. "Lymph Node Evaluation and Survival After Curative Resection of Colon Cancer: Systematic Review" J. Natl. Cancer Inst., vol. 99, Iss. 6, pp. 433-441 (2007).
Chomczynski et al., "Single-Step Method of RNA Isolation by Acid Guanidinium Thiocyanate-Phenol-Chloroform Extraction," Analytical Biochemistry, vol. 162, pp. 156-159 (1987).
Diffenbach (PCR methods and Applications (1993) vol. 3, pp. S30-S37) (Year: 1993).
Fahlgren et al., "Increased expression of antimicrobial peptides and lysozyme in colonic epithelial cells of patients with ulcerative colitis" Clin. Exp. Immunol., vol. 131, Iss. 1, pp. 90-101 (2003).
Iddings et al., "The Biologic Significance of Micrometastatic Disease and Sentinel Lymph Node Technology on Colorectal Cancer*" J. Surg. Oncol., vol. 96, Iss. 8, pp. 671-677 (2007).
Nicastri et al., "Is Occult Lymph Node Disease in Colorectal Cancer Patients Clinically Significant?" J. Mol. Diagn., vol. 9, p. 563-571 (2007).
Ohlsson L. et al., "Biomarker selection for detection of occult tumour cells in lymph nodes of colorectal cancer patients using real-time quantitative RT-PCR," Br. J. Cancer, vol. 95, pp. 218-225 (2006).
Ohlsson, "Biomarker mRNAs for staging and prognosis of colorectal cancer," Department of Clinical Microbiology, Immunology, Thesis, pp. 1-86, ISBN 978-91-7459-318-1 (2011).

(Continued)

*Primary Examiner* — Katherine D Salmon
(74) *Attorney, Agent, or Firm* — Grüneberg and Myers PLLC

(57) ABSTRACT

A group of molecular biomarkers having the genes SLC35D3, POSTN, KLK6 and MUC2 can be used in objective and quantitative methods for the classification, prediction of prognosis and for guiding treatment decisions of a subject with colorectal cancer. More specifically, a method for determining the metastatic potential and/or tumor aggressiveness of a colorectal cancer in a subject can include determining the gene expression levels of genes SLC35D3, POSTN, KLK6 and/or MUC2 in a regional lymph node, a primary intestinal tumor, blood, or feces sample obtained from the subject.

10 Claims, 5 Drawing Sheets

Figure 1:
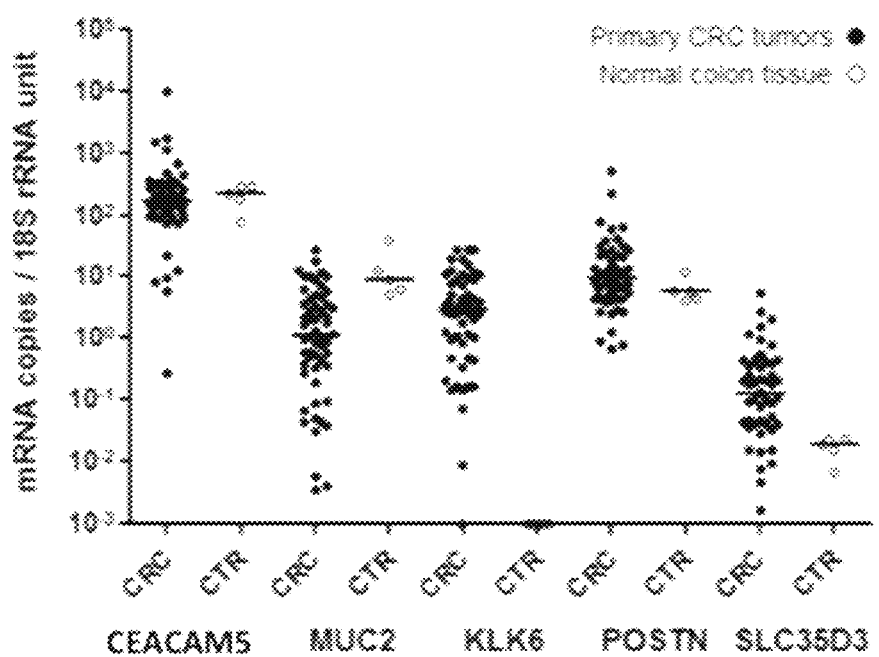

Specification includes a Sequence Listing.

(56) References Cited

OTHER PUBLICATIONS

Ohlsson L. et al., "Lymph node tissue kallikrein-related peptidase 6 mRNA: a progression marker for colorectal cancer," Br. J. Cancer, vol. 107, pp. 150-157 (2012).
Ohlsson L. et al., "Lymph node CEA and MUC2 mRNA as useful predictors of outcome in colorectal cancer" Int. J. Cancer, vol. 130, Iss. 8, pp. 1833-1843 (2012).
Parnaby C. N. et al., Br. J. Cancer, vol. 113, pp. 212-219 (2015).
Reiner et al., "Identifying differentially expressed genes using false discovery rate controlling procedures" Bioinformatics, vol. 19, pp. 368-375 (2003).
Roux et al (PCR Methods and Applications (1995) vol. 4, pp. s185-s194) (Year: 1995).
Tsal et al., "Factors affecting number of lymph nodes harvested and the impact of examining a minimum of 12 lymph nodes in stage I-III colorectal cancer patients: a retrospective single institution cohort study of 1167 consecutive patients," BMC Surg., vol. 16, p. 17 (2016).

* cited by examiner

MARKER GENES FOR COLORECTAL CANCER CLASSIFICATION, METHOD FOR JUDGING LYMPH NODE METASTASIS FOR PROGNOSIS OF COLORECTAL CANCER AND KIT THEREFOR

This application is a divisional application of U.S. application Ser. No. 16/093,013, filed on Oct. 11, 2018, which is the National Stage entry application under § 371 of International Application No. PCT/SE2017/050368, filed on Apr. 12, 2017, and claims priority to Swedish Patent Application No. 1630095-6, filed on Apr. 20, 2016. The content of each of these applications is hereby incorporated by reference in its entirety.

FIELD OF THE INVENTION

The present invention relates to the field of classification, prognostics and treatment of cancer, in particular colorectal cancer.

BACKGROUND

Colorectal cancer (CRC) is the second leading cause of mortality among cancer patients in the world and the third most diagnosed form of cancer globally. It represents a huge burden on healthcare systems. The most important prognostic characteristic of CRC is presence or absence of lymph node metastasis (Chang G. J. et al. J. Natl. Cancer Inst., vol. 99, p. 433-441 (2007); Iddings D. and Bilchik A. J. Surg. Oncol., vol. 96, p. 671-677 (2007); Nicastri D. G. et al. J. Mol. Diagn., vol. 9, p. 563-571 (2007)). Relevant lymph nodes are accessible for investigation only when patients are resected for cure. Therefore, thorough determination of the lymph node status in the resected tumor specimen is crucial. Currently, approximately 50% of patients with tumor-cell-positive lymph nodes, i.e. stage III CRC (anyTN1-2M0) and about 25% with no detected tumor-cell positive lymph nodes, i.e. stage I (T1-2 NOMO) and stage II (T3-4NOMO) patients will recur (Böckelman C. et al. Acta Oncol., vol. 54, p. 5-16 (2015)). These results strongly suggest that tumor cells in lymph nodes may vary in aggressiveness, and that presence of tumor cells in the node in many cases is missed by the present standard method. Therefore it is of utmost importance to 1) accurately detect presence of tumor cells in lymph nodes and 2) determine their metastatic potential i.e. their aggressiveness. By improving determination of lymph node status, N-staging, and introducing the aggressiveness parameter for the spread tumor cells, improved staging will be achieved thereby avoiding undertreatment of stage I and II patients and overtreatment of stage III patients. Moreover, if patients with tumor cells in their lymph nodes can be classified into subgroups according to differences in risk of recurrence and cancer death this information may be used not only for treatment with the current arsenal of drugs but also in the development of new drugs, new treatment schedules as well as for follow-up schedules adjusted to the risk of recurrence, etc.

In clinical practice, presence or absence of lymph node metastasis is currently determined by histopathological examination of hematoxylin & eosin (H&E) stained tissue sections of resected regional lymph nodes. Present guidelines require that at least 12 lymph nodes should be examined (Tsai H. L. et al. BMC Surg., vol. 16, p. 17 (2016)) In the TNM classification, N1 signifies that 1 to 3 examined nodes were positive for presence of tumor cells and N2 that 4 to 6 nodes were positive. N2 patients have poorer prognosis than N1 patients. Moreover, the lymph node ratio, i.e., number of positive lymph nodes over total number of examined lymph nodes, is an important prognostic factor—the higher ratio the worse prognosis (Parnaby C. N. et al, Br. J. Cancer, vol. 113, p. 212-219 (2015)). The main reasons why tumor cells are missed by the routine method are twofold:too small sample size and inadequate sensitivity. At best, only a few % of the volume of the lymph node is examined by H&E staining of tissue sections. An alternative method is to determine the mRNA level of one or several biomarkers that is expressed in all tumor cells of this type, and to extract RNA from the entire lymph node or, as for ethical reasons is the current option, half the node. It has been shown that real time quantitative reverse transcriptase-polymerase chain reaction (qRT-PCR) analysis with copy standard is a most useful method for mRNA analysis of biomarkers. It is highly sensitive, objective, quantitative, and amendable for automation. It was found that mRNA analysis of the biomarker carcinoembryonic antigen (CEA, CEACAM5) is very useful for detection of tumor cells originating from the large intestine. This biomarker allowed the identification of stage I and stage II patients with tumor cells in their lymph nodes that were not detected by the present gold standard, i.e. histopathology of H&E stained sections (Ohlsson L. et al. Br. J. Cancer, vol. 95, p. 218-225 (2006); Ohlsson L. et al. Int. J. Cancer, vol. 130, p. 1833-1843 (2012)). Some of these patients have succumbed from recurrent disease (Ohlsson L. et al. Br. J. Cancer, vol. 95, p. 218-225 (2006); Ohlsson L. et al. Int. J. Cancer, vol. 130, p. 1833-1843 (2012)). Thus, a more sophisticated stratification was obtained by using this marker compared to the gold standard only. The biomarker cytokeratin 20 (CK20) is also useful for this purpose, albeit somewhat less sensitive (Ohlsson L. et al. Br. J. Cancer, vol. 95, p. 218-225 (2006). Currently there is only one published biomarker for CRC that displays the properties of an aggression marker, namely kallikrein related peptidase 6 (KLK6) (Ohlsson L. et al. Br. J. Cancer, vol. 107, p. 150-157 (2012)). It is ectopically expressed in CRC tumor cells and appears to be expressed at increasing levels with increasing aggressiveness.

A generally accepted pathway for the development of distant metastases in CRC is that tumor cells leave the primary site in colon or rectum via lymphatic vessels, first settle in a regional lymph node, and thereafter, spread to distant sites like the liver. It is the distant metastasis that eventually kills the patient. Evidence for this pathway is the fact that presence or absence of tumor cells in a regional lymph node is the best prognostic marker for CRC death or survival.

The present invention concerns: 1) the identification of two new aggression biomarkers for CRC; one expressed in the CRC tumor cells themselves and the other in supporting cells in the microenvironment of the lymph node. 2) A method for determination of lymph node status, which accurately detects presence or absence of tumor cells in the lymph nodes, and in addition provides information on the aggressiveness of these cells. In the proposed method, quantitative mRNA levels of the 2 new biomarkers and 3 previously described biomarkers are determined. If applied for CRC lymph node analysis, it will accurately determine lymph node involvement and allow classification of CRC patients into different risk groups with respect to risk for recurrence and cancer death after the primary treatment, i.e. surgical resection of the tumor. This goal has hitherto not been possible to achieve.

OBJECT OF THE INVENTION

It is an object of the present invention to provide a group of molecular biomarkers, which are useful for classification, for prediction of prognosis and for guiding treatment decisions of a subject with colorectal cancer.

It is another object of the present invention to provide objective and quantitative methods for classifying colorectal cancer in a subject, as well as for using the classification for predicting prognosis of the subject and for making a treatment decisions for the subject.

DESCRIPTION OF THE INVENTION

The present inventors have identified the expression levels of the genes solute carrier family 35 member D3 (SLC35D3) (GenBank NM_001008783) and periostin, osteoblast specific factor (POSTN) (GenBank NM_006475) as molecular biomarkers that can be used for determining the metastatic potential and/or tumor aggressiveness of a colorectal cancer in a subject.

Expression levels of the genes SLC35D3 and POSTN can preferable be used together with the expression levels of the gene kallikrein related peptidase 6 (KLK6) (GenBank NM_002774), and even more preferably also together with the expression level of the gen mucin 2, oligomeric mucus/gel-forming (MUC2) (GenBank NM_002457) for determining the metastatic potential and/or tumor aggressiveness.

The method can be applied to determine gene expression levels in regional lymph node samples obtained from the subject, or in primary intestinal tumor, blood, and/or feces samples obtained from the subject.

The expression levels of these genes can be related to the expression level of the gene carcinoembryonic antigen related cell adhesion molecule 5 (CEACAM5) (GenBank NM_004363), which is a known tumor marker, and/or related to the level of 18S rRNA.

Accordingly, one aspect of the present invention provides methods for determining the metastatic potential and/or tumor aggressiveness of a colorectal cancer in a subject, comprising the steps:
a) determining the gene expression levels of genes SLC35D3, and POSTN in a regional lymph node sample obtained from the subject; and
b) comparing the gene expression levels determined in step a) with reference
gene expression levels of the same genes in a reference patient population; wherein higher expression levels of the genes SLC35D3 and POSTN compared to the reference are associated with an increased metastatic potential and/or tumor aggressiveness.

Preferably the method can further comprise determining the gene expression level of the gene KLK6 in said sample.

Accordingly, in one embodiment the first aspect of the present invention provides methods for determining the metastatic potential and/or tumor aggressiveness of a colorectal cancer in a subject, comprising the steps:
a) determining the gene expression levels of genes SLC35D3, POSTN and KLK6 in a regional lymph node sample obtained from the subject; and
b) comparing the gene expression levels determined in step a) with reference gene expression levels of the same genes in a reference patient population;
wherein higher expression levels of the genes SLC35D3, POSTN and KLK6 compared to the reference are associated with an increased metastatic potential and/or tumor aggressiveness.

Preferably the method can further comprise determining the gene expression level of the gene MUC2 in said sample.

Accordingly, in another embodiment the first aspect of the present invention provides methods for determining the metastatic potential and/or tumor aggressiveness of a colorectal cancer in a subject, comprising the steps:
a) determining the gene expression levels of genes SLC35D3, POSTN, KLK6 and MUC2 in a regional lymph node sample obtained from the subject; and
b) comparing the gene expression levels determined in step a) with reference gene expression levels of the same genes in a reference patient population;
wherein higher expression levels of the genes SLC35D3, POSTN, KLK6 and MUC2 compared to the reference are associated with an increased metastatic potential and/or tumor aggressiveness.

Preferably the method can further comprise the steps
c) determining the gene expression level of the gene CEACAM5 and the level of 18S rRNA in said sample;
d) based on the results obtained in steps a) and c) calculating the ratios SLC35D3/CEACAM5, KLK6/CEACAM5, POSTN/18S rRNA, and MUC2/CEACAM5;
e) giving the ratios obtained in step d) the values of (+1) or (0) depending on whether said ratio is larger than a cut-off value based on the same ratio in said reference patient population, and where ratios higher than the cut-off value obtain a value of (+1) and values lower than the cut-off level obtain a value of (0); and
f) calculating an index using the ratios obtained in step e) using the formula [A=SLC35D3/CEACAM5+KLK6/CEACAM5+POSTN/18S rRNA-MUC2/CEACAM5];
wherein the index (+3) is associated with very high metastatic potential and/or tumor aggressiveness, the index (+2) and (+1) with high metastatic potential and/or tumor aggressiveness, and the index (0) and (−1) with low metastatic potential and/or tumor aggressiveness.

Said cut-off values can be the ratios of the 7th decile of said reference patient population, the ratios of the $3^{rd}$ quartile of said reference patient population, or the ratios of the 8th decile of said reference patient population.

The methods can be performed in vitro and/or ex vivo.

The methods can further comprise the additional step of treating colorectal cancer in a subject in need thereof.

In another aspect the present invention provides methods of determining the metastatic potential and/or tumor aggressiveness of a colorectal cancer in a subject, comprising:
a) determining the gene expression levels of the genes SLC35D3, KLK6, MUC2 and CEACAM5 in a primary intestinal tumor, blood, or feces sample obtained from the subject;
b) based on the result obtained in step a) calculating the ratios SLC35D3/CEACAM5, KLK6/CEACAM5 and MUC2/CEACAM5; and
c) comparing the ratios determined in step b) with reference ratios calculated from expression levels of the same genes in a reference patient population;
wherein higher ratios SLC35D3/CEACAM5 and KLK6/CEACAM5 compared to reference are associated with an increased metastatic potential and/or tumor aggressiveness and a higher ratio MUC2/CEACAM5 compared to reference is associated with decreased metastatic potential and/or tumor aggressiveness.

The methods can be performed in vitro and/or ex vivo.

The methods can further comprise the additional step of treating colorectal cancer in a subject in need thereof.

According to the invention the gene expression levels can be determined by quantifying the amount of mRNA expressed from said genes.

The amount of mRNA can be determined by hybridization, sequencing or quantitative RT-PCR.

More specifically the amount of mRNA can be determined by use of a method selected from microarray and bead array technologies, transcriptome sequencing, real time quantitative RT-PCR, multiplex quantitative RT-PCR.

According to the methods the gene expression levels can be determined using RNA or DNA copy standard and/or the 18S rRNA level can be determined using 18S rRNA standard.

Another aspect of the present invention provides methods for determining the prognosis of a subject diagnosed with colorectal cancer. Said method can comprise determining the metastatic potential and/or tumor aggressiveness of a colorectal cancer in a subject using a method according to the present invention.

Said methods can comprise determining that the subject has a good prognosis if the metastatic potential and/or tumor aggressiveness is low, or
determining that the subject has a poor prognosis if the metastatic potential and/or tumor aggressiveness is high. Poor prognosis can be a decrease in the likelihood of survival compared to the good prognosis.

The methods can be performed in vitro and/or ex vivo.

The methods can further comprise the additional step of treating colorectal cancer in a subject in need thereof.

Another aspect of the present invention provides methods for determining the treatment for a subject diagnosed with colorectal cancer and having a tumor. Said method can comprise determining the metastatic potential and/or tumor aggressiveness of a colorectal cancer in a subject using a method according to the present invention and determining the treatment for said subject dependent on the metastatic potential and/or tumor aggressiveness determined.

The methods can be performed in vitro and/or ex vivo.

The methods can further comprise the additional step of treating colorectal cancer in a subject in need thereof.

The treatment can be to give postoperative treatment, e.g. chemotherapy, to a patient determined to have a high metastatic potential and/or tumor aggressiveness.

The treatment can be to abstain from postoperative treatment to a patient with a low metastatic potential and/or tumor aggressiveness.

Another aspect of the present invention provides a kit for determining metastatic potential and/or tumor aggressiveness of a subject diagnosed with colorectal cancer.

The kit can comprise nucleic acid primers and probes for determination of the gene expression levels, of one or more of the genes CEACAM5, KLK6, POSTN, SLC35D3, and MUC2 and optionally nucleic acid primers and probes for determination of the level of 18S rRNA.

In one embodiment the invention provides a kit for determining metastatic potential and/or tumor aggressiveness of a subject diagnosed with colorectal cancer, comprising nucleic acid primers and probes for determination of the gene expression levels of the genes SLC35D3 and POSTN.

In another embodiment the invention provides a kit for determining metastatic potential and/or tumor aggressiveness of a subject diagnosed with colorectal cancer, comprising nucleic acid primers and probes for determination of the gene expression levels of the genes SLC35D3, POSTN and KLK6.

In another embodiment the invention provides a kit for determining metastatic potential and/or tumor aggressiveness of a subject diagnosed with colorectal cancer, comprising nucleic acid primers and probes for determination of the gene expression levels of the genes SLC35D3, POSTN and MUC2.

In another embodiment the invention provides a kit for determining metastatic potential and/or tumor aggressiveness of a subject diagnosed with colorectal cancer, comprising nucleic acid primers and probes for determination of the gene expression levels of the genes SLC35D3, POSTN, KLK6 and MUC2.

In another embodiment the invention provides a kit for determining metastatic potential and/or tumor aggressiveness of a subject diagnosed with colorectal cancer, comprising nucleic acid primers and probes for determination of the gene expression levels of the genes SLC35D3, POSTN, KLK6, MUC2, and CEACAM5.

The nucleic acid primers and probes can be selected from those given in Table 1. More specifically the nucleic acid primers and probes can be selected from SEQ ID NO:1, 2, 3, 4, 5, 6, 7, 8, 9, 10, 11, 12, 13, 14, or 15.

The kit can further comprise mRNA, RNA and/or DNA copy standards.

Another aspect of the present invention provides methods for treatment of colorectal cancer. Said method can comprise determining the metastatic potential and/or tumor aggressiveness of a colorectal cancer in a subject using a method according to the present invention, and treating said subject dependent on the metastatic potential and/or tumor aggressiveness determined.

The treatment can be to give postoperative treatment, e.g. chemotherapy, to a patient determined to have a high metastatic potential and/or tumor aggressiveness.

The treatment can be to abstain from postoperative treatment to a patient with a low metastatic potential and/or tumor aggressiveness.

FIGURE LEGENDS

FIG. 1. Expression levels of CEACAM5, MUC2, KLK6, POSTN and SLC35D3 mRNA in primary CRC tumors (●) (n=56) and normal colon tissue (n=5) (○)

Figure 2:
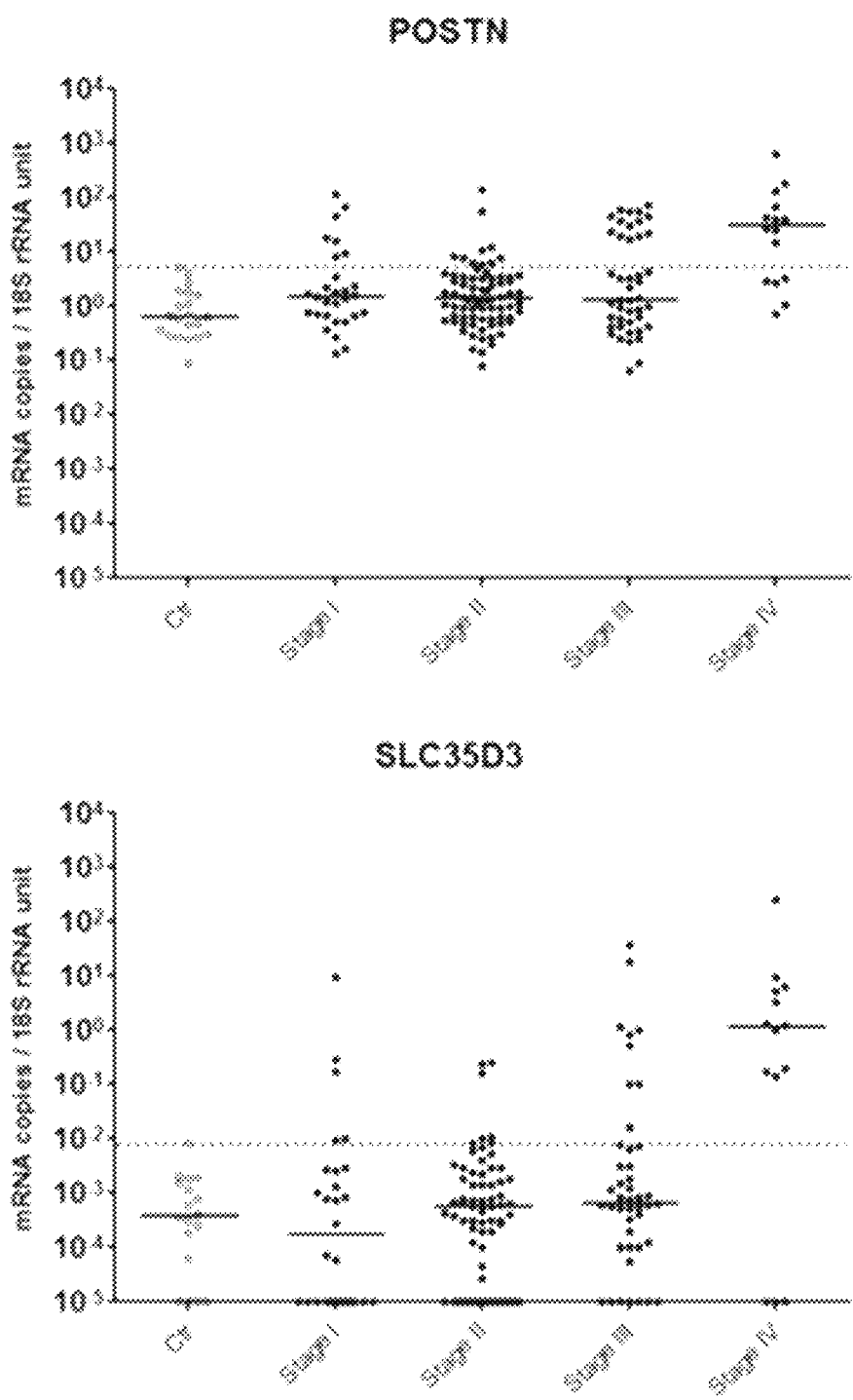

FIG. 2. (A) SLC35D3 and (B) POSTN mRNA expression levels in lymph nodes of patients with stage I to IV CRC and control patients (Ctr). Each of the 166 CRC patients and 23 control patients is represented by the lymph node with the highest mRNA value.

Figure 3:
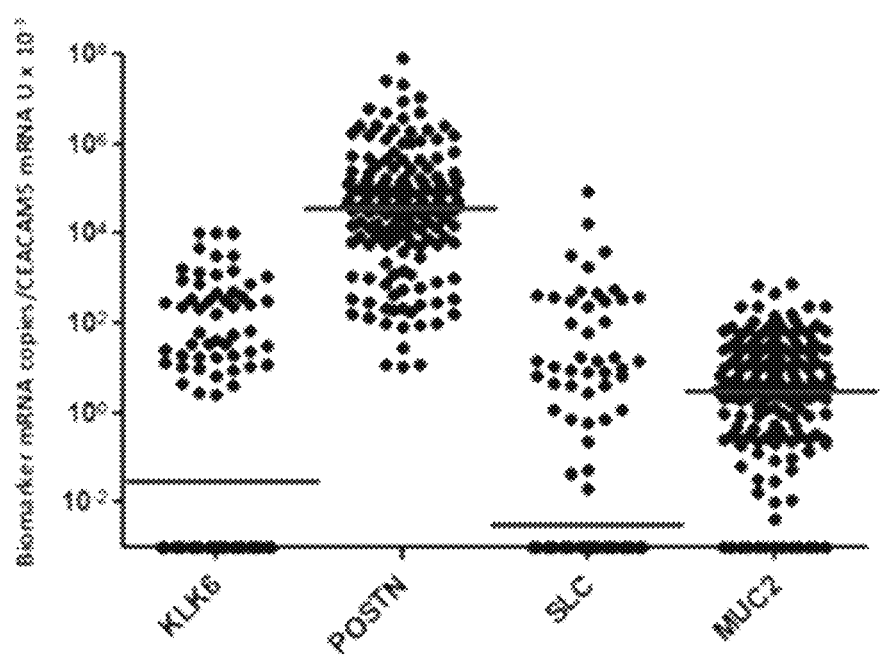

FIG. 3. Ratios of biomarker mRNA over CEACAM5 mRNA in lymph nodes from patients with stage I to IV CRC. Each of the 166 patients is represented by the lymph node with the highest mRNA value and indicated by a filled circle.

Figure 4:
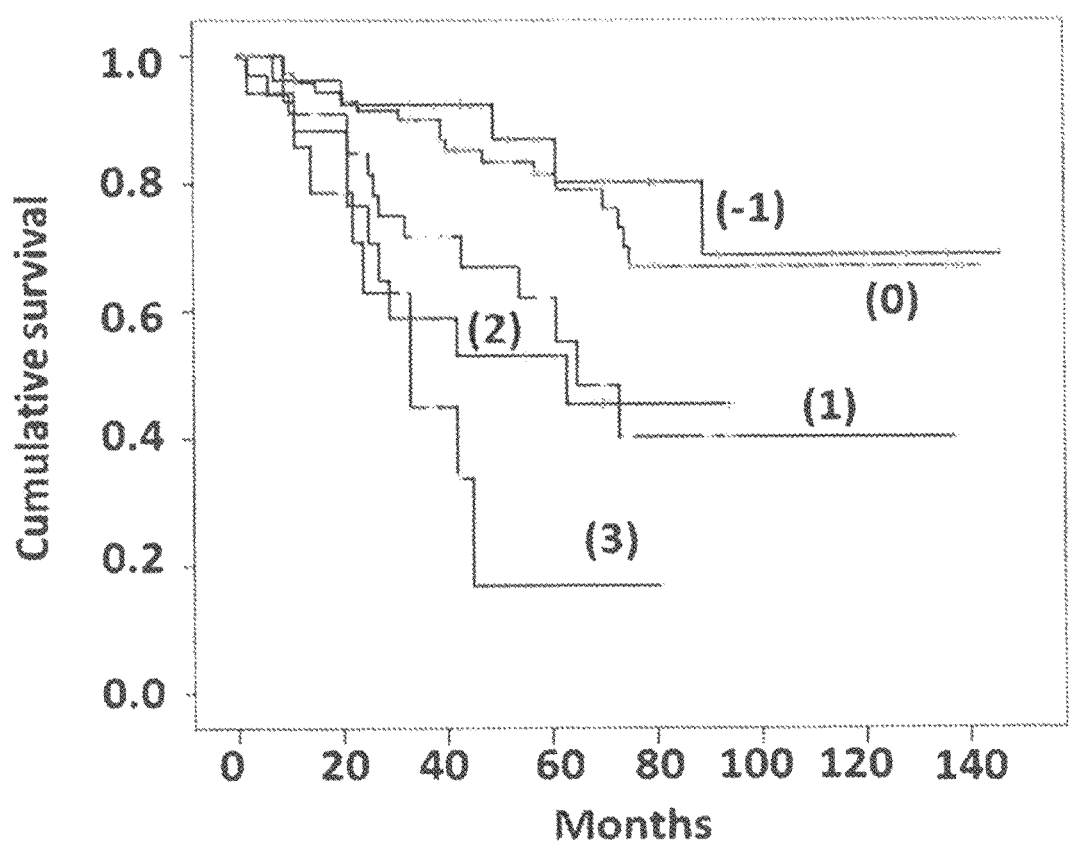

FIG. 4. Cumulative survival curves according to Kaplan-Meier for CRC patients (n=166). Patients are classified in groups (−1, 0, +1, +2 and +3) based on the mRNA value of the biomarkers SLC35D3, POSTN, KLK6, MUC2 and CEACAM5 and calculated according to formula: (Formula A=SLC35D3/CEACAM5+KLK6/CEACAM5+POSTN/ 18S rRNA-MUC2/CEACAM5). The $8^{th}$ decile of the mRNA values for each marker was used to classify the marker value as positive or negative, giving the former a value of (1) and the latter a value of (0). The lymph node with the highest CEACAM5 mRNA value was chosen to represent the patient. For further details see text.

Figure 5:
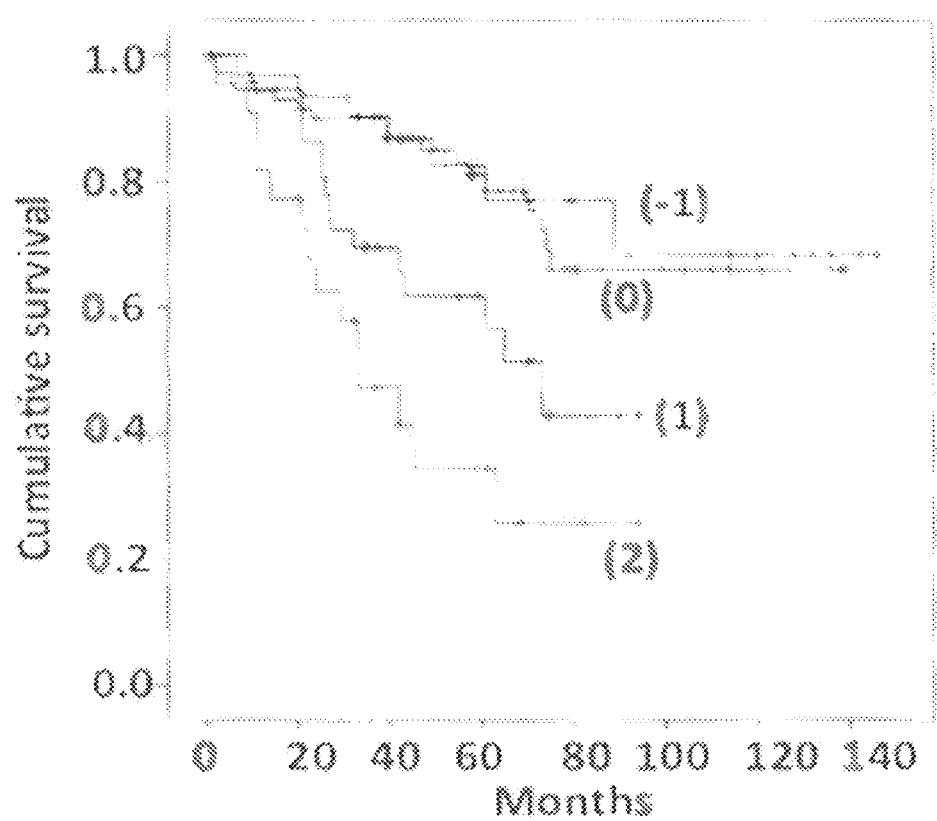

FIG. 5. Cumulative survival curves according to Kaplan-Meier for CRC patients (n=166). Patients are classified in groups (−1, 0, +1, and +2) based on the mRNA value of the biomarkers SLC35D3, POSTN, KLK6, MUC2 and CEACAM5 and calculated according to formula: (Formula E=SLC35D3/ CEACAM5+KLK6/CEACAM5−MUC2/CEACAM5). For further details see legend to FIG. 4 and text.

EXAMPLES

Identification of Genes and Gene Signatures that are Significantly Correlated to Risk of Cancer Death in Colorectal Cancer Subjects A gene that is of importance for tumor progression is most likely expressed both in the primary tumor tissue and in secondary tumors present in a regional lymph node draining the intestine. A microarray-search for progression markers was performed by analyzing RNA from 4 different H&E positive lymph nodes (i.e. tumor cell containing lymph nodes) of 4 patients with stage III CRC plus 3 primary tumors from 3 of these patients. RNA from 7 control patients (lymph nodes from 2 ulcerative colitis patients, 1 Crohns' colitis patient, 1 colon lipoma patient and 3 normal colon epithelial cells samples) were also analyzed. CRC samples were compared individually relative to all control samples as one group. The microarray data were filtered by setting statistical significance to $P<0.05$, fold change to $\geq 5$, and minimum intensity to 15. In this way a number of genes that were expressed in most of the CRC samples ($\geq 5/7$) with a fold change$\geq 5$ times were identified. Among these were SLC35D3, POSTN and KLK6.

Commercially available real-time qRT-PCR assays were used to verify the microarray results (TaqMan Gene Expression Assays) for POSTN, SLC35D3 and KLK6. In the latter case 3 assays for different splice forms. All three genes were expressed in a panel of primary CRC tumors samples (n=8) while SLC35D3 and KLK6 but not POSTN were expressed in all CRC cell lines (n=5).

CRC tumors, normal colon tissue and purified colon epithelial cells, CRC cell lines, peripheral blood mononuclear cells (PBMCs), different immune cell lines and a fibroblast cell line were analyzed (Table 3). The individual values of 56 primary CRC tumors and 5 normal colon samples are shown in FIG. 1. For comparison the result for CEACAM5 and MUC2 is included (Ohlsson L. Thesis, ISBN 978-91-7459-318-1 (2011)).

It is apparent that all five biomarker mRNAs are expressed in primary CRC tumors, although at highly different copy number levels normalized to the 18S rRNA content in the sample, from a median of 164 for CEACAM5 to 0.17 for SLC35D3 reflecting the abundance of the protein molecule that the particular mRNA is coding for.

Secondly, that the CRC cell lines express all marker mRNAs except POSTN, which instead is expressed at high levels in the fibroblast cell line.

Thirdly, that none of the markers is expressed to a significant degree in immune cell lines.

Fourthly, that CEACAM5 is expressed at similar levels in primary CRC tumors and normal colon epithelial cells. Based on the latter finding and previous knowledge (Ohlsson L. et al. Br. J. Cancer, vol. 95, p. 218-225 (2006)), CEACAM5 was considered to be the preferable marker for cells originating from the large intestine. Moreover, its high expression level makes it a very sensitive marker for detection of colorectal cancer cells in lymph nodes.

Fifthly, MUC2 measures to what extent a CRC tumor is mucinous or not, MUC2 being the dominant mucin in colon

TABLE 1

Primer and probe sequences used in qRT-PCR assays for SLC35D3, POSTN, KLK6, MUC2, CEACAM5, and 18S rRNA

| Gene | 3' primer sequence (reverse) | 5' primer sequence (forward) | Probe sequence |
|---|---|---|---|
| SLC35D3 | AGC ACT CCC GTG ACG TAC C (SEQ ID NO: 1) | TCA TCA CCA CCT GCG GC (SEQ ID NO: 2) | CCT GGC AGG AGC CGG CGA (SEQ ID NO: 3) |
| POSTN | CCC TTG CTT ACT CCC TTT CTC (SEQ ID NO: 4) | ACA GCT CAG AGT CTT CGT ATA TCG (SEQ ID NO: 5) | ACA GCT GTC TGC ATT GA (SEQ ID NO: 6) |
| KLK6 | AAG GTT ATG CTT CCC CAG G (SEQ ID NO: 7) | CTT ATC CAT CCA CTG TGG GTC (SEQ ID NO: 8) | CAC TGC AAA AAA CCG AAT CTT CAG GTC (SEQ ID NO: 9) |
| MUC2 | TAG TGT CCA GCT CCA GCA TGA (SEQ ID NO: 10) | AAG AGC GAT GCC TAC ACC AAA (SEQ ID NO: 11) | TCC CGG TTC CAC ATG A (SEQ ID NO: 12) |
| CEACAM5 | TGT AGC TGT TGC AAA TGC TTT AAG (SEQ ID NO: 13) | CTG ATA TAG CAG CCC TGG TGT AGT (SEQ ID NO: 14) | AGG AAG ACT GAC AGT TGT (SEQ ID NO: 15) |
| 18S rRNA | CCG CTC CCA AGA TCC AA (SEQ ID NO: 16) | GTA ATT CCA GCT CCA ATA GCG TA (SEQ ID NO: 17) | CTG CAG TTA AAA AGC (SEQ ID NO: 18) |

Real-time qRT-PCR assays with RNA copy standards using the Taqman EZ RT-PCR technology as described (Fahlgren A. et al. Clin. Exp. Immunol., vol. 131, p. 90-101 (2003); Ohlsson L. Thesis, ISBN 978-91-7459-318-1 (2011)) were constructed. Primer and probe sequences for real-time qRT-PCR assays for SLC35D3, POSTN, KLK6, MUC2, and CEA, mRNA are shown in Table 1 and primers for construction of RNA copy standards in Table 2. Using these assays a panel of RNA samples including primary and rectum. Patients with mucinous tumors have a better prognosis than those with non-mucinous tumors (Byrd J. C. and Bresalier R. S. Cancer Metastasis Review, vol. 23, p. 77-99 (204); Ohlsson L. et al. Int. J. Cancer, vol. 130, p. 1833-1843 (2012)).

Finally, in contrast to CEACAM5 and MUC2, both KLK6 and SLC35D3 were expressed in CRC tumors and most CRC lines but not in normal colon epithelial cells, i.e. they are ectopically expressed in CRC tumors.

TABLE 2

Primer sequences used in RT-PCR for cloning of cDNA and construction of RNA copy standards for SLC35D3, POSTN, KLK6, MUC2, CEACAM5, and 18S rRNA

| Gene | 3' primer sequence (reverse) | 5' primer sequence (forward) |
|---|---|---|
| SLC35D3 | CAGCACTCCCGTGACGTAC (SEQ ID NO: 19) | CATCGGCGTCCTGGTTC (SEQ ID NO: 20) |
| POSTN | CCCTTGCTTACTCCCTTTCTC (SEQ ID NO: 4) | ACAGCTCAGAGTCTTCGTATATCG (SEQ ID NO: 5) |
| KLK6 | TGGATCACAGCCCGGA (SEQ ID NO: 21) | TACACCTCGGGCCACTTG (SEQ ID NO: 22) |
| MUC2 | TAGTGTCCAGCTCCAGCATGA (SEQ ID NO: 10) | CCGGGCTGCTCATTGAGA (SEQ ID NO: 23) |
| CEACAM5 | TGGCTAGGATGGTCTCGAT (SEQ ID NO: 24) | GGACCTATGCCTGTTTTGTCT (SEQ ID NO: 25) |
| 18S rRNA | CGCTCCCAAGATCCAACTAC (SEQ ID NO: 26) | GTAATTCCAGCTCCAATAGCGTA (SEQ ID NO: 17) |

TABLE 3

Expression levels of SLC35D3, POSTN, KLK6, MUC2 and CEACAM5 mRNAs in primary CRC tumor, normal colon, normal colon epithelial cells, CRC cell lines, immune cell lines, a fibroblast cell line, CRC liver metastases and normal liver.

| | | | mRNA copies/18S rRNA unit | | | | |
|---|---|---|---|---|---|---|---|
| SOURCE | n | | SLC35D3 | POSTN | KLK6 | MUC2 | CEACAM5 |
| Primary CRC tumors | 56 | | 0.1* (0.04-0.4) | 9.7 (4.6-22.2) | 2.9 (0.9-8.5) | 1.1 (0.3-4.2) | 175 (107-283) |
| CRC cell lines | 1** | LS174T | 0 | 0 | 79 | 4.3 | 328 |
| | 1 | HT29 | 0.02 | 0 | 256 | 0.01 | 32 |
| | 1 | T84 | 0.7 | 0 | 316 | 0.5 | 33 |
| | 1 | HCT8 | 0.07 | 0 | 32 | 0.02 | 32 |
| | 1 | CaCo2 | 0.09 | 0.0009 | 0.4 | 0.04 | 3 |
| Normal Colon Tissue | 5 | | 0.02 | 5.9 | 0 | 9 | 222* |
| Normal Colon ECs | 5 | | 0.0009 | 0.2 | 0 | 32 | 300 |
| PBMCs | 1 | | 0.06 | 0 | 0 | 0 | 0 |
| Activated PBMCs | 3 | | 0 | 0 | 0 | 0 | 0 |
| T cell line | 1 | Jurkat | 0 | 0.009 | 0 | 0 | 0 |
| B cell lines | 1 | B6 + KR4 | 0 | 0 | 0 | 0 | 0 |
| Plasma cell line | 1 | U266 | 0 | 0.005 | 0 | 0 | 0 |
| Monocyte cell line | 1 | U937 | 0 | 0 | 0 | 0 | 0.005 |
| Granulocyte cell line | 1 | HL60 | 0 | 0 | 0 | 0 | 0 |
| Pre-erythrocyte cell line | 1 | K562 | 0.09 | 0.001 | 0 | 0 | 0 |
| Fibroblast cell line | 1 | FSU | 0 | 5.5 | 0 | 0.004 | 0.0002 |
| Livermetastasis | 2 | | 0.07 | 22.6 | 2 | 0.003 | 78 |
| Normal liver | 2 | | 0 | 2.3 | 0 | 0.00004 | 0.01 |

*Median and interquartile range from the $25^{th}$ to the $75^{th}$ percentile.
**Cell lines and PBMCs, mean of 3 determinations. ECs, purified epithelial cells; PBMCs, peripheral blood mononuclear cells; 0, < 0.00001 mRNA copies/18S rRNA unit.

Application of Combined Biomarker mRNA Analysis for Predicting Probability of CRC-Death A clinical material of lymph nodes from 166 surgically treated patients with CRC representing all four TNM stages and with known CEACAM5 mRNA, KLK6 mRNA, MUC2 mRNA and 18S rRNA expression levels was analyzed for expression levels of SLC35D3 mRNA and POSTN mRNA. In total mRNA from more than 600 lymph nodes were analyzed. The mRNA values were normalized against 18S rRNA and expressed as mRNA copies/18S rRNA unit. Previous studies by our group have demonstrated that 18S rRNA is an excellent RNA species for normalization (Bas A. et al, Scand. J. Immunol., vol. 59, p. 566-573 (2004); Ohlsson L. et al. Int. J. Cancer, vol. 130, p. 1833-1843 (2012)). The node with the highest mRNA expression level was used to represent the patient in further analysis. This is in analogy with the present clinical practice that H&E positive nodes are considered informative, while H&E negative nodes are considered non-informative except in the case when all nodes are negative. FIG. 2 shows the result. The figure also shows the mRNA values for lymph nodes from non-CRC control patients and the dashed line indicates the highest value of this control group. Lymph nodes from stage III and IV patients displayed a larger fraction of nodes with mRNA values above the cut-off level than nodes from stage I or II patients [SLC35D3: stage I=18%, stage II=9%, stage III=25%, and stage IV=79%; POSTN: stage I=25%, stage II=13%, stage III=32%, and stage IV=69%].

The results from analysis of SLC35D3- and POSTN mRNA expression levels were used in combination with the known expression levels for CEACAM5-, KLK6- and MUC2 mRNA in the same nodes of the CRC patients (Ohlsson L. et al. Br. J. Cancer, vol. 95, p. 218-225 (2006); Ohlsson L. Thesis, ISBN 978-91-7459-318-1 (2011); Ohlsson L. et al. Br. J. Cancer, vol. 107, p. 150-157 (2012)). Cut-off levels were determined for the 5 biomarkers as follows: The patients were ranked according to the biomarker expression level in the highest lymph node and then divided into five groups of equal number of patients. The groups were compared with respect to disease-free survival using Cox regression analysis. From this analysis, the cut-off level was defined as the mRNA expression level at the $8^{th}$ decile because, for all five markers, the groups below the $8^{th}$ decile did not differ significantly in disease-free survival. Patients who died from causes other than CRC were considered as disease-free. Patients were divided into two groups, mRNA expression value above and mRNA expression value below the cut-off and for each group the mean survival time after surgery was calculated by cumulative survival analysis according to Kaplan-Meier and risk for recurrence of CRC estimated according to univariate Cox regression analysis. The result for the five biomarkers is shown in Table 4. As can be seen, mRNA values above the cut-off levels for all of them were correlated with poorer prognosis with highly significant P-values.

were then referred to one of two groups>0.00001 or <0.00001 (FIG. 3). The former group was assigned a value of 1 and the latter a value of 0. For MUC2/CEACAM5 the division was achieved at a ratio of 3.0 assigning nodes with values above 3.0 a value of 1 and below a value of 0 (FIG. 3). For POSTN the POSTN/18S rRNA ratio and the clinical cut-off (8.0 copies/18S rRNA unit; FIG. 2) were used to achieve the two groups, assigning values of 1 above the clinical cut-off and 0 for below. A formula, (Formula A: SLC35D3/CEACAM5+KLK6/CEACAM5+POSTN/18S rRNA −MUC2/CEACAM5) was used to classify each patient into one of five groups (formula result: −1, 0, +1, +2, +3) and cumulative survival analysis according to Kaplan-Meier was performed on these groups. The result is shown in FIG. 4. Five different curves are obtained. Group (−1) and (0) show good 3 and 5 years survival, group (+1) and (+2), relatively poor survival and group (+3) very poor survival (Table 5). The risk ratios calculated according to univariate Cox regression analysis, for groups (0), (+1), (+2) and (+3) in comparison to group (−1), is shown in Table 6.

In other embodiments of the invention the biomarker mRNA measurements were calculated in the same way as in Formula A except that in these formulas, e.g. Formula B to Formula E, one of the terms was systematically excluded. FIG. 5 shows the cumulative survival according to Kaplan-Meier calculated according to formula E. Table 5 summarizes 3 and 5 years survival for biomarker mRNA measurements as determined by the 5 formulas (Formula A to Formula E) and Table 6 summarizes the hazards ratios for biomarker mRNA measurements as determined by Formula A, B and C. Although useful information with respect to survival after surgery is generated by biomarker data treated according to formula B to formula E it is clear that treating the biomarker mRNA data according to Formula A is the most informative demonstrating that all of these biomarkers contribute to the result.

TABLE 4

Comparative analysis of average survival time and risk for recurrence of disease of CRC patients with biomarker (+) or biomarker (−) lymph nodes

| Biomarker | mRNA (copies/18S rRNA unit) Level | Survival time after surgery (months) | | | Risk for recurrence of CRC | |
|---|---|---|---|---|---|---|
| | | Average | Difference vs marker (−) | P-Value | Hazard ratio | P-value |
| SLC35D3 (−) | <0.0059* | 103** | | | | |
| SLC35D3 (+) | >0.0059 | 54 | 49 | 0.002 | 2.48*** | 0.002 |
| POSTN (−) | <11.05 | 107 | | | | |
| POSTN (+) | >11.05 | 76 | 31 | 0.001 | 2.52 | 0.002 |
| KLK6 (−) | <0.0831 | 110 | | | | |
| KLK6 (+) | >0.0831 | 46 | 64 | <0.0001 | 4.01 | <0.0001 |
| MUC2 (−) | <0.0045 | 108 | | | | |
| MUC2 (+) | >0.0045 | 64 | 44 | 0.001 | 2.53 | 0.001 |
| CEA (−) | <4.2 | 112 | | | | |
| CEA (+) | >4.2 | 44 | 68 | <0.0001 | 4.67 | <0.0001 |

*The cut-off level is the 8th decile of the patient population.
**Mean survival time after surgery as calculated by cumulative survival analysis according to Kaplan-Meier.
***Risk ratio as calculated according to univariate Cox regression analysis.

Determining the levels for all five biomarkers and combining the different measurements achieves further differentiation of the patient groups with respect to survival. In one embodiment of the invention the combined information derived from the biomarker analysis to predict survival after surgery is used as follows: For each highest lymph node the values for the biomarkers, SLC35D3, KLK6 and MUC2 is first divided by their corresponding CEACAM5 value. For SLC35D3/CEACAM5 and KLK6/CEACAM5 the ratios

TABLE 5

Percentage of CRC patients that have died from cancer 3 and 5 years after surgery as determined by cumulative survival according to Kaplan-Meier. Comparison between patients classified into groups according to formula A, B, C, D and E.

| | Formula | | | | | | | | | |
|---|---|---|---|---|---|---|---|---|---|---|
| | A | B | C | D | E | A | B | C | D | E |
| Group | | | 3 years | | | | | 5 years | | |
| −1 | 7 | 10 | 5 | — | 10 | 14 | 15 | 12 | — | 18 |
| 0 | 10 | 13 | 14 | 9 | 10 | 20 | 26 | 21 | 15 | 19 |
| +1 | 28 | 31 | 34 | 20 | 29 | 37 | 38 | 42 | 32 | 38 |
| +2 | 42 | 57 | 41 | 51 | 42 | 47 | 84 | 80 | 58 | 65 |
| +3 | 56 | — | — | 34 | — | 84 | — | — | 60 | — |

Formula A: [SLC35D3/CEACAM5+POSTN/18SrRNA+KLK6/CEACAM5-MUC2/CEACAM5] giving the groups −1, 0, +1, +2, +3
Formula B: [SLC35D3/CEACAM5+POSTN/18S rRNA-MUC2/CEACAM5] giving the groups −1, 0, +1, +2
Formula C: [KLK6/CEACAM5+POSTN/18S rRNA-MUC2/CEACAM5] giving the groups −1, 0, +1, +2
Formula D: [SLC35D3/CEACAM5+KLK6/CEACAM5 +POSTN/18S rRNA] giving the group 0, +1, +2, +3
Formula E: [SLC35D3/CEACAM5+KLK6/CEACAM5-MUC2/CEACAM5] giving the groups −1, 0, +1, +2,

TABLE 6

Risk for recurrence of CRC after surgery as calculated according to univariate Cox regression analysis. Comparison between patients classified into groups according to formula A, B and C.

| | Formula A | | Formula B | | Formula C | |
|---|---|---|---|---|---|---|
| Group | Hazards ratio | P-value | Hazards ratio | P-value | Hazards ratio | P-value |
| −1 | * | | * | | * | |
| 0 | 1.33 | ns | 0.49 | Ns | 0.41 | ns |
| +1 | 3.15 | 0.028 | 2.34 | Ns | 3.3 | 0.008 |
| +2 | 3.64 | 0.021 | 5.56 | 0.001 | 6.59 | <0.0001 |
| +3 | 6.98 | 0.001 | | | | |

Formula A: [SLC35D3/CEACAM5+POSTN/18S rRNA+KLK6/CEACAM5-MUC2/CEACAM5] giving the groups −1, 0, +1, +2, and +3
Formula B: [POSTN/18S rRNA+SLC/CEACAM5-MUC2/CEACAM5] giving the groups −1, 0, +1, +2
Formula C: [POSTN/18S rRNA+KLK6/CEACAM5-MUC2/CEACAM5] giving the groups −1, 0, +1 and +2.

A Kit for Determination of Biomarker mRNAs

The invention also includes a kit for analysis of biomarker mRNA and 18S rRNA and transformation of raw data to clinically useful information as illustrated by formulas Formula A to Formula E.

In one embodiment of the invention the particular forward and reverse primers as well as probe sequences given in Table 1 are used in real-time quantitative RT-PCR. Quantitation is achieved by using specific copy standards (RNA) and 3' primers for reverse transcription with biomarker mRNA values normalized to content of 18S rRNA and/or content of CEACAM5 mRNA in the sample. Normalized values are allocated to one of two groups, either (1=high risk for recurrence) and (0=low risk for recurrence) according to the biomarker level with cut-off levels determined from analysis of a clinical material of lymph nodes from surgically treated CRC patients. Using a specifically designed algorithm the (1) and (0) values for each biomarker is transformed to an estimate of relative risk of cancer death, with a range −1, 0, +1, +2, +3, where −1 stands for the lowest risk and +3 for the highest risk, based on the formula: SLC35D3/CEACAM5+KLK6/CEACAM5+POSTN/18S rRNA −MUC2/CEACAM5.

In the embodiments of the invention as exemplified in FIGS. 4 and 5 and Tables 5 and 6 preferably only the information from the lymph node with the highest biomarker mRNA is of value. However, a number of patients have more than one lymph node harboring tumor cells. The methods according to the invention can also be used in this case, i.e. for differentiation between N1 and N2 stage patients, adding prognostic value.

EXPERIMENTAL METHODS

General Methods

Bioinformatics Analysis—Results from microarray gene expression analysis were analyzed by using Illumina Beadstudio software (version 3.3) for direct hybridization assays. Intensity data were normalized by Beadstudios cubic spline algorithm with subtracted background. Significant difference in expression was calculated using Beadstudio software Error Model Illumina Custom with multiple testing corrections using Benjamini and Hochberg False Discovery Rate (Reiner A. et al. Bioinformatics, vol. 19, p. 368-375 (2003)). Difference in gene expression was calculated as fold change, dividing the signal in the CRC samples of interest over average signal of controls.

Cell lines and peripheral blood mononuclear cells—The following established human cell lines were utilized: LS174T, HT29, T84, HCT8 and CaCo2 (all colon carcinomas), Jurkat and Molt-4 (T-cell lymphomas), B6 and KR4 (EBV-transformed B cell lines), U266 (plasmacytoma), U937 (monocyte-like cell line), K562 (erythroblastoid cell line), HL60 (granulocyte cell line), FSU (fibroblast cell line). Peripheral blood mononuclear cells (PBMCs) were isolated from peripheral blood of healthy adults by Ficoll-Isopaque gradient centrifugation. PBMCs were activated in vitro by incubation with the OKT3 monoclonal antibody (50 ng/ml) in HEPES-buffered RPMI 1640 supplemented with 0.4% human serum albumin. PBMCs from seven individuals were incubated with the stimulus in parallel cultures for 4, 7, 20, 48 and 72 hours, washed, pooled and RNA extracted.

Clinical characteristics of the CRC patients and Controls—Surgery for treatment of CRC was carried out in 166 patients [81 men, 85 women, median age 72, (range 42-90) years]. Thirteen of the tumors were located in rectum and 153 in the colon. Seven of the rectal cancer patients received 25 Gy of preoperative radiotherapy. A locally radical tumor resection was carried out in all patients. The tumor differentiation grade was poor, moderate and high in 11, 145 and 10 tumors, respectively. Routine hematoxylin and eosin (H&E) staining was performed on 2,351 lymph nodes, giving a median of 13 (range 1-51) nodes per patient. According to the TNM classification, 30 patients were in stage I (T1-2NOMO), 74 in stage II (T34NOMO), 46 in stage III (anyTN1-2M0) and 16 in stage IV (anyTanyNM1). Thirty-four patients (4 in stage II, 19 in stage III and 11 in stage IV) received chemotherapy after surgery. The median follow-up time was 75 (range 33-147) months and no patient was lost at follow-up.

Controls included 18 men and 5 women [median age 25 years, (range 10-61)] undergoing surgery for ulcerative colitis (n=18), Crohn's colitis (n=3), rectal prolapse (n=1), and colon lipoma (n=1).

Informed consent was obtained from the patients and in one case his parents. The Research Ethics Committee of the Medical Faculty, Umeå University, Sweden approved the study.

Primary and distant CRC tumor and normal colon tissue—One hundred and thirteen samples from 85 primary CRC tumors were analyzed for biomarker mRNA levels (22 samples from 16 stage I patients, 44 samples from 35 stage II patients, 41 samples from 25 stage II patients, and 8 samples from 8 stage IV patients). Primary tumor stage distribution (pT1-pT4) was 2, 14, 55 and 13 respectively. The differentiation grade was poor in 11 tumors, moderate in 71 tumors and high in 3 tumors. One to four samples, approximately 0.5×0.5×0.5 cm in size, were collected from primary tumor specimens immediately after resection, snap-frozen, and stored at −70° C. until RNA extraction. Six normal colon samples, retrieved from the proximal or distal resection margin and two distant liver metastasis samples were collected and treated in the same way as the primary CRC tumors.

Epithelial cells from colon tissue—Colonic epithelial cells (ECs) were isolated from the normal colon mucosa at the resection margins as described (Fahlgren A. et al. Clin. Exp. Immunol., vol. 131, p. 90-101 (2003)).

Lymph nodes—Lymph nodes were retrieved from the resected specimens and bisected with separate, sterile knives. One half of each node was fixed in 10% buffered formalin for routine H&E-staining. The other half was snap frozen in liquid nitrogen and stored at −70° C. until RNA extraction. From CRC patients, 503 lymph nodes (91, 253, 107 and 52 nodes from stage I-IV patients, respectively) were collected. A median of 2 (range 1-15) lymph nodes was obtained per patient.

From control patients, 108 lymph nodes (82, 9, 13 and 4 nodes from ulcerative colitis, Crohn's colitis, colon lipoma and rectal prolapse patients, respectively) were collected.

RNA isolation—Total RNA was extracted from lymph nodes, normal and tumor colon tissues, colon epithelial cells, PBMCs and cell lines using the acid guanidine phenol chloroform method (Chomczynski P and Sacchi N. Analyt. Biochem., vol. 162, p. 156-159 (1987)) by adding 0.5 ml of a solution containing 4 M guanidinium thiocyanate, 25 mM sodium citrate (pH 7.0), 0.5% sarcosyl and 0.1 M 2-mercaptoethanol per 25 mg tissue and up to $2.5 \times 10^6$ cells in the first homogenization step. Extracted RNA was dissolved in RNAse-free water containing the RNAse inhibitor RNAsin (1U/µl; Promega, Madison, WI). The RNA concentration was measured in a NanoDrop ND-1000 Spectrophotometer (NanoDrop Technologies) and for bead microarray analysis the integrity of the RNA was analyzed in a 2100 Bioanalyzer using an RNA nano assay (Agilent Technologies).

Preparation of RNA copy standards—Total RNA from a primary CRC tumor, two lymph nodes from two patients with CRC and the colon carcinoma cell lines LS174T and T84 were used as starting material for copy standard preparations. The primers used for RT-PCR are given in Table 2. The PCR products, which include the respective sequences amplified in quantitative RT-PCR, were cloned, sequenced and used as template for in vitro transcription with T7 polymerase/RiboProbe In Vitro Transcription Systems (Promega). Linearized DNA, 3-7 µg, was used in large-scale synthesis reactions carried out at 37° C. for 2-3 hr. The reaction products were then treated with 1 U/µg of RNase-free DNase (Promega) for 30-40 min at 37° C. followed by extraction with phenol:chloroform:isoamylalcohol (25:24:1) and chloroform:isoamylalcohol (24:1). RNA was precipitated with 2.5 volumes of 99.5% ethanol and 0.5 volumes of 7.5 M ammonium acetate at −70° C. for at least one hr. DNase treatment was repeated at least twice. Finally the copy standards were checked by RT-PCR and PCR to evaluate the content of DNA, which proved to be less than 0.2% for all of them. Concentration of the transcripts was calculated on the basis of the $OD_{260}$ value, the molecular weight of the transcript and Avogadro's number. The standards were finally diluted to $10^8$ copies/µl.

Real-time qRT-PCR—Real-time qRT-PCR assays with RNA copy standards were constructed for SLC35D3, POSTN, KLK6, CEACAM5, and MUC2 using the Tacman EZ RT-PCR technology (Applied Biosystems Foster City Ca). Primer and probe sequences are shown in Table 1. The RT-PCR profile was 49° C. for 2 min, 59° C. for 30 min, 94° C. for 5 min, followed by 45 cycles of 93° C. for 20 sec and 61° C. for 1 min. Serial dilutions of the respective RNA copy standard at concentrations from $10^3$ to $10^8$ copies/µl were included in each analysis. All qRT-PCR analyses were carried out in triplicates. Emission from released reporter dye was monitored by the ABI Prism 7900 Sequence Detection System (Perkin-Elmer, Wellesley, Ma). For normalization of mRNA levels, the concentration of 18S rRNA was determined in each sample by real-time qRT-PCR according to the manufacturer's protocol (Applied Biosystems) or by use of primers and probe given in Table 1 (SEQ ID NO: 16-18) and copy standard prepared by using the primers given in Table 2 (SEQ ID NO: 26,17). Results were expressed as mRNA copies per unit of 18S rRNA or as RNA copies per copy of 18S rRNA in both cases yielding directly comparable levels of biomarkers.

Statistical Analysis—Differences in disease free survival and risk for recurrent disease after surgery between patients groups were calculated according to Kaplan-Meier survival model in combination with the log rank test and univariate Cox regression analysis. Differences in survival time and hazards ratios with a P value<0.05 were considered to be statistically significant. The software utilized was SPSS (version 18).

The invention claimed is:

1. A method for treatment of a human subject diagnosed with colorectal cancer and having a tumor, said method comprising:
   a) performing a tumor resection on the human subject and obtaining regional lymph node samples;
   b) extracting and analyzing RNA from the regional lymph node samples;
   c) determining a metastatic potential and/or tumor aggressiveness of the colorectal cancer in the subject by:
      1) measuring gene expression levels of genes SLC35D3 and POSTN in the regional lymph node samples obtained from the human subject; and
      2) comparing the gene expression levels determined in 1) with reference gene expression levels of genes SLC35D3 and POSTN in a reference patient population, wherein higher expression levels of the genes SLC35D3 and POSTN compared to the reference are associated with a metastatic potential and/or tumor aggressiveness; and
   d) giving postoperative treatment or abstaining from postoperative treatment to the human subject, based on the result obtained in a).

2. The method of claim 1, wherein said treatment comprises giving postoperative treatment, to the human subject determined to have metastatic potential and/or tumor aggressiveness.

3. The method of claim 1, wherein said treatment comprises abstaining from postoperative treatment to a subject without a metastatic potential and/or tumor aggressiveness.

4. The method according to claim 1, wherein c) comprises:
 1) measuring gene expression levels of genes SLC35D3, POSTN, and KLK6 in a regional lymph node sample obtained from the human subject; and
 2) comparing the gene expression levels determined in a) with reference gene expression levels of the genes SLC35D3, POSTN, and KLK6 in a reference patient population;
 wherein higher expression levels of the genes SLC35D3, POSTN, and KLK6 compared to the reference are associated with a metastatic potential and/or tumor aggressiveness.

5. The method according to claim 1, comprising:
 a) determining gene expression levels of genes SLC35D3, POSTN, and MUC2 in a regional lymph node sample obtained from the subject; and
 b) comparing the gene expression levels determined in a) with reference gene expression levels of the genes SLC35D3, POSTN, and MUC2 in a reference patient population;
 wherein higher expression levels of the genes SLC35D3, POSTN, and MUC2 compared to the reference are associated with a metastatic potential and/or tumor aggressiveness.

6. The method according to claim 1, comprising:
 a) determining gene expression levels of genes SLC35D3, POSTN, KLK6, and MUC2 in a regional lymph node sample obtained from the subject; and
 b) comparing the gene expression levels determined in a) with reference gene expression levels of the genes SLC35D3, POSTN, KLK6, and MUC2 in a reference patient population;
 wherein higher expression levels of the genes SLC35D3, POSTN, KLK6, and MUC2 compared to the reference are associated with a metastatic potential and/or tumor aggressiveness.

7. The method according to claim 1, wherein the gene expression levels are determined by quantifying an amount of mRNA expressed from said genes.

8. The method according to claim 7, wherein said amount of mRNA is determined by hybridization, sequencing or quantitative RT-PCR.

9. The method according to claim 8, wherein said amount of mRNA is determined by at least one method selected from the group consisting of microarray and bead array technologies, transcriptome sequencing, real time quantitative RT-PCR, and multiplex quantitative RT-PCR.

10. The method according to claim 7, wherein said amount of mRNA is determined using an RNA or DNA copy standard.

* * * * *

SEQUENCE LISTING

<160> NUMBER OF SEQ ID NOS: 32

<210> SEQ ID NO 1
<211> LENGTH: 19
<212> TYPE: DNA
<213> ORGANISM: Homo sapiens

<400> SEQUENCE: 1
agcactcccg tgacgtacc                                                19

<210> SEQ ID NO 2
<211> LENGTH: 17
<212> TYPE: DNA
<213> ORGANISM: Homo sapiens

<400> SEQUENCE: 2
tcatcaccac ctgcggc                                                  17

<210> SEQ ID NO 3
<211> LENGTH: 18
<212> TYPE: DNA
<213> ORGANISM: Homo sapiens

<400> SEQUENCE: 3
cctggcagga gccggcga                                                 18

<210> SEQ ID NO 4
<211> LENGTH: 21
<212> TYPE: DNA
<213> ORGANISM: Homo sapiens

<400> SEQUENCE: 4
cccttgctta ctccctttct c                                             21

<210> SEQ ID NO 5
<211> LENGTH: 24
<212> TYPE: DNA
<213> ORGANISM: Homo sapiens

<400> SEQUENCE: 5
acagctcaga gtcttcgtat atcg                                          24

<210> SEQ ID NO 6
<211> LENGTH: 17
<212> TYPE: DNA
<213> ORGANISM: Homo sapiens

<400> SEQUENCE: 6
acagctgtct gcattga                                                  17

<210> SEQ ID NO 7
<211> LENGTH: 19
<212> TYPE: DNA
<213> ORGANISM: Homo sapiens

<400> SEQUENCE: 7
aaggttatgc ttccccagg                                                19

<210> SEQ ID NO 8
<211> LENGTH: 21
<212> TYPE: DNA
<213> ORGANISM: Homo sapiens

<400> SEQUENCE: 8

```
cttatccatc cactgtgggt c                                            21

<210> SEQ ID NO 9
<211> LENGTH: 27
<212> TYPE: DNA
<213> ORGANISM: Homo sapiens

<400> SEQUENCE: 9
cactgcaaaa aaccgaatct tcaggtc                                      27

<210> SEQ ID NO 10
<211> LENGTH: 21
<212> TYPE: DNA
<213> ORGANISM: Homo sapiens

<400> SEQUENCE: 10
tagtgtccag ctccagcatg a                                            21

<210> SEQ ID NO 11
<211> LENGTH: 21
<212> TYPE: DNA
<213> ORGANISM: Homo sapiens

<400> SEQUENCE: 11
aagagcgatg cctacaccaa a                                            21

<210> SEQ ID NO 12
<211> LENGTH: 16
<212> TYPE: DNA
<213> ORGANISM: Homo sapiens

<400> SEQUENCE: 12
tcccggttcc acatga                                                  16

<210> SEQ ID NO 13
<211> LENGTH: 24
<212> TYPE: DNA
<213> ORGANISM: Homo sapiens

<400> SEQUENCE: 13
tgtagctgtt gcaaatgctt taag                                         24

<210> SEQ ID NO 14
<211> LENGTH: 24
<212> TYPE: DNA
<213> ORGANISM: Homo sapiens

<400> SEQUENCE: 14
ctgatatagc agccctggtg tagt                                         24

<210> SEQ ID NO 15
<211> LENGTH: 18
<212> TYPE: DNA
<213> ORGANISM: Homo sapiens

<400> SEQUENCE: 15
aggaagactg acagttgt                                                18

<210> SEQ ID NO 16
<211> LENGTH: 17
<212> TYPE: DNA
<213> ORGANISM: Homo sapiens
```

```
<400> SEQUENCE: 16
ccgctcccaa gatccaa                                          17

<210> SEQ ID NO 17
<211> LENGTH: 23
<212> TYPE: DNA
<213> ORGANISM: Homo sapiens

<400> SEQUENCE: 17
gtaattccag ctccaatagc gta                                   23

<210> SEQ ID NO 18
<211> LENGTH: 15
<212> TYPE: DNA
<213> ORGANISM: Homo sapiens

<400> SEQUENCE: 18
ctgcagttaa aaagc                                            15

<210> SEQ ID NO 19
<211> LENGTH: 19
<212> TYPE: DNA
<213> ORGANISM: Homo sapiens

<400> SEQUENCE: 19
cagcactccc gtgacgtac                                        19

<210> SEQ ID NO 20
<211> LENGTH: 17
<212> TYPE: DNA
<213> ORGANISM: Homo sapiens

<400> SEQUENCE: 20
catcggcgtc ctggttc                                          17

<210> SEQ ID NO 21
<211> LENGTH: 16
<212> TYPE: DNA
<213> ORGANISM: Homo sapiens

<400> SEQUENCE: 21
tggatcacag cccgga                                           16

<210> SEQ ID NO 22
<211> LENGTH: 18
<212> TYPE: DNA
<213> ORGANISM: Homo sapiens

<400> SEQUENCE: 22
tacacctcgg gccacttg                                         18

<210> SEQ ID NO 23
<211> LENGTH: 18
<212> TYPE: DNA
<213> ORGANISM: Homo sapiens

<400> SEQUENCE: 23
ccgggctgct cattgaga                                         18

<210> SEQ ID NO 24
<211> LENGTH: 19
<212> TYPE: DNA
<213> ORGANISM: Homo sapiens
```

<400> SEQUENCE: 24
tggctaggat ggtctcgat                                                    19

<210> SEQ ID NO 25
<211> LENGTH: 21
<212> TYPE: DNA
<213> ORGANISM: Homo sapiens

<400> SEQUENCE: 25
ggacctatgc ctgttttgtc t                                                 21

<210> SEQ ID NO 26
<211> LENGTH: 20
<212> TYPE: DNA
<213> ORGANISM: Homo sapiens

<400> SEQUENCE: 26
cgctcccaag atccaactac                                                   20

<210> SEQ ID NO 27
<211> LENGTH: 3420
<212> TYPE: DNA
<213> ORGANISM: Homo sapiens
<220> FEATURE:
<221> NAME/KEY: misc_feature
<222> LOCATION: (1)..(3420)
<223> OTHER INFORMATION: SLC35D3

<400> SEQUENCE: 27
agtcggacgc agagctgcct aaccgcaaga acgcctggcc ggagctgccc tctgcagccg        60
agccggcgcc ccctgccctt cgccgccgcg ctgggcgggc gccccgccg ccctcactcc       120 gctgctcccg gctcctcgcg cgcaggtcgc ggagctccgc caccgctggg tgcggcgagg       180
ccggcgcgat gcggcagctg tgccggggcc gcgtgctggg catctcggtg ccatcgcgc        240 acggggtctt ctcgggctcc ctcaacatct tgctcaagtt cctcatcagc cgctaccagt       300
tctccttcct gaccctggtg cagtgcctga ccagctccac cgcggcgctg agcctggagc       360
tgctgcggcg cctcgggctc atcgccgtgc ccccttcgg tctgagcctg gcgcgctcct       420
tcgcgggggt cgcggtgctc tccacgctgc agtccagcct cacgctctgg tccctgcgcg       480
gcctcagcct gcccatgtac gtggtcttca agcgctgcct gccctggtc accatgctca       540 tcggcgtcct ggtgctcaag aacggcgcgc cctcgccagg ggtgctggcg gcggtgctca       600
tcaccacctg cggcgccgcc ctggcaggtg agcgggcccc cgccgcgacc ccagccgac        660 cccacccacc ccgctccgtc gggcagagac cgcggggatc actgagttca acgacctcac       720
ttccagatgg ggagactgag gcagagagag ccggagagct ttgagagtgg tcgctcagct       780
cgcaaaaggg acttccgaga cccagagagc tccccagcgc cccaccaagt cccctgccc       840 cctaatgtcc tggcttccga ccctcgccca tgcttcaccc ggcatcgccc ttcctgtcgc       900
cccctctcct ggtcttcccc tgtcacccca ttctccggga gaggtgggag ggccgcctga       960
gcctgggagc tggagtcctc caagcctgga ccaagccgga aggaggggc cgtgaacttc       1020 cttgggtcac gaggggctgg aatggaggtg ggggatgggg gcgaagctga ggttccgg        1080 ggctactgcg gggtgtctcg tgctgcgcag ggggctgcgg ccctggggca gacgacccag       1140
gtgctgagcg agacgagagc ctgggcaggg ggaagcttca ctgggggcca gaacaggcgt       1200 tctccccgc gcctggcccg ctcggggttg caggccactg gctgggctc cctctccctt       1260

```
tggtgcccca cggggcaggg gctccggggt gcaggtacca cgcgcccaag tgacctcggt    1320
gccagctcgg ggaagccaca gcacctgccc cgagggcatc tgcgctctcc ggggcctttg    1380
tcttggacag aggaagatgg agtgacccgg ggatatggcg ggaaggcgct ctgagcactg    1440
agtttggctg tcgcatttga cacgggtggc cgagggacgg cgggcgtctg tcactcagga    1500
atccggtggg cagagctggg gcgcgaaccc agtctccttt cctacccgac gcgttttccc    1560
cgtgggtccc cgcccacgcc aacctgctgt cttctctctt tttccttccc gcccgggctc    1620
ggccgtcctc ctcgtgcgcc gcaggagccg gcgacctgac gggcgacccc atcgggtacg    1680
tcacgggagt gctggcggtg ctggtgcacg ctgcctacct ggtgctcatc cagaaggcca    1740
gcgcagacac cgagcacggg ccgctcaccg cgcagtacgt catcgccgtc tctgccaccc    1800
cgctgctggt catctgctcc ttcgccagca ccgactccat ccacgcctgg accttcccgg    1860
gctggaagga cccggccatg gtctgcatct tcgtggcctg catcctgatc ggctgcgcca    1920
tgaacttcac cacgctgcac tgcacctaca tcaattcggc cgtgaccacc agcttcgtgg    1980
gtgtggtgaa gagcatcgcc accatcacgg tgggcatggt ggccttcagc gacgtggagc    2040
ccacctctct gttcattgcc ggcgtggtgg tgaacaccct gggctctatc atttactgtg    2100
tggccaagtt catggagacc agaaagcaaa gcaactacga ggacctggag gcccagcctc    2160
ggggagagga ggcgcagcta agtggagacc agctgccgtt cgtgatggag gagctgcccg    2220
gggagggagg aaatggccgg tcagaaggtg gggaggcagc aggtggcccc gctcaggaga    2280
gcaggcaaga ggtcaggggc agccccgag gagtcccgct ggtggctggg agctctgaag    2340
aagggagcag gaggtcgtta aaagatgctt acctcgaggt atggaggttg gttaggggaa    2400
ccaggtatat gaagaaggat tatttgatag aaaacgagga gttacccagt ccttgagaag    2460
gaggtgcatg tacgtaccta tgtgcataca cttatttat atgttagaaa tgacgtgttt    2520
taatgagagg cctccccgtt ttattctttg aggagtgggg aagggaagaa agaaagaag    2580
ctgaaaggta ctgacacaga gcaacaaaat tagcacctgt gtgaattatt tagtgtgact    2640
tcacctgagg catcacagag acaaaagaat gtgaagctac ttaacaaagt aaggcaacgt    2700
ttctgcttca gactcctggc acatttactt tttgtcatta taaccataac taaatatctg    2760
catgtaccaa gagtccctaa gccaccccct ccaaagatgg agtgtagaaa tgatgacagc    2820
acttagtaag ttcaaagatg acattcaggg atgcattttt tgatgataga actcagttt    2880
ttatcgccag ctgggcaaag agtatattgc tgaaatgata tataaatata ttgaattgat    2940
gtttactgtt tatagtcatc tgaaatatca tatttactct gattctactc acttgttttt    3000
taaaaataag tgtcctatta ttgtattata tattgataga aactgttaaa gctatttga    3060
aaatatgagt tcttagcttt aatcatgaag tctgaagttt gctttcagta attattttaa    3120
aagttgtttt ggttcattgc tttataatat ttattattga atgccaaacc tgttcttttt    3180
tttactgtgt ccaatattct ttcaagcaaa tgcaatggct ggaatataat tcagaattaa    3240
ctgaaaccca gccagaagag ggaccacctg taaagcaagt cctttcaagt ttcactgcac    3300
atcccaaacc atgttacaaa aagagcaact gctatattca cattatgata tttttctatc    3360
ttaaatttgt caaataaag tatgagtcta actattaaag gatacattgt tagaaattta    3420
```

<210> SEQ ID NO 28
<211> LENGTH: 36263
<212> TYPE: DNA
<213> ORGANISM: Homo sapiens
<220> FEATURE:
<221> NAME/KEY: misc_feature

<222> LOCATION: (1)..(36263)
<223> OTHER INFORMATION: POSTN

<400> SEQUENCE: 28

```
taatttcatt caatttcctt taatgagtac ttgttacagt aaagaggta taaagtcctg      60
ttcccaagtc caaccactt tttaacttaa atcttgagtt tttctgaatt actcaatttg     120
aagtaattct ctttatatct gaaaaatggt tttattgaaa cgtttgagat taaaaaatat    180
gcattgcaag aagcatatga caaacattct gagagtacaa aattagttgt aaaaaataac   240
ataatttacc agtaaaccca ctcatataga aatgtgcaaa gccttttgat ataaaaagtt   300
ttgtacacca agcacctatt tttataactt agcttcccat ggagagataa tggcttgcgt   360
gcatttatg tatccataac atacatacaa ggctcggtct tttcaatggg ataacagttc    420
acaactcttc gatttgaatt gtaatgaatc tggtgacaag gattttttctc taatggattc    480
caaagttagc cagaactttt aatgtcaaga tgaaaaaggg tgtaaggtgt tatattttct   540
tcaattcctt taccacagga ggctaactcc acaatttccc tcatgtttct cattcagaaa   600
aaaaaatatt aaatttgtgt tcagaattat ttgatgattg cttctttgtg ctgatgtttc   660
agttcctgaa gtcaacttgg ctctcacaat tttctaaggt caggttattg acttagggtt   720
gtataaacat ttttttctgg ttttggatt ttcactgaga acgaccttcc cttaatcgtc    780
ttctagatcc taattagaaa gaaggagaa tgtatagact gtaaatgtta ggaaatttta    840
aaatttaaga atatattatt ctctgtatat ctatcagagg ccattatttt ttgtaataaa   900
ccttagatta tgttttctta atatcttcaa cttatggtga agcaaatatt atattttgat   960
caaaagtata taaaataata atttgaaatt taataatttt aactctttag aaaatttgtg  1020
tcaatttgga tatttacata gatttactga cacattcttt agttaaaaaa tatctgtgca  1080
gttgatcttt tactttcaaa ggtctgtata ttggattggt ttaaagtaag aagttcctat  1140
agcgcattga taagccttgt gtctcctttt cactactagt atctaattaa cccagaaatt  1200
ccaaacttgc aattccaaac ttgcaattta ctctagcttc cacaagggaa attcttgctc  1260
tctcaatgta ttggaatgta agataactta agtggaggaa ttagcaaatg cacatagtgt  1320
aattatgaaa taaattgtaa tgcacatgtg atatatacat atataatcta catatttaaa  1380
tgaacatttt gtaaatagct atattaatgg ttttttgcat atatacattt cttatttact  1440
tatgtctcaa actgtagcat tgtctcacat aataacattt ttaaggattc aggtccacct  1500
gcaatctaca tttgtttatc tctgatattc aacaatttct ttttgactta actcttatat  1560
acacaaaatt atatgtatac ttgtatatac aaaacattac atatatatat atatatatat  1620
atatatatat atatatatat atatatatgt atggagaata tacacttgag tctatctcaa  1680
gggttcaata tgcctagcag tttacatgag tatgttgacc tttcccttaa tatttgttat  1740
tagattctga tagtatagaa catgagaaat ttattttctg attgttatca aaattgtttt  1800
catcaaaact ggctagcttt tctctctgat cgataacaag tttcaataaa atactttaaa  1860
atctttccta ttgtttgatt tctcttcatg taacaaaaga ggccatatac acacattact  1920
atagccaata cacttacctt gaactttttt gttggcttgc aacttcctca cgggtgtgtc  1980
taaaattaaa ttgttgtagt tagaaatact tcgcaattat ggctaaaatc agacaggaga  2040
ccatggttaa acagaacagt gtaaagtctt aaataagtat cacttaaaca cgaagattat  2100
ttttagtagt taaattttat gatcctcaga gttttacatt ttttcgtaaa ggacaagtag  2160
acagacagtg ttttccatat atcataatga atgtttctta gttgcaaaac acattgtttc  2220
```

```
attatggatt ttggaacccc acctaatgtg ccattttttgc agagtaaatg acttacatga   2280
ttttttcaat cttttttgtaa aaaacattgc cttatgatga agggttatta aatgtcatat   2340
aaagtttaac acaagtatct tcccagagtt agccacccat ttttgcagtc atacctatgt   2400
gcaatgtctg cctctgtaaa attatcacta agatcaattt gtgattcctt tattgtacat   2460
tgacgacaac aaagtagcac tgacctaatg attctagaaa tgttataata agtaattcag   2520
aaagaatatg ccatcaccct tgttccacct cccaacctga ttcagtgtca atcctatgag   2580 atcctttttaa aaaattaact aataaaagct tttatattta agaactgcaa gtgtttcaaa   2640
actatgctgt tttgtgttgt tatagttgta acatatttct caattttcct gtttttcttt   2700
tagtttattg acaagactac ctggtcggcc taaattcaca ttttcattca gtttttgggc   2760
atttgagatc aaagagtaag tatggtttct acagttactt cattttttcta cttatctttt   2820 taaatttttt ctccaaattt tgacttcttt tatatgtatc atctatactc agcatgaagt   2880
ccagtttttt ctattatata catgttttca attcgctgaa atcatataaa aagtaagcaa   2940
tgaaactgtc accatgaata gttttggcta tatgacacca agcaaatttt ttaaaaaaga   3000
aataacattc aaaacaactt atatattctg tttctgtcta cttagcacat tttcacattt   3060 cttttcccccc agaatataag gcatataatc atttataaaa ccacattaat actagagtaa   3120
aatatagaac tatagaaaaa tctcactatg ttggataatg gggagaagtc tgtgtaaaac   3180
aaccaagtct gagttatgaa atattctcca acagatataa atagatgtaa atataaatat   3240
ttcttaactt caggtttatt tggtaacgaa ataatggctt ctaaaaaatt gtcaagaaga   3300
gacagatcca acctttaatt ggtgtgcagg cacattgctt atagtggact tattaaattc   3360
caaatagcag ttaattgtat aacttaaaac tgcatcatag aagtatttac caatttcttt   3420
tcaaaacaag tgtgctcact cagatttcct ttcataattt tgatagcatc caattaatga   3480
ggttttgctg tgataatatt ccagaataaa aaacattcaa tgtgtcaaac aaatactttg   3540
aaagaacagc ttgattaatg tgtagaaaac aggtttactc ctagcagctc tctgctatgt   3600
caacatgaat gagagttata ttagatcatg tttagagcag caaaacatgg gaagataaac   3660
caattacttg aatatattgg cacaaagaac caccctacat cttatttcct aaagcatgca   3720
aagtactcag ctcaattatt ttgacatttt atttgcatgt ttgttttttg tatgtttcca   3780
tggttatgac tatggaaatt taagttgggg tgagaaacat tacttaattg accatgttaa   3840
tgtcaattga tgattgacag taacatttga tgacagctta ctttgtgctg aacattgttc   3900
taagagcttg tcatatatta acttatttag actgtaggta tcactactat cctcactttc   3960
agatgaagga acaagcaag aaaagagtca actaatttgg gattgagttg gggctcagac   4020
tgaatgcaga cctacaactc gatctactat tctctataga ggttacaaat cttaacctct   4080
tatgttggca gatttgcgaa aaccttcaaa aatgactttt tgttgttgtt cctttcgaca   4140
tagtctgtta ttctcccttta attgcttgag tcgtttcaga atgcataatt ctaaggtaag   4200
cccaaaaatt ttatgcattt aatgagaaat ttttttcagtt aaggtcttgg aagtgtatca   4260
gtgacaaatc acaacatcag tactcaaagt accagttagc catgttaata gtcatgactt   4320
aaatgattga gaaatatact caaattacca aaagtacaaa aaatgtacta catggccggg   4380
cgcggtggct cacgcctgta atcccagcac tttgggaggc cgaggcgggc ggatcacgag   4440
gtcaggagat cgagaccatc ccggctaaaa cggtgaaacc ccgtctctac taaaaataca   4500
aaacattagc cgggcgtagt ggcgggcgcc tgtagtccca gctacttggg aggctgaggc   4560
aggagaatgg cgtgaacccg ggaggcggag cttgcagtga ccgagatccc gccactgca   4620
```

```
ctccagcctg ggcgacagag cgagactccg tctcaaaaaa aaaaaaaaaa aatgtactac    4680
atgtaccaca atgtatacga tatgaactgt ttagatagaa aattcagttt taggtagaac    4740
ttattgagtt gaagagcatg gttcagatat gtattaattg gccagacctt ggaaaaaaaa    4800
aaagtcttac atagtgtaat ctttactagc ttctttttatc aatgccttt aggatctaga    4860
caagggata cttgtgactc agtaatgacc tgatggtttt agatagctgg aaaaagaaa    4920
acaagcatgt ccaattaatg ctggtactag taattctacc gcatatagtg ttttcctac    4980
aaaaagcaaa accttggaga aatgattga taaaactttt taattttttt tgttttttca    5040
caatgctata atagttgacg tggcattgtg aaaaccgatg ccttacagat atgtagagag    5100
atcatacact gggaactaaa ggaataaact tctgggatga tcagaggcaa gagctaagaa    5160
aggagttcat taactaaaaa ttgaatgtca tatacttaac ttgtagcagt tatatgtttt    5220
cttggctgaa gcaattcttt agtatttaac tggattttc atagtggcct caataacagg    5280
ggcttatcaa aggggaagaa aatatactta cctgaaattt aatcctaaat gaattaaagc    5340
aatataaact gatgcagcta ctaatttatt gattccctaa aaagcactac cattctacaa    5400
agctgcttac tatggcaagg actgaaagaa aaaaaaaga attcaattta atcttcataa    5460
tgtgtttgtc tcttccctca aatccttaga ttttttttcct agcagacagt tgagcattta    5520
ggggtagata gtgaattctt tgttagatcc tacaggaatc tttggttccg ttatggctct    5580
gttgtgctat gtactcttag aattctggga ggaaacttgt atttttcaga catatatatt    5640
tctattgagg gaaaattcaa tcattggttg aattaaaaat ttttaaacta tcactgacaa    5700
gtttctaaat actatttaag agattttacg tttattaaac tacagaatat agaaataata    5760
attgctaaaa atatagaaag tcccaagata atttacattt tcttggacat agtgatacag    5820
ttttaaaaag tataagctga aaagccatct ggactgtgtt ttggataaac atcaaacttc    5880
agttatgttt ctcaattaat agtatatttc aaagtgccta tttggttttt ctaaagaata    5940
taaatacatg tttcacaaaa ataattttt cagcttaatt ctttccttgt taaaaaatga    6000
agtagaaatt tgtttattca aatgccaatg atacaaatta tgtatctata taaacaacat    6060
ctttgaataa ttactatgta gggtttgtgt aagatttga attcttttt ttttgttctt    6120
aaggttcatt taatgccaca gacagagaac attccataaa agattaagat taatttata    6180
tgcaaaataa cttatatcta caggtataga ttatcactca aactgttaga agaaacagat    6240
attcattccc aagaatatag ttttggaaaa gaatgttact aaatgcacta ttttggcta    6300
tatctatgta tagaatttaa agacatgcct tgattgctct tatgggggca gtgaatataa    6360
ttttttaaat ataaaagta tatcaaattt gggcttgttt aacagctagc aatttaacaa    6420
ttatttccct tttgcatact taaaaggccc ttaaaattat ctgaatcaaa gcaaaaaaaa    6480
tattcattgc tccccaaact ttataccata gaacttttta aagactgttt aaactagtaa    6540
tcatttcttc ataactatta actaccattg aaccaatcca tctattaaga caacagtgga    6600
tgttgtcttt ttttttttta acccaattaa aagaaaaaat ctgcttgctc agtctttaaa    6660
aagttgaact cagtcactag aacctgttaa gggggttagt tgttgtcctt ttactaacct    6720
ccctgaagca gtctttttaat ttcttcatct tcaaataaat gaccatcacc accttcaatg    6780
aatttggtga ccttggtgac ctctgagagg atacatgttt atagcagaaa ttggtttata    6840
taacaaaata aagacagcag actttatgtc ataaataatg gcatctgccc aataatgaat    6900
tccagcccaa cactcgattc tttcacaaat tttagtgctg ttttctgaca tactaatatt    6960
```

-continued

```
cttataaagt tgttgaacaa atactgtat aaaaaatatg actgccattt atgcttaatt    7020
ccttattctt gtgcttttt cttgttggta tggaatgaa caatagattg agatagagta    7080
gaaaacatgt agaatgttat tttagacttg tatatggata gcttaggtaa agtcacattc    7140
ttattttcct agaaatgctg accttcttgt aacaatttct tcagagtttc ttctgtttct    7200
ccacctccag tagaaatcct agtgtatttt atttcaggac ctatgagaag gacaatgaaa    7260
aaggtctaaa acagaagtag gcaaacttct tctgcgaagt gacagagagt aagtatttta    7320
cacttgtggg ccatgtagtc tgtgttgcca ttgttcaact ctgatacttc agtgtgaaag    7380
cagcctttagg tattatataa atggatggga aagactgtgt tccgataaaa ctttatttcc    7440
ataaatgggt ggcacaagcc acacttgctc actaattgtt taaacaaata cttaaagaat    7500
agctgaatta aggattttcg gcgaatttta ggctaatttg gaccaactgg acgctagttt    7560
ggaagtctga tatgaggttt actgaaaata ttgatcaatt gctttgtata aacttgcttc    7620
tattttggca ggtagatgta cagacccttaa gattaatgga agctcaaatg aggaaatggc    7680
ttttcttcta gggtcctcta actcattaac aaacagtaaa gtgaaaatgg aatatcatat    7740
caatggtata tcatattaca tgtatgtatg catacatgta ataaaaacaa atgcttttag    7800
atttgtctac aaattttcaa ttcagagtaa aacatagatt acatatttag aataatatta    7860
tatctgccaa aatatgaagt aactttagta atcactatga aaatgacttg tttctttaat    7920
gattcttata tttggggatt aactataatt tgatctttat aatctaggca tagatccatg    7980
tatggaatta atggctaccct gtaatgattc gttcttctcg tgtctctttt tcagttattt    8040
ccacaggcac tccatcaatg attttggtgt atttttaat aattggctct aaaagcaggg    8100
gaatacaaat gcatttgatt taccctcata ttgtgactat acatccataa gctagacatt    8160
gtaatgatta actatatttc tacaaatatt accatttaag attcaatcat aaacattttt    8220
agaacatatc ccccaaaaat catatcaata gggatctaaa aggtaatagc tatgtcctga    8280
atcttggttg agagagaggg ccatttgaca tcctaactct ccatgtcata cttgttttct    8340
ggatgtggaa taaatactta gtgagaatcc agggagttct atatcattgg aatgggagcc    8400
ctatcataaa tcctagtagt ggagtggctt attagacaga gacttataca atggtcattt    8460
tttcctactg tttctaatat ttcctttat actgacatta atgttacaat tttattccac    8520
aatcctcact tgtatatgca aaaatcatga catttgttg ggcccagtga cttaatagat    8580
aaattaattc caactagatc cattaaaagc taactatgtt ttatttctga ccagctaata    8640
agaactcata gctgaggaaa taattcccac aattttata aaataagaac taagagaaaa    8700
tatcagatgt tcaatatttc taaaccaaca ctatttcaaa ataatcacag cgaaggtagt    8760
cggcccccagg taacataagg aacgcacctc catggatcac ttcagttatt gtttcacctt    8820
ctttaatcag tctgaattca ggttcacctt caattttgac ttttgttagt gtgggtcctg    8880
ggacattatt ttaggagaca aattatcatg ttaaaacagt cctttaaatt taccggaata    8940
ggacatttat ttcaacattc ggtgtgactc aactcaaatg tcaaagtggt ttcaggctct    9000
atgaaatcac tttaaatat ttcccattgt cttcaaatta gacaagagtt atgagaacaa    9060
atgatttagt ctgtttgtgt gctactaaaa ttactttcat ctgctttagc ttttaaacag    9120
atggataaat ccatctgttt attcgtagtt ataaagtatg attatgcaaa atattatatg    9180
tggctacact ttgcagatca tgcagtatgt acacatttgt gtttctctga taactggtgt    9240
agatcccact ttatcatact gatattgtct attacttttt ccttattaaa attttttcatt    9300
taagttttaa aatcactcag taccttatat ttttgatcta gtgggtatag gagtgaacat    9360
```

```
aagaaagtac caaatgtata cctaccttta agatgctgaa tgtcaggttt tatgaggaaa    9420
ataatttgag tacttacctt ctgtatggga atgatacaca attaaccagt taatagttaa    9480
acagtccttc aaatgcaaaa gataaactag tgttgcattt gacttgcaaa atgattttgc    9540
taccacagaa aatcattttg aaggttagaa agctgcttac tacattagtt aattaagact    9600
gtttcacaga ggagtaagaa aaataagttc agtacattta actcatactg taatagcctt    9660
caatagtgga atgcaactgt tgcttgctta tctttgagag cattttttt tgcttgttca    9720 gaaattgtca atgtacatga ttaccaaaac gaaaccagcc tagaacaatc caaataatg    9780 aaaataaaag taaagttttt tgaaaccata agtatttcat gccataatat ttgatatata    9840
aggccaaggg atattgagca caaaacataa agccaggttt ttaaggtgcg gtaacttcaa    9900
aagaaaggac gcctaaggaa tttaagaacc aaaaatgcgt taataaaata tctaaatcaa    9960
tatttcttta gaaaagccaa actgaaattt tggaaacatc ctttatagtt aagctctata   10020
aaagaagaga ttttctcaaa attgttttcc tatttactcc caacacctca gaaagtaccc   10080
agcagaatag ctgctcaata actatttgtt gaattgaatt ttagctgatt tattcttaat   10140
tccaaaatgc tgttatgtat cttttataag agacaccta aaattgtgtc ctggagttta   10200
attcatttag taagaattta aaagtcatca ataaatctgt aattgttcaa atagtaagaa   10260
ggaaatgcca gtagcaatcc tggaagctgg accattgtaa attactacta agataaaatat   10320 ttgtttcctt cattatgcta cacaggagtg taatttctga actcaagtta ttaatgagta   10380
ggtgacacaa ctccattttt catccatgtt ccctttataa aagaagcca tgtagagatg   10440 acccgccagt atgatcttaa ctgaataaag attagtagga tagaatccta ctgacaaaga   10500
ttgaggagat aaataagttg aataaagaag cttcaaagga gaagaatctt tgaaaataag   10560
aacattggca catgtaaata atttcaggta aagaagctgt gcacaattat agtgcaaaat   10620
tttagggaat ctgattttta aaaacaggac aagatttgat tttaaaatca attgtattat   10680
caaagatcat tgtgtcatgt tttattacaa tgatcaagga acattttttc aacaaaactt   10740
tctgatttaa tttcttctta aaataccgaa ttgtcttcat cactatagaa agtcgattaa   10800
ataattataa ttatagtatt tttttcaaga aaaaaacaag gatagatttc aaagaataac   10860
tcaattttaa gtctcaagaa taaatactaa tatagataac taattagcta ggaaataagt   10920
ttttacctat gtattttcag tgtataaatt taaattaatg acttacttta aaaaatatag   10980
ataaaagtat tcaagaagtt accttctcaa accaccaaaa gaaatagcaa aaccaaacat   11040
aagtataatt acagtttccc aaagattcca tcaaagatat aatctgttct cttttggaa   11100 gactgtttct agctttctta tagcacaaag gagataacta gttctttct ctgggtaagt   11160 tgctacatta agatgcttat acatggaaat cttaaaaaat ttaaattgtg atccttggac   11220
ataattaaaa tacatgaaat gaaagtaaca tcaaagatgt tgaagttggc taacatacat   11280
agtgggagta gagagaaaag taactgctta tttaatgttc tagtctgaaa catcaggaga   11340
gaatgtgtgt gtgtgtctgt attatatata tctcatgtat aatatatacg tctgtatgta   11400
ataatatgtt cagggctgga attaagtatt ttaaaaatca attcactgca taaactactc   11460
attttgtttt ataattctga tggtctaatt aaaaaatatc tcatgcgtgg ttgtaatttt   11520
aaaagctttc agtaaacata gcttctatgc tatcttatgt tacacaatga aaaatgccta   11580 tactttttt ttttggaaga gcttcttgca ctgttataag aaagaacatg tgggagattg   11640
caaacaaagc aacataaaga gtatacagcc tgtaggagtc tgactaaagt aaaaaaaact   11700
```

```
catgtctttg tttagtgagt atctgtatac taagttaatg caatgccaat tagattcaaa   11760
ttaaatcaag tacaagcaaa tgtactgaaa gtattaggaa tgcatcatct actttgctaa   11820
ataatttgca ctccgcattc tgcaattaca tgagcatgcc attggtataa tattggttat   11880
ataacattta acatgttagt ttttaaaaga atgtagatac attcatagag atcagtattt   11940
ttacagatgt ttttactata aaaggaacca tgtataacat tgattttac cttcagtttt    12000 gataataggc tgaagactgc cttcaatcac tttaattttt ggttccacaa ctttggttat   12060
aattttagtt gctgaaagta tagaaagtgg aacatgaaaa atatttacat aaaaacctga   12120
acaaaggttt tttttttttt tccttttctt ttttgtctct gtaggatact aaggcacagg   12180
atgtggtaat atgttcaggc agtcagatac aggaaatatt tatggtacat aatataatat   12240
cttctcatgt ccaggtgttg aactctgaag tctagtgact tgaatttgat ctagtgaaat   12300
atatactcac aaagtgagga attatatcta gaaatctgta attttaatt gtaccgctaa    12360 agcgctttac cttcttttgt acttcttgaa aatactggct gcattgcaac agaagacaaa   12420
tatgattaat gtcatgcaat tcataatatc ttaaattgca ttgctggatt ctttctcaat   12480
taaaagaaaa aatgaaagaa aaaggctttt aaaatgtttt tcatgcatct gataacagtg   12540
acatagaaag gaaaaaatga aacatagttc agaatactta aaagtaagaa taaatttcag   12600
ccagccagac atgagctcta ttcaacaaac atgatatgat cagtatttaa gttataggct   12660
aaaatgtctt taattttcag ctttgttatc actatccttt ttttttttta atttaaaggt   12720 atatattta aacgtgtgtc gtctacctaa gtaagataat agtctttgaa ctaggtacta     12780
tgtttgctgt ttgggtgatg ggttcactag aagcctaaac cccagcatta ctcaatatat   12840
ccatctatca aacctacgtg tgtaccccc tagatctata ataaaagtaa attaaaataa     12900
attaaatacc agtcaactat ttggttgact tggttgtac tgattaactg gaaatgtgcc     12960
tctgaagcca cacagccaga gcaactggct ttttgtcatt tctaatgaaa agccttgaaa   13020
gatggttcta ttagataacg ggccacactg aagctaactg tgcatctaga tcacatcaaa   13080
gcagtagagg tgagatgtta gcacagcttt ggtttctgca gttctcacct catgcttgta   13140
agatgtttag ctgtgtcaac ttttttgaatt aatgtgggtt cttagccttc atagaccctg   13200
tgtttcagcc ttattaggtt ttgtattttg agatctcaaa ttgtgaagct ctaaaataaa   13260
acaaatctgt gtgtttaggt actagttcca caggtggtct tgccacagaa gaacctttcc   13320
atgaaagtcg aatacgaata cacagggctc tctattgctg ctatcaaaat ggactaattc   13380
cttttagctt acatttttta catcatgtta aggaatttga cgttttggat gttcagctgg   13440
ttggtagttt tcatttcaat cttgattttc tgcagactta aatagttttg acaggtgaag   13500
ctctgaggat taaatattga ttttagccct ctccaggtca aatgttccat atttgacaac   13560
ttataccaaa aacagcatcc ttcccctcaa ctatacactt taaaatggat gttatttgg    13620 ggatgaggat aatatgcagc aaaaaattat aggaattta gaaacaagtc aacaacgaaa    13680
tataaaaata gaaatttgg tttaatttat ctttacttct actttaaaat acttcttaat    13740
aacagcatac cgtctaagga ggagtaaaag aaacatctta cattggaatg taaatgttag    13800
agctgtttca aggcctctgg gtaggtaggg aaggaccatt gaacatgtgt gtcttaataa    13860
aatgtagctt atgctctgtg agtgaggatg taatttagta ggagaaaata attatatttt    13920
tgctcattgt aatcaagata ttgcattcac atatatagaa agtagtgaaa ctaagatgga   13980
taaagaaggg aagctaaaga aatgtagtgg gaatgtgtat atatatatat gcatatgtat   14040
atatttatac ctttgatgaa gaaagatgac ataacatgtc tgatgaatag agcccataag   14100
```

```
gattgcttaa ttttcagaaa acatattttt tacaagattg tattcccatg gtgaatcata   14160
actattccaa ttaaatcttt aatacagtgc tgagctggcc tgatcctgga attgcatgtt   14220
attattgcat aattgaaatc aacaacagca gcagacattt tgttttgctc cttacattgg   14280
ctttactcct tttccatatc tagtataaat cttaagggaa attttcttaa ttaaataact   14340
ggatgctcat ggtataaaat ggaatgattt tctagccaga ataaatgtgg gtattgaagt   14400
aatgttttag ctactgatac actttgagtg tttaattaca gagccaaaac aaaatgaaaa   14460
gaatttctgc ttgaaagcta cagtgaaata aagaaagaga gaaagataa acagagaaaa   14520 agccatgatg gaaaagatat actactagct acacttatga gaatgaaata ccctttatca   14580
ttgttaagta gtagaggttt aattttgata atctggttgt gtcagagatc aaagaaccct   14640
ggaatttgga aactttaaat ttgtcacatg gcagatttt tgttcctttt gtccaatttt   14700
ggatgggaga gttttgaac tgccaccta taaacattgg tattcttcaa cacgtgcttc   14760
tcagcctgcc cttagatagc tcagggcttg agggtggcgt gaacaacaag tcttggctaa   14820
ggtcatttct gtgtccacac atctgaattt ttagatattt ctagagggtc ttttcgccat   14880
ctcttccctt tatatgtctt tttatttcc tggctctttg ccacgctaat attatatttt   14940
gctgtctttc tcatgtcata tcatttctgt ttttccaatg agtggggaag aagttcattg   15000
gagttgaagg ttatctgaga cctcaatcct tttttcaagt gaaatgagat tggccatagt   15060
ttggaattct aaataccaga ttatcaataa tctctgtaaa tacaaagaaa tgtattgttt   15120
tcttttttca taccttgcca cccaggtggc caatatttat tatatactta ctatagacag   15180
tcacggggat ttctttgaag gtgctaccac gaacaaactg aaaataaatg tttatattta   15240
gtaacatgaa aggtgatagt tgtgttaaca aaaccatggc accactttaa ttcttattaa   15300
agtaaaaata gtgaagctat tattacactt aatagaagtg aagtcctcat ataaatcatc   15360
ttccaattca atgctatcag gtcagagggc ataaaaatca ttggattcat tactcagaga   15420 tttaaaatt atataataat taatccaaag ttaaatatat ttatgaaaca caattttatg   15480
tttcctgcta cttttaccct acattgaaaa agaagaaaaa tattccgttc cctttaatct   15540
gtgatgagtg acaattttt ataagtgaat gttcttttcct ttatattctg cagtgaaagt   15600
attgaatgat acaacgattt tagtcatta tgtaccattt tattttcta aattggactg   15660 taaacttttt gaataaagac atgtccaatt taaatacata ttttttcataa cacttttacac  15720 aatacttggt cctgagtagc ttttaataga tatttgttga acaaaaccat gaagaaatga   15780
tgccatttct ttacaggtgg gtcagtggta cataaacaac aaagagtaat ccaagcccag   15840
tacatactta cttattaatg cgtacatttc tagcctgtta tgttaaacct gtaatatatg   15900
ttctacatat tagaaataaa tcaagtaact tttaggctag cgcggtggc tcacgcctgt   15960 aatcctggca ctttaggagg ctgaggcggg tggatcacga ggtcaggaga tcgagaccat   16020
cctggcgaac acagtgaaac cccatctctc taaaaatac aaaaaaaatt agctgggtgt   16080
ggtggtgggc gcctgtagtc ccagctactc gggaggctga ggcaggagaa tggagtgaac   16140 atggaggcg gagcttgcag tgagctgaga tcatgccact gcactacagc ctgggcgaca   16200
aagcgagact ccatctcaaa aaaaaaaaa aaaaagaaa taaatcaagt aacttttagt   16260
accttaattt ggatgtattt gattaattta ttaagtattt ccagcagttg atcatttcca   16320
acaggtgtgt ctatgaagag aaatattaaa tgaatattgg taagaaagca taaaataaaa   16380
atcgaggttc atattaaaaa aagacttagc ctatcaatga gttcaataat tacaaacctg   16440
```

```
ctggatagag gagtttatct acaacatgaa ttacaccatt tgttgtcatg atgtcagatt   16500
cttttgattt caattcattc accagaagtg tatcatttac ctatcaaaat aggaggcaat   16560
ttcaatgagg aaatttcatt aaggatgaat atttagataa cttaatgatg gatgaacact   16620
atcataaatt cattctagac aacttacttc tttcagaaag attttgcttc cttgtgtggt   16680
ctttaaaatg ttagtaacac caggttcaaa tccttttcca atgaaaactc ctggtgtcag   16740
gtgataaaga atgatgtttt gaagagcatt tttgtcccct aggggaaaat atatgtttat   16800
ttttattgaa taatatgact ttttgataag gactaagaaa caaaacactt attagtcttt   16860
atctttttcc atattgtact ttctcataat atcattattc tctcaagtag atatcgatgc   16920
tatttcaaaa catagttatt tcaattagcc taatcaaaat agaacccaac ttactgggag   16980
aaaaaaatct atttattttc taaattataa ctgttttctt ctttgtcccc tgattacatg   17040
gtctttaata gaaaccacat aagtgaacat ctagcccaac aacataacag ttcacagttt   17100
aagaacatta ctgagtgacc ctccacacat cccaagtgga cgaaataaaa ggaaactaaa   17160
gctaaccatg aataccagag aggggcatt tttaaggcag acatctggac aggaaagctt   17220
gagaaagaag tgagatcctg aaatgaaagg gaaaatatct ggaattcact tccacttacg   17280
tatcagaatt tctttttctt cactagtcat tcccttaaaa gcatcattgg ttggcacaaa   17340
taatgtccag tctccaggtt gtgtcaggag ctcttttcaag tctgcagctt caagtaggct   17400
gaggaaggtg ctaagtggga agaatgtata tgtattttgt cagatttaga tttaggtatg   17460
ttcacctaca gtgcatgtaa tagaatagaa tccatgtatt gtggaaagca tgagagaact   17520
gctcatacat tttcatatgt ttcgaataca atttacctgt taaaagttt atcatgaaaa   17580 atgactgaaa tatacaatac aatttttaat ttttttcatc tgatttcatc ctataaaact   17640
tgacaaggtc acacataaca aaaagaagc attttttatca tgtaatactc tacaagatag   17700
tctttgctat atataccatc aatttctaaa aactataaga aaaatgtcaa gaagtagttt   17760
agtctgttag atttgttttc acacatgaaa tcatataacg gtgtaccaga aagtagcagc   17820
gaaaacatat atcaattttg aaaacacttg tatgaacatt ttattctaaa ttccattttc   17880
aaccacatag gagactgaat gccttttggg ataccgccta tgaaacaaaa atatgccaat   17940
agctctcatt ctctgtggag gtgccactaa taggcttacc taaagcgctt atcttgtttt   18000
aacttttcat ggagggattt tctgctggc ttgatgatct cgcggaatat gtgaatcgca   18060
ccgtttctcc cttgcttact cccttttctcc atgcatgaat tttcaatgca gacagcctag   18120
gaaaggaaag aaaggtatgg ggtgtcattt tccttgcttg aaatttcccg tatagatgta   18180
actacataat taagtttccg gatcggccct tctgagaggt tgcctggtgt ctgaggccac   18240
gggaacagct tctttcctct gttttcaatg gctcacacaa actcacaaga cacttcttat   18300
ctagccgggt tttttattaa aagtcaagct accttatgga tcaggcaggt aattttgtca   18360
ataaattaca aaagttccat ggaatcccac ttctacattt tttataattt ctattcagat   18420
ttgaactatt tctctagacc ctcttttggc caacactatc tgtaaggttt cctcacttta   18480
gtgcttttag tgatcttcac aaatatttac tttatttct tgactgtaag accctattca   18540
tcattgtaag tcaaatcatt gacatattca tagcttttg aacgaacgtg atatatatat   18600
acacacatat atttgtatat acaaaattta aagtgcagca catttaatgc atacttaaaa   18660
atgtttggaa ttttgtagct gcagggagct gctgacatgt gccagattca gttctaggta   18720
atgcctgact tcctgtgaag tcttttagtt gtagctgtac gtgttatctg gacaaatact   18780
gaacgtatca ttagttgaac tgtaattttg ataagcaata tttctataaa ttttcctgca   18840
```

```
gcaaaatgta tgttagggct gggtgcagcg gctcatgcct gtaatcccag cacattggga    18900
ggccaaagta ggaggttcac tggaggctga agtttgaga ccagcctggg aaatgtagca     18960
agaccctgtc tcaagaaaaa ttaaattaaa aaattaacta gggtgatgtt gtgcacctat    19020
agtcctagct actcagaaga ccgaggtggg agggtcccct ggagccaagg agtttaaggt    19080
tacagtgagc tatgattgtg ccactgcact ccagcctggg tgacagagtg aaattctgtc    19140
ccttaaaaaa aaaagtaca ttaaaaccct tttttagagt ccagaaatct ctatgtgcca     19200
ataaaggttt atcttgaaag ccattcaaaa gatattcaga tgctgactgg ttattttaca    19260
gtataagatc accttgcata tttgattcat tataatgaaa tgttttgaaa tgaaaaacat    19320
tttagtagag acagcatagt gctaacacat tgtatgtgta gtcaatgcag aaactaatca    19380
acaccttgta aaacatttat tatttcttat tgcaaacaat catcataaag aaaaatggtg    19440
tgtaggcaga gaacagaatt accttgaaaa ttgtaaagta ctctgcaaag gaaaagttta    19500
ttttaaaaaa tttactgctt tctggaattt aaaataattg atgctctaga atagaaagtt    19560
attcataatg aaacacatgc aaaatatcta tctgagtttt gaatacatag cacttgttgt    19620
ggactttgct cacagtcttt tcacccaagc tacccagttc cctgatgctt ctatgaatat    19680
ttactattag aaccacactc ataaaattct gtgaaatatt cattgaaaca gcattatttg    19740
acatgtcatt tgacagactt tttatttgt tgtgattcac ttactgtacg atatacgaag     19800
actctgagct gtttgcctcc gatggtttcc agtatttgcc cgttgtaaag ctcattaagg    19860 ccaacttta ctttcaatat gtgattctgc agaattaatt taaggaggcg ctgatccatg     19920
ctgagagtat catctgtaaa taaattcatt aagaaagagc attatttat ttagaaaaca     19980 ttgaagtttc tcccggtaag acagaatcat ataaacagat aatccctgac attattgata    20040
tcatggattt tgcactcata taatacatga atcaaccaaa tgctaaaaac taacaattca    20100
attcaccaag tagaaactct gtgacctatt gtattaaatg acaataatac agttccaacc    20160
agttcaatca atgagtttca cctctgtaag ggctacatag ttttatagtg gtcactggca    20220
aatgctaaac cttaatggtg gccaaggctt tgtctgataa ttagatatct gttagtcaca    20280
tgaaagaact actgatgaat cctttgtaaa ttaatcttga ttactggaaa gagaatcaaa    20340
gcaaacaacc tcttaaatat gggttattgt caaaacacat gggcaggatt attacaaaga    20400
agaaagtcag gatatctagg aattcaattt ttttgattaa tagttttat atcacaattt     20460 agcatttgga aaaacaaaaa attgtgttac ctattttaa ttaataaatg ttgcctaaca     20520
atttaaatat gtctgtgaaa tcattttcct gagaaaggtc gaaggttgca tgaatctgaa    20580
catggtctgt gaatagcaac tactaggtga aatatttata tatactattt tacatcatga    20640 tatgaagtg tataagtctc ttcattttat ttatttataa tttgacaccc ttactgtcca    20700
aattttgaga tgcaaaacac acctatttat ttctaaatat tattatgttg gtatcaaata    20760
aagaaatcag ttttattttt ttagagatct gtcaatgcat ccttattgtg ctggaaatat    20820
tagattcaca gagaaactaa atatgctttt tttaagtttt cgtttttttt tttttttga    20880 gacggagtct cactctgtcg cccaggctag agtgcagtgg tgccatctgc ttcctgggtt    20940
cagttcaatt ctcctgcctc agcctcccga gtagctggga ttacaggagt gcaccaccac    21000
acctggctaa ttttgtatt tttagtagag atgggttctc accatgctgg ccaggctggt    21060
ctcaaactcc tgatctcaag tgatctgcct gtccttggcct cccgaagtgc tgggattaca    21120
ggtgtgagcc accacgcctg gcctgaatag tcttaattac aaattacaaa tttcactctc    21180
```

```
tgtaggctat tatccattat aatgaaatgt ttagaaatga agaacatttt agtagagacc   21240
atgtagtgtt aacacattgt atgtgtagcc aatgcagaaa ctaatcaaca cctcctaaaa   21300
catttattgt ttcttattgc aaacaatcat cataaagaaa aaaggtgtg taggcagaga    21360 gcaggaacaa cagtgtccag cacataccag aaaatgcatt attcacaggt gccagcaaag   21420
tgtattctcc atctggcctc agagcagatg ccaagcctaa ttgggccaca agatccgtga   21480
aggtggtttg ctgttttcca gccagctcaa taacttgttt ggctgaaaaa taaaccatca   21540
ccatcacaac aatgtcatca ttgctattat ctccatcatg aaactagtaa atcaattcct   21600
gactcttttc taatattgta agctatttac tgcaatgtca gtgtgataag acatcctcct   21660
cctccctaat aagagagttc cacttccatt ttttggtggg agttgataat cacgataaat   21720
ttcagaagga aaatatttt ctgtcttcct actacatgtt tctttaattc tctattgttc    21780
atctctcatc tttctctcta tactgtgagt tccatagctt ttccatttat ccaaagctga   21840
ccatttggtt agatctttcc ttctctttcc aagaaaaact ctggcactgt gaaaacggtt   21900
ataaatatta gatgtcagaa accctagaaa gccaaagatt catgcatgga gttcccatca   21960
ctacactgcc tatctatgga gtgctcaagt agctcactat ttattgtgtt agtgctttgc   22020
atgccattct ttatactgca cattcatttt tcatggactt actctttgag acagcataat   22080
tagtaaatta cagtaagtaa aaaaacaaaa acaaaaacaa aaaagttgc ttaccagaat    22140 caggaattag gacctgatca atcaaatgga tcacaccatt atttgtcaca atatcctttt   22200
tgttcaccat tttgattcca tttactgtta tactgtcacc gtcacatcct atctcaattg   22260
tatttccttc cagcgtctca aagactgctc ctcccataat agactcagaa cactggagag   22320
tatttaagat gtggtacttc ataagagctg gagaacacaa taaaaacagg tagctttcag   22380
atcaagggaa ataacatttg accctgaaaa gatgtgtttc actgtggaac taagtattcc   22440
ttaaaatgta gtaaaaccta aggattcact aacagcttta aaatcctatt tatgttctaa   22500 aagtttttc ctatcaacta taaaatagaa acagctcagc ttcgtaggaa taataagagg    22560
agatcagctt caggaaatga ttggtgcagt attagaaaac gtggtaggtt aagttccagc   22620
tatcataaaa aagtaactcc tgatgtgaaa gcaagaattg ttcctttcag aggaactttg   22680
actggcacaa gggctcacac ctgtaatccc aacactttgg gaggcctagg tgagaggatt   22740
gtttgaggcc gggagttcaa gaccatgatg agaaacacag caagatccct ctctaccaaa   22800
agagaaagaa aaggaaggcc tgtgaaattc caaaatccc aagagcagta tcttgtaata    22860
gctgctcata gcagaatatt tgtatataac atgtaatgag gtcgatagag gctgaggata   22920
agacaaatta tttccggaag gcaacttcta gaaagtaacc aaataaagat gattcattga   22980
aggacctctg gagggatcta tgcctcaact acattatatc tatcctgcat cctaaaattt   23040
tctcatctta aattggttaa atgtattttg ggataggctg agtaagtgaa gtatgcaagc   23100
acaatgtaaa acctatctga caacagcaaa gaagcttgga aagccaccaa attcttatgt   23160
gtatcagtaa ttagaggccc aagagaacca tacagttctc acaactcaat atcttttggc   23220
ataaatacag aattaaaagc attgcataac gtgcatacaa tattaaaatt tgatgatcta   23280
atatttcttt ccaacacctg ctaatccttc tgaatatcta ctacttattt acttgaaagc   23340
agtatgaaag aatgtgatct tgagagtatt cttattattt aagaattata ctctgcctac   23400
tcttttaagg acttttggaa gacatagtac atctcagaat aaaattttt ccctgccttt    23460 gcttattaaa actaatatta ttggtaagga ctagcctctt ttttattccc ttctcagaat   23520
gctgggagac tccttagaga tgaagacatt aaactacctt cggaagccac tttgtctccc   23580
```

```
atgatccttt ctaggacacc tcgtggaagt ttctcaaaag cctcattggt gggagcaaag   23640
agtgtgaagt gaccgtctct tccaagggcc tccaatatgt ccgatgtgat ggcagctgcc   23700
tgaaacacaa atgtgctttt cagagacttt cacattgtaa atccagaaaa agattgcaac   23760
acacttagcc taggctgaca tgaaggagct gattcctaca ctatagaggt ttgttgttgt   23820
taaatcttca aaatattact ttttgacaca accatgtctt ttccaacttt cttcaaattg   23880
tgtttgcaag aatgggaatt ctgcccatgt ttatgggact gtagcaatat ccagcagtac   23940
atataataac agatgaacac gttctaaatg agctaaatac acgccagtca tgtgactaac   24000
cattcttact ctatcatgtc cacagaaata ttattatttc atatgagatg gtttcttctg   24060
tgtaaaatga aatagtagt cctttcaaaa aatatgtgtt acattttgc cagatttaat   24120 agcatttta ttgtttttag attttgacag gagaagaaga gggatttcaa tgactcaaga   24180
caatctgctc ttggacttac tctaaaagat gaaaggtcat cttctgcttc aatgaagtct   24240
tgaattgagg taccaattg tgtaagcaca cggtcaatga catggacaac accatttgtt   24300
gcaatctggt tcccatggat gattcgagca caattaacag tgacaaccta taattatttg   24360
gaaaaatcaa agtgctgaaa ccagagatac ccattgacca ctgagactgc aagcccattc   24420
ccagtttttc atttatacta gtaaatgtaa catacaggaa actacattgt aaatgtaaac   24480
gctgtggatg aagatttaca tgttgttata tctaaaaaag aaactgtaag agaaaaggga   24540
accagttgag aacccaagtc aagtcatact taacatatct agcaacataa ggcaaaggtg   24600 ttttttcat ttaaattatt gcttttctct tttatgcaaa tagtcataaa ctttttaatg   24660
tgggtcaatg aattaggtaa agaagtctaa tcagtcctaa aatttaagtt ttgagaggga   24720
gaaacaaata attattgtat agatataatt agttacatta caagaacttc ctaaaaattg   24780
tttcttcatt gacctctttc gtccctgaga atttggctgg ctgtggaaaa agtcctatga   24840
ccctgttggc agtttcccac aaaatctgat ccaaacacac aagtacttca gttagtacag   24900
tagctagagg gggagtaaaa gaacactcat tctttgatta ttcttttgc tactacgata   24960 aattatttca aacatatcaa ctactaaaat ttccttttct agaataccctg tctactgtca   25020 atgaactgtt catgtaattt gtcctttaca atcactcttt agtagaaatt aataaccaga   25080
ttggaaattt acatgcccta gatttggggg taaagtcata atatagcact taccttattc   25140
tcactaacat tttattattt ttgtgagcat tatataaaaa gtagacaa aattaaagaa   25200 ggtattttc ataagtgtac ttttactga taaaacttac cccattagga taatggttaa   25260
tgaaaagccc caaattgtta tacattgaag gaataatcat gccattttt aagtccttgg   25320 tcaacattct cttattaatc atgtgactat gtaaagcatt cagtaattca acattcacgt   25380
tgctctccaa acctctacgg atatcctagg aaaaattgca atgatagaaa ttcaatttat   25440
tgtggaacat tagtaaaagt cttacgatca ccctatttct actctcttgc tatttctca   25500 tttcattatc agatggtcat acaaaattga cataaataac ttaaaattat attattctaa   25560
ttggttaagg gattttgtaa gttcagatac ttacttaagg atcctgaatg tgatacagta   25620
cttagaacac aattttaaa gtgaatatgt tgatgaagag acaatcttga tataaataat   25680
aaaatgataa gaaagggaga tatgaaatta tcacatattt aaaatacttt aaatggcaaa   25740 caaagaaaa caaaatgac attatatttg tatgcaacac ttaagtttta acaagggttt   25800 catgttatt ccataacaaa ttcaagaatt caactgtcct gtacctttt atctatccaa   25860 cactatgtgt catattatgc tttactcaat gctatgggaa atataatgat aagtaaagca   25920
```

-continued

```
aaaagtcaca actgtttatc atatagcagc aggtaaaagt agacagagta agatatagga    25980
cagaggggaa aaatgctttc agggctccaa taagaaagaa cagctattcg gaagtagttt    26040
ggagatagac catgagattt aaatgaatag gaatggtgtg gtggtctttt aaatccagtg    26100
ctgagatagg gtgaatgcca agagagcaaa agttgtccag tttggttaat acacactttt    26160
atgtttctca gataatacta agaaatttag aagggtatgt gggacaataa cgtggataac    26220
tttaatgccc taagaggagt gaaataaact ggccataagg aaccactgaa gattttgtgg    26280
cattggaatt taatgattag aaccaggctt caggaaggtt gagtggtaat gtacagcaga    26340
aattagagta ttaggggat cactttagat gaaacatgag atgaggctaa cagcagtttt    26400
taagaattgg agaaggggga ggtaaggatg gcttacaaat ttcaagtctg aacattgaca    26460
ctggtactgc caattgtggg gaaaagacaa caaaaaaaac caattattta ttgggggaa    26520 agaaaattgc atatgtttta gataacttt gtttaaagat gcagatggta tatccaagga    26580
taaatgctaa gataaacaat agaaatattc tactgaggtt ccaagaagaa acaagtccaa    26640
acaacaagcg taggtttact gtttgtatgc actaaagtga tagttgaaac catgataagt    26700
gcatttaaag agcagagtca agtgctggaa gaaattctta taagttccat tcttttatt    26760 tttattttta cttttattta ttatactttta agttttaggg tacatgtgca caacgtgaag    26820
gtttgttaca tatgtataca tgtgccatgt tggtgtgctg cacccattaa ctcgtcattt    26880
agcattaggt atatctccta atgctatccc tccccctcc tcccacccca caacagtccc    26940
tggtgtgtga tattccccctt gctgtgtcca tgtgttctca ttgctcaatt ctttaaggca    27000
aggaagaaga tgagtcagca aaaggaactg gagaggtggt tagagatgcg gtgaaagaca    27060
accagaggag cgatttctat aatcaagcaa ttaaccacac agctagtgta gcaagataat    27120
gcctacagat atatacctac attttattat gtatatttca ctctagtaat aattatcaat    27180
tcatctccat atctagtaga aagtaggaat gtatttttat atcagtttta tagattcgga    27240
aattgagtaa taatttaagg cattgtaaat tagactgtgc acaaaagtct gaaaatcaaa    27300
tgtattttca catttcattt aactatccac atacatgtat acaaatttga caacctgaac    27360
atccatatat atacatataa ttaaacatac gtaataaaat attgctgtat aatactgctt    27420
atgataattt taaatttcag taggcttctt aacttacctt tctgttagac atgttatctg    27480
aaattacata catatcctca caaacaaaca ggaaagagga aaggagtaaa atagaatagt    27540 aagtgcccctt ttagctgatt cttgattccc cttcttaaaa aaattaaagt ataagtctcc    27600
tggagattta ttctatttac ggatgtatta agatattta cttcccttaa taactcatcc    27660
ctttaggtat tctcatatat gtacaataga aagatataaa atttctacta atatccaagt    27720
taataagtca gttaaaatga aataacaata acagcaaaaa ataaatatat tgataaaaat    27780
aatgaattac agaatccaag ttgtcccaag cctcattact cggtgcaaag taagtgaagg    27840
atcccttccc ctcgatctcc tccctcagtt ttgaggcgtc agaatagcgc tgcgttgtgg    27900
tggctcccac gatgcccaga gtgccataaa catggtcaat gggcaaaact gaaataatca    27960
agaaatgaat cagtactggg gataatattc tcaggatatt attcataatc atttaaactt    28020
tatgctgtgt ttcccaagac atttagctaa taattttagc aatacaatta tatgaataat    28080
catttttata taaaagttat cttttgagtg ctaaataata aaatgctact gaaaaacatt    28140 atttttacata tcctttgtgt tgaggaaaaa aaaatttaaa ctgtcatcct ggtttaacat    28200
ttaacctatt tagatctcaa tcctgctatg tcaataataa ttcaattata attcaatatt    28260
atctgttatt taaatctatc attttatag atttgggtcc ctaaaaatat gtaggcctgc    28320
```

```
ttgttttcat tacaatttct gggagcaaat gatttaaaat attcaatcct tccagattat   28380
ttctcccgaa cgtcagaaga aagattcatg aatgaatgtc agcctgaagg gatttatctg   28440
gtaatgtgca gtcaacttat tttttctgac cctatttatt tgaaaattag tataatttga   28500
ttaatagcat agaatcaatg gttattaaat ttgtgaatat ccttagattt ggtgacacaa   28560
ctattaagta taaaaccagg attttaaaag accctaaaaa gatggagaaa ttgagtcaaa   28620
atgaacaagg ttaaatttaa caaggttcca tgtaattcct atgcctaaat tgagaaaaac   28680
aaatcctaga gacctgactt aatagtgtat gtaaaaaaaa ctgtaatcaa ttttaattga   28740
ttctaaattc aatataagct aatgatgtaa catggttacc aatgacatta tccaaagtgc   28800
aaggtgtccc caaatcaggt acttatcttg gtattgtctt aaatgctcag acccacatgg   28860
atggacttta aatatcagtc taggtttgta ttcagaagaa agattactgg actagagact   28920
ttctgtgggt tggtgttata atggggaggg cttcaaagtc tgtgtcatat taaaagaatt   28980
ggggatggtg agccagagaa tagaagactt tattcaagaa gagaaggtag ctggaggaaa   29040
ggtgtggtga ttggcatgaa atatctgaat ggctgccatt tcaaagagga aatagatgag   29100 ctatttttt tttctctagt tggcagaagt agaggaaacc aaatttcaat ataaagaata   29160
ttataaaatc agagctgttc aactagagaa gatgaagttt tgccaagtag ttgagttcca   29220
tgttcctaga caagttcaaa gaacaggatt ttgtaaagag ttttgttcct gaagggaagc   29280
tgaactaatt taaatttgtg actaagtttc tgttgtattg cccagcatcc agtgcatgag   29340
aaatatgctc ttatatttta tcattcataa attcatgatt aacacaaaaa taggagggat   29400
atatcttgga tttaggatgg tgctgaatac acacatacac aattggcttc tccacaagcc   29460
acctcaaccc tttctttgca tataattcct tatttaattc aaaaaattga gattttacct   29520
gctgggcagc ctttcattcc ttccattctc atataaccag ggcaacattc atataacaca   29580
gtcctgtaca taggaagaaa attaatatta aaatgagaaa ctaaatagga tacattttta   29640
cataaatttg acaaaatatt tcacttattg acttgatttg ttgaggttct aaaaatcagg   29700
ttttttttcc cccctgattt tttctttttt cttttgagac ggagtctcgc tctgtcgccc   29760
aggctggagt gcagtggcgc gatctgggtt cactgcaagc tccgcctctc gggttcacgc   29820
cattctcctg cctcaacctc ccgagtagct gggactacag gcgcctacca ccacgcctgg   29880 ctaattttt gtattttag tagagatggg gtttcgccgt gctagccagg atggtctcaa   29940
tttcctgacc tcatgatccg cccacctggg cctcccaaag tgttgggatt acaggcatga   30000
gccactgcgc ccggccgatt ttttctatat ttctatgagt ttgatttctc actacagtct   30060
catgttacta tagaaaagtt ccataatgtt gatccagaag aacgacattt gggtcctagt   30120
tctactactt ggttgacatg tgaaccttga gcaagtcatt taatcaatag gagtccctgt   30180
ttccccaagc atttaacatg aatatagtag ctataatatc tactcacaga gtaattgtga   30240
atctcaaatg aaataatgct tttgaaatca ttttgtaaac taaaaatggc tagaaatctg   30300
ctttaatata attggaaaca taagaaaata cattgaccca ttggagtccg taacatgcta   30360
tctcattgct agataaaaata atgccatatt tggtttgaat tgttggtagg attattaatt   30420
gtattatatt atatataaac tttaaaatct ttttattttt gtaaaatttg ataaaaataa   30480
tctaagtaag tttatttaa tattagagtt tagtattcaa gaaagtggca tcctgtttaa   30540
agttaacgaa gtgtgttaag ttctataggc aataattaag gtaacagacc agaaaattca   30600
agatatcacg atatacaaaa aataagtttta tctaatttac tatattttga gggaaaataa   30660
```

```
taatttaaaa ttatatataa ttgcttacaa aataaaaact gattatatta atgtataatt    30720
atattattaa tattataata taatcctaat ttttattttt tcgcatttca tagaatattt    30780
tctggacttc atcatctaac ataggtagcc tattttaact caaattttac atagttactt    30840
atgtttcctt tcaaaagaaa tataaaggta catgtaccaa acaattagaa ataggggat    30900 tattacaagt aaaaaataaa tgcacatcgt tttgtaattt ttaattgata aatatcatgt    30960
caaacagatt atgacaatta tagattaatt attttgcaat tcactaatta acatgaatc    31020 agcttattca aatgctattt cttttctggc tttttatcca gttgtcttaa ttgtattcaa    31080
gaagtatgaa tgaataaaat aatttagaca tgaaagagat cgccaagtat aagaataaaa    31140 tctttttta gtatgataaa aatgataaaa gcaaactatc aagaagcaaa aattttaatg    31200 atataaaga tgattttata gagttgaata aaagtaaata aatgttttca aattgaaccc    31260
tgctacacta agtaattatc taggatttgt agtctggttt ataaccttgg atcctcattc    31320
tttatttgtt aataaaaaat tcctggcatg aaatattggc ttaagaataa tagatagcta    31380
aaaatacaga caaaattaaa tgggaaatac ccacttcaag ttattctcta attttaatat    31440
agtttgaaga atagttggta ttggaaacat ataaaaggta tataggagcc ttatgcaaat    31500
cataatagag cctctaaata attttattta catgagctct tgtaaataaa tctaattatt    31560
ggatgtcaaa agattgatta acaattgctt atatattagc tttagcatat gttgtaaaca    31620
atttaaaaaa tgagatacaa atgtgcttag tccatagatt gataatactt acttgaagta    31680
aaatagtgaa tagaaaagga aatttaacaa aaaattatta ttagcaaatg ctaatatgac    31740
aagggtcagt cataatgtag agaattaatg cagtagatga gataaaattc cagcagttca    31800
ttgtaatatc atcagataat tgaacaatgt ggttatctct gagcggatat tttgaaaaga    31860
aaaaaaaagc agttttttc agaagaacat ttatgctacc caaaactcaa tgttcccata    31920
tggtcagtag ggcaaaacaa gagtaaaaaa aatattgcta tacatagctc taaacatgag    31980
aaatttattt ttgttttcag aatagtatct aacatttcat gagatgccag ctaaaaatat    32040
cacagacatt ctctagagga agtttccaga atactatatt actagaccaa tatatatttt    32100
ggacaatatc ttgaccctag gaagcttcac gtttttcatt aggcctgctc agtttacttt    32160
tctcaaatcc ccagagcaac tgtcagctga aaggcaaaca tttctgtcat ctgatcataa    32220
agtcctgatg atatctctgg aaatttcagc agaagcaagc agatggcaga ccagtcagtc    32280
ttcctgtcaa tagtattgat ttctttggtt atttgaaatt agcatttaca tttatttcag    32340
tgcccagacg taactatgtt tttgaaaatg aatctacttt agaaaaataa gctaatacaa    32400
ttgaacaaag gagacactgt tacatttctg gttaaaaaaa aaaaagcca ggcttcaaag    32460 tagtgatttt ttttttttta atggaaagca agaaagaatt ttggcatagc ctctgtacaa    32520
gccttgacat ctctcatata tttagatggt taaagtaaat ttatggcatt cttctctatc    32580
ttctaggaag gatgtaataa gcattctccc taacatttca gggtgaaggt cctttcttat    32640
ctagttaagt gtgcatttca aatatgcttc atggtatcca agaatataaa taacaaagag    32700
gaaaactcag agcctagag tccctactgg ggcctagctt gcagcatggc agagatcatt    32760
gtaacaactg attgcattat aattgtgtga atgactcaca agtctagcag aagtctgcac    32820
aataatagga ataatgttca ggtcaaaaga taacatcatg ttgaaactct attaagccaa    32880
tgagcaggag atggtcagca aagtcctctg gtgccctaga cttggttacc atgtggagat    32940
gcaacccagc taagcttaaa tgccttgtat acatggttct tacttagaaa taagacaat    33000 cttgtgcatt tcaaataggc atctggtcac aacttccttt cctgtctaca tctatgcatt    33060
```

```
tgtttaaaag agtttaattt taagaacaat tgatattatg cattatggtt acttagtaat    33120
ttcacattta tcaattcatt ttattttctc agaaactcta taatatagct attaaatcca    33180
tgttttacag gtaagtctac aagaagttaa gtgattccat atttagtatc tttttttttt    33240 ttttttgag acagagtctc actctgttgc ccactcggga gtgcagtggt gccatctcgg     33300
ctcactgcaa cctccacctc ctaggttcaa gcgattctcc tgcctcagcc tcccaaatag    33360
gtgcctgcca ccacatccgg ctaattttg tatttttttt tactagagat ggggttcacc     33420
atgttggcca ggctggtctc gaactcctgg ccacaagtga tccacctgtc tcagcccccc    33480
caaagtgctg ggattacagg tgtgagccac cactcctggc ccatgtttag gatttatacc    33540
aatattatta acttagaaat aagtttctaa taaattattc cacccgaact tagggtaact    33600
gaattttaat gctgatgtat taagcaggtt cttcctgggg tcttttgatt ctcaagggat    33660
ccttcactga gggtggactt caaattaata ggaagcagga aggagccact tgcactgttt    33720
tcttgactgg ggatgacacc taaacctttc tgattgcatt acttgcccta tttatgactg    33780
gtctccctca ttgtaaaata aagactttgg atcacaggag tggttcttga ccttaataag    33840
tccagagtgt ttattacttt tttccaccaa tatttattgg taaaataaac cagaaggcat    33900
gtctattaag taataaataa tgctttcaaa ttttaagcta atcagtgaaa catatgttaa    33960
aacataatca tcctttgggc tattgagata ttaactataa tgatgagctt ccgttatcac    34020
cttgtggacc tctggggatg gagcatcttg aacggagaat cactggatta aataaagaga    34080
taaaactcaa gtatttttta actttaaact ttgatgaaaa ctctccggta aactggaata    34140
ctttagacaa tttccaaatg actagagaca aacattaact ttttgcctca gaaactctga    34200
tattttaaat cagtttgttt ttctggccca ctttttata aaatgaggaa actaagtcac      34260
agaggttaag tgacttgcct aagataaaag agggccaaac caggagtaga aacaacatca    34320
tttactcaca cggattctat acccaatcct gagccatgtg atctgcttcc ttctggcctc    34380
catgtcacat ggattcagga agaaatctga gttctaatag taatattgga gatgcaggga    34440
gaacttcttt attcacgtat gtattccttt cttttcttta ataactctc acaattttgg     34500 tcagtatttt caagaagaat ggtgtgtaca cccaggggaa ggcatataca tcatgatgtt    34560
gtttttggaa ctgacatatt atgaaaaaaa aaagagactt acgttttctg tccacagatg    34620 gacttttat accagttctt acaagtgctg aagtatttct ttttggtgcc caaaatctgt     34680
tgaagggcac agacatttgg gctggaggat agagggaaag gaaaaaagtt aatgtcctaa    34740
taatgactag ttttcgtat ctaaagattg gttgatagaa gaaaatgttg agatgtggat      34800
ttgatatcca aagacatgat tctagccttg cacaaatcta attattgaca caatcctact    34860
gaattgttga aaaaccgaaa gtctacagga ggtggcaggg agagagagaa aaattataca    34920
tttctgagag taaaatacaa gcttttcaaa aagttaacca actaggacta ttcaaacagt    34980
atgaacgtaa ttttatttct atgtgcctta ttacttttaa tggtagataa tctactgacc    35040
ctttttaaac caagcatgtg ctcatttgga ggatggccat aacttcaggg ctctctggaa    35100
caatgagagg tcagagagca aaagagacaa ggtttattat gtacacagac actatactct    35160
gtaattttct aggtaagtaa tcacagaagt aaatgtgcta aaattaactt tgaaacaata    35220
tggttgcaca aaggagaatt tatcttttg aatggaagta acagatcaga acatcctctg     35280
tcacaatttt aaggttcccc ttcccctctt aaagggacag aagtcttttt tcactgtaag    35340
tcaaagaagc ttgtgaacat tatgaaaatt cctgtgaggc ataggaagaa gtgccaagat    35400
```

-continued

```
ccgcttaaaa aattataaat ggttggataa gttacaaaat tatgtgtaat tttaaaaatg    35460
cttagttgta gttgcattag ttctataaaa tataaattac ctttgcaaat tttacagaat    35520
tcagagttta aaagtaactt aaatgcttca aagaattcag agaactagtt acattaccca    35580
gtatttaacc ttcatatgta atttaaataa aattttctct aacatcatgt gagatatttc    35640
aatgctgttt gcatacatat gatagttcct aacaatagat ttttaatttt tgaaaactca    35700
atttcagatt tttggaagaa aataaaaaca taaataaatg gaattataaa agaatgccca    35760
gctaaattgt gttaattaga ttagaattat ataacatttc ataagaaagc aattatattc    35820
aaggtattta gagagcaatt aagtcttaaa gcttaaaagt gcatagataa atcacagaat    35880
actcacattt tcctttttttt cctattactt tataataatt aggaaaaaaa accctgaggc    35940
atatatgaga aactttatgc atacttgaac atctaacaag ctgaggaaaa agaaaaatgg    36000
tttataaaac caaaccactc acttacccttt ggtcccgacc cctgatacga ctatgagcca    36060
agatcttgtc ataatgattg ttggcgttta tagggttaac aataagcagc aatagtagag    36120
aaaacatggg taaaagggaa atcatcttga gtctctccgt tgcagttagt ccccgaagag    36180
aactggcagt gggctttgga gagctcagaa tttatataca tgtcagagtt gtgggaggga    36240
acactgcatc aacctgagag tct                                            36263
```

<210> SEQ ID NO 29
<211> LENGTH: 11043
<212> TYPE: DNA
<213> ORGANISM: Homo sapiens
<220> FEATURE:
<221> NAME/KEY: misc_feature
<222> LOCATION: (1)..(11043)
<223> OTHER INFORMATION: KLK6

<400> SEQUENCE: 29

```
tcataataaa attcattctt tattgagtgc atggtggccc aggtgctatt ccatgtatgt      60
cataggtgtg aaaccttaaa tctttccaac agccactgcc ttatgagac tgtatcatcc     120 ttatcttcat cttacaggtg agaaatctgc agtgaagaaa ggtacatccc aaggggacac     180
cgacagtaag cagcggagct gggattccag acacgtggct gggcctctgc aggaagaaat     240
caaacgtgtg aagggttgg ggagaggaga tgcctagaag ggattttcct gtattctctt     300
agtggtgggg gtaagaccga ggacccaagt cctcactcat cacgtcctcc ccagtgatgc     360
aaggatggag ctgggtaaa accagggaga atcaggaccc tcacgtcgct gcgtttatta     420
agcatcaggt tcagagctgg gcaggagagg aggggaggca aggtctaggt gagagacgtt     480
ctggaaccag ccagtggggt ggtaggtcgg gaggtagatg tcacatgtca gggtcacttg     540
gcctgaatgt ttttttggat ccagttcgtg tatctgcaga cgttggtgta gactcctggc     600
ttctcctttg atccacaggg gatgttaccc catgacacaa ggcctcggag gtggtctcca     660
cataccagcg gacccccaga atcaccctgc aggaaagagg gagaaagtca gatacagata     720
gaaacccaga gactgtgtgt gtgtgtgtgt gtgtgtgtgt gtgtgtgtgt gtgtgtgtga     780
cagagagaga ggtagaaagg gacagaggta cttactgaaa gatggagaga aagactcagg     840
gacagagaga cagagagaga gacagtaaga cacacaaagg cacagagaga gaatggtaga     900
gagagaataa aggagactca aagacacaga gataggaatg ccaagatgca gaggaacata     960
gagagcaaga aagagaaaca atttaagaat ggagactgag aggtgtggag agaggcagag    1020
gtgtagagac cgatggagag agaggaggag gaagaggaga aggaggagga agagagaaag    1080
gagaggagga agaggaggag gaagaggagg aggaggaaga ggaggaggaa gaggagaagg    1140
```

```
aggaggagga ggaagaggag gaggaagagg agaaggagga ggaggaagag gaggaggaag   1200
aggagaagaa ggaggaagaa gaggaggagg aagaggagga ggaggaagag gaggaggagg   1260
aagaggagga ggagaaggaa ggaggaggaga agaggaggaa aaggaggagg aggaaaaggg   1320
ggaggaggaa gaggaggagg aggaagagga gaacgaggag gaggaagagg agaaggaaga   1380
ggagaaggag gaggaggagg gggaagacga ggaggaggag ggaggaggag gggaggagg    1440 aggggaggga ggaggggag gaggatgggg aggggaggga ggatggagag ggggaggagg    1500
atggggaggg ggaggaggg gaggaggaga cgataagacc caggtgggag aggtagggag    1560
ggcccaggga gagatatgcc tggcactatt ctgtccaggg acacctctcc acctcgtgtc   1620
ttgaggacag tctcgcccac ctgccctttc tttgcgtcca acttgctatg tatcgctttc   1680
cctgtctctg tccctgtttc tgcctgtgtc tccgtttctg cctgtgtctc ccccttggtt   1740
ggtctctgca catccctcag tgcattagtc attctggcat aaagaggaga gcctggatgg   1800
atgacaatgg aggaaaccca agttaaagta ttcgggaggg agtccccttt ccccagctag   1860
tgtctccctc ctccagagcc tggtcgtttc tgagcaggac tcgtgggggc tctgtttgag   1920
gaaggacagt cccctcacac catctgcttc cttactactt ctctttggtt cttttgttt    1980 ttagacagag tctggctctg tccccaggct ggagtgcagt ggcgtgatct cagctcactg   2040
cagcctctgc ctcctgggtt taagcaattc tccagcctca gcctcccgag tagctgggac   2100
tacaggtgtg tccaccatg cttgcgtaat ttttgttttt tggtttttt ttgagacgga    2160 atcttgctct gttgccaggc tggagtgcag tagcatgatc tcgactcact gcaacaacct   2220
ccgcctccag gttcaagtga ttctcctgcc acagcctcct gagtagctgg gactacaggc   2280
gcctgccacc acgcccagct aattttttgta tttttagtag agatgaggtt tccccatatc   2340
ggccaggctg gtctcaatct cttgacctgg ttattcaccc acctcggcct cccaaggtgc   2400
tgggattaca ggcatgagcc actgtgccca tcctaatttt tgtattttta gtagagatag   2460
ggtttcacca tgttgatcag gctggtctcg aactcctgac cccaggtgat cctcctgctt   2520
cggcctccca aggtgctggg attacaggca tgagccactg tgcccatcct aattttttgta   2580 tttttagtag ataggggtt tcaccatgtt gatcaggctg gtctcgaact cctgaccca    2640 ggtgatcctc ctgcttcggc ctcccaaggt gctgggatta caggcatgag ccactgtgcc   2700
catcctaatt tttgtatttt tagtagagat agggtttcac catgttgatc aggctggtct   2760
cgaactcctg acccaggtg atcctcctgc ttcggcctcc caaagtgccg ggattacagg   2820
catgagccgc tgctcctggc ctctctggtt cttgatcccg cggcctccat ccttgtctct   2880
gcacttcctg tctctgctgg ctgtgtcttt atatctctgc atatccctga ctgtgtctct   2940
gtgtgttgaa ctaagtctct tcttttcaag gcttgggttc tccctcagcc tgtctctatc   3000
tgtctctgta aagctctctt ttggcctgtg tctctctctt cctgtgtctg gccatgtttt   3060
tgtgacttcg tcctgtccct ggctgtgtaa gtggcagatc cggtcacct cacctggcag    3120 gaatccttcc cgtacttctc atccccagca cacaacatgt tctgggtgat ctggccaggg   3180
taggcatgct cacactcctc acgggacacc aggtggatgt atgcacactg gatggtgtca   3240
gggaaatcac ctgttagggg agagatgggc cagactcagc ccaggccttg cactcccctc   3300
atcctcccca gtcaccccccc aaccccctata agtcctccat cctctattgg tccctctttt   3360
ctattggcac ccctcttcct gtttgtctct cattcttaca tctcattacc atcgtccctg   3420
cctcctaatt ggtccctctt tctatcattc ttccccccca ttggctgtct tcctcattaa   3480
```

```
tagtctcttc tccaggagtc ctcatttcct attggttttc cttttctctt aggtccctcc    3540
tccacttttc tctcttccac tggtcccacc ttcttcagta gtttcagttg acctggagga    3600
ctcttcctct gttacgccct cctctactgt acccctcctg atcagtagtc cattcttcat    3660
tggacacttc ctgcccattg attcatcttg attggtcact ctgtgaccat ggtcttttc     3720
ctaactggcc atgccctctc ccattggttc ttcctttcta ttggttcttc atccaatggt    3780
ccacctccat cattggtcct tttctaactg tccccaccct ccctcatgga tcctcccttt    3840
ctattggccc ttcctccaat ggtctacctt cctcattggt cctttcctaa ctggccctgc    3900
cctccctcat tggctctctc ttcctattgg tctgcttccc tccttggtcc ttttctaact    3960
ggcctcacca tcccccactg gctctccctt cctattagcc cttcatccaa tggtccacct    4020
ccctcattgg tccttttcta acttgccgca tcctcccccca ttgtctctgc cttcccactg    4080
gcccttcatc caatggttca ccttttcttat tggcccttca cacacaggcc caccttcatg    4140
gatcctgctg atctattgga cctgtttttt cctctagtga ctcctctgga ccattgatcc    4200
tttccccttta gtccctcttc catcagctat accccccattc actgtctcaa ttcacatcct    4260
tcagttggct tttgtgcttt attggttct cttcttccat cagttccttc tccattattc    4320
cttcctgctg ttcaatgaat cctgatcagt cccccttgac ctttgacatc cttcctgatt    4380
agcatctccc cactgacctt ccctctttat tgaaccttca tcttatgttc catctctccc    4440
atgctattca cccattggtc tacattttcc attggctgtt cactcactgg cccagctccc    4500
aaattcactc tccctccccc ttgaccttc tcccattgaa accctgtccc attggtcctc    4560
accattagcc catcttccca tggcccctca ccaattttcc cactcccat cctttggcac      4620
acttccccaa gtagccagta gcctgctccc caccagcctc ccactactga ccatctgctg    4680
tcttgccccca gccaggatg tggcagctgg tggtgttggc tgagcagtcc ctctccaggg    4740
gaagggctg gatgagttca gagagtttgg ctgggcgtgc caggcgcaac agcatgatgt     4800
cctggtcatg gctggcggca tcatagtcag ggtggatcac agcccggaca acagaactct    4860
gctcctggga actctcccctt tgccgaaggt tatgcttccc caggaagacc tgaagattcc    4920
tgggaaggaa gagggctggg tctcacctgg agcccttggg ctgcagttga ggcttcagag    4980
agggctggga agtcatgaat cgctggcctg ctcctcccac agtcttcccc agctgggtaa    5040
atggcaattc catcctttca gaataatctt ggggctatt cttcactctc tttatttcat      5100
gccctacatc caagctgtcc agaattcctt ttgcctctct gaagcatatc cagaatctgg    5160
ccacatctca ccttttcccac ggctaccatc ttggtttgag ctgccttttc acttcctacc    5220
tgaactagag cagtagcctc ctcactgggc tccctgctct gtctctggtc ccccacagtc    5280
catcctccac aaagcaacca gagatatttt aacaatgtaa gttggtcctg tgcctcctct    5340
gctcagcccc tcctatgact cccatctcac tcagaatcaa agccaaagtt ctcaacgtgg    5400
cacaccaggc cttgcaagca ctgcccccatc atctcacaga catcttctcc tcccactctc    5460
cccttctctc cctctgctcc agccaaacgc tggcttccct gtcttgcctt gaacacaata    5520
gtgatcttcc cacctcaggg cctttgcact gctgttccct ctgccagcaa gtctgtcctc    5580
caagtatctg catagctcac tccctcactt cctttaaatg tcgcctctca gggaagcctt    5640
ccttagttgc ccaattaaaa tacaaatacc tgttagtagg caattcctat ctccctcccc    5700
tgctttctgt tccaccagag aacctatcac aatcatccga cctgctatat atttattgtt    5760
aaatatttac tcattgtgtt atttctcctc cttgcagagc aatgctgtcc actaaatgct    5820
acgatgccat gatctcgatc tgcactgtcc agaggtggct gggggaacca caagctacag    5880
```

```
gtggctgctg agtacttgaa atgtggcttg tggattttcc atttcattaa tttcaatgta      5940
atttgctata tgtggctgat ggctaccata ttagacagtg cagctctagg atgtcaagat      6000
ggggattttt gttctattca gatatagtat ctccagtgcg ttgatcagca cctggcacag      6060
gataggtgtt tgatacatat tcctgaaaca gagagtcact cccttgctca gacatcaccc      6120
atggctcccc attgtcctaa gaataaagcc tgggctcctc cacttggcac tggagcccct      6180
gtgtgatctg gctgtagtca ctttccaacc ttatctccca gcaccttctg cccccagtg       6240 aacgggaaat tttatttct gagaatactc aagacggttc tcacctcagg ggtgttatca       6300
cagcctttcc tctgccctga acattccttt tcccatcttc atgcctccgc ttggatttta      6360
tctcattaga aagtccttcc tgaccctcct ccatctaaag taggtacccg tattcttttc      6420
cttcataatt tgtaattata tggggttttg aagggtttgc ttcttttgtt tgtttgtttt      6480
tttgagacag ggtctcgctc tgtcacccag gctggatctg cagtggtgtt ctgtagatca      6540
cagctcactg cagctttgta ctcctgggct cgagtgatcc accgcctcg gcctcccaaa       6600 gtgctgggat tacaggcatg agccaccacg gccagcccaa tttgctgctt ctttctttcc      6660
tttttttttt tttagacaga gtctcgctct gtggttcagg ctggagtgca gtggcgcgat      6720
ctcggctcac tgcaacctcc gcctcccacg ttcaagcaat tctcctgcct tagcctccca      6780
agttgctgga attacagaag cccaccacca cgcctggcta atttttttgta ttttcagtag     6840 agacagggtt gagccatgtt ggccaagctg gtctcgaact caggtaatcc acccacctcg      6900
gcctcccaaa gtgctgggat tacaggcgtg agccaccatg cccagccctc actttgcttg      6960
tctgcacctt tctgtccttg tgctcccgag ggcagggatg acgtgtgtgt cccatccatt      7020
gctgaatctc cactgcccaa ctcgaatgtg gcacttagca ggtgctctta gtcaatgtac      7080
atcaaaggaa tgaatgatgg tggtgagagt catccaaggt ctccttgggg tcagggggaac    7140 caccccaggg attgtcactt gctatttccc tgcacctcag tttcctcatt tgcaaaatgg     7200
tgccaagagt cccttgtggt gggcattcca ggaaaggtgt gtacatggtt tcactcagca     7260
cctgattggt agttagcatc aaacaagtgg cagctgtcgt gaatctgact agtgaggatc     7320
agcgcccagg gttttgtcc tgggccctcc agctcctcca actatgccag ctttttggat     7380
gatctcatct agtcccatgg ctttaaatac acctgtttgc tgacgatgcc ttcattttaa     7440
cctccagccc tgacctctcc tctgagctcc agagtcctcc ctggcctccc tgctgggaca    7500
tctccccggc atctccaact catcgtggct aaagcaaaat gtcagatgct cccctgccta    7560
cacccggcct gtttctcttt ccctctccca caactcagag aaagacgtgg caaaacaccc    7620
agttgttcag gacaaataca cggaagccag ccgtgcttct tcctctccct cctgttcctc    7680
gttgccagat tctgctggct cagtctcaga attccacatc caagatatt caacatccct    7740 ccatccccac tgcgaccgcc tgggttcaag ccaccctcct atgtcgccgg atgaaagcaa    7800 cagccccac gtgggcctcc ctccctctct cttgcccaga ccacgttcca cgtggtagcc    7860
agggtgcttg taaaaatgta aatcaggctg ggtgtggtgg tggctcatgc ctgtaatccc    7920
agctctttgg gagggcgagg cgggcggatc acctgaggtc aggagttcga gaccagcctg    7980
gccaacatgg tgaaacccccg tctctaccaa acatacaaaa attagccagg caaggtggtg    8040
cacacctgta atctcagcta cttggggtgc tgaggcagga gaatcgctgg aacctgggag    8100
gcagaggttg cagtgagctg agatcatgcc actacactcc agcctgggtg acagagcgag    8160
actgtgtctc aaaaaacaaa caacaacaa aaacaaaact gcccagtggc ttcctactgt      8220
```

```
gctcagaatt aaatccaaat gcccatcacg ccctgcaggt ccccaaatga tccaattccc    8280
ccattagaaa gtaagttcag gaaaacagca attttgcttg ttttttttg ttttcttttt    8340 tttattttct tttccactgc tatgcccgca gggcctggca cacattaagt actcaattaa    8400
gcaacagccg aatgcacctg ctatcagat ggcctcgtgc tgggatgggg gggatgccta    8460
tgtcacctcc tgcctgacat ctataagaca ccctcagggt tcagtcgcat ctgctgttca    8520
tttacagtgt agactcacgg ttttttgcag tgggcagctg tgaggaccca cagtggatgg    8580
ataaggaccc caccacagag caagtggccc gaggtgtaga gggcagcttg gtagggtga    8640 gatgtcttgt cgcagggtcc gccatgcacc aacttattct gctcctctgc ccaggctgag    8700
ggagagaaga tctgagtcag agaggagttc tggagaaacc aagcgcatcc ccctcaacat    8760
gaactccagt caagattggt caggtgcagt ggcttatgcc tgtaatccca gctgaggcag    8820
gaggatcgct tgagcccagg agtttgagac cagcctcggt aacacagtga gacctcatct    8880
ccacacacac acacacacac acacacacac acacacacac aaattagcag ggtatggtgg    8940
catacgcctg tagtcccagc tacttgggag gctgaggtgg gaggtcact tgagacccaa    9000 gagttcaagt ctgcagtgaa ctatggatca tgccactaca ctccagcctg ggtgacagag    9060
tgagaccctg tctcaaaaaa aaaaagcttc tctgtatttc cactcccaaa cttaccccat    9120
tcccattaca aacccaactg tatccccat tcccgggctc tctccaactt tccaacctac    9180
ctcctacctc ttctatgttt agatccccat ccctaaagcc aaccccaccc caaaccctca    9240
tatcttcaaa cccacctccc accaccctcc ctatctgtat tccccaccct tagcctaatc    9300
cccaacgtct tcctcatttc aaagctcccc caccccaacc ctgtgcatat ccccatcccc    9360
aataccagcc tcttctccat caacaagccc aaccctgtct gcaagcctcc cccatccaaa    9420 tgcccttttcc ccacctgcag caatcagact cagcaccacc atcagcttct tcatggccgc    9480
tcctgagagg ggaagccaca tggtccatta gtcactgcct cgaccctccc cccatccctc    9540
tgtctgctcc ctctgcatcc tctccttcct tcctggcctg ctatggtctc ctgccttgac    9600
ctctgtcctt cccatctagc ctcctgattt attcttcctc agcccacatc ttccatcaga    9660
ggatcccacg aaaacagtgc caaagagaat tcagaactac gtccactggt ccagtaaccc    9720
atggtgagat tctgattaga tcttttctact ttcttgggca ctgatttgcc ttcctgtcga    9780
caggagaggg ttaccctagg gggccctagc gttcttcctc tgtatgggag ttttcctcgg    9840
agcctggctc tgtgcgcaat ggccacccac cccgcccacc cggcaggttc tgtgatgtct    9900
gtgatctcac ctgctgcagg cctccggggct ccggggattc ttgagtcggg ggaaggaaca    9960
gctttgagac gaggaggcag aaagagttag aaatgcgggg agccgtgagg agagaagaca    10020
ctcagatgca gtggcagagc caagcggagg acgcagggcc cgcagagccc agggctgcag    10080
ggactgccag acacacaccc ccagctccca ggcctccctg gaagaggctg ttctgtccc    10140 cagatgcttc tggaacgtcc tttaaccccc tgtctctcag gtccctgagc caggagactg    10200
gctacaccct tttcctcctt acccaggcct cccacacaca ttcctcccgc ccccacgctc    10260
tgctcttggt gaccctgac caggcctcca gggaagggag cactggtccc tgagtgcagt    10320
gagggcctgg actcctgggt ctgagggagg aggggcttgg gggcctggac tcctgagtct    10380
gagggaggag gggctggggg cctggaccct tgcgtctgag ggaggagggg cttggggcct    10440
ggactcctgg gtctgaggga ggaggtgaga acttggactc ctgggtctga gggaggaggg    10500 gctggggggcc tggactcctg agtctgaggg aggaggtggg aacttggact cctggtctg    10560 agggaggagg ggctaggacc taaactcctg gtctgaggg aggaggggct ggggcctgaa    10620
```

```
tctgaggcag aggaagttct agtcggctca gtccttagac ctccgggttt tggagaaaga   10680
aagtgtctga agacaaattc cggcctctgg ggcaagcaga tggtgcccca ggcctccctg   10740 caccccagc actctctgtg ccacccaggg acctgcaggc cctcactccg ggctctagag    10800
ccctccggca ctgggaagca gcctgcccag gttcagtgcg gttggggtga ctcacacacc   10860
tgcccgtagg tccctctgtg tgctgcctgc cgacctctgt gtcccagga gagagcgagc    10920 cagccagccg gggagacagc tacagcgtgt gtcaccacac tggcccccgc ccctgccccg   10980
ggctggggag caggcccagg cgcgatgggg aaagggccca ggaacaatcg ggctttgtcc   11040
gcc                                                                  11043

<210> SEQ ID NO 30
<211> LENGTH: 35634
<212> TYPE: DNA
<213> ORGANISM: Homo sapiens
<220> FEATURE:
<221> NAME/KEY: misc_feature
<222> LOCATION: (1)..(35634)
<223> OTHER INFORMATION: MUC2

<400> SEQUENCE: 30
caacccacac cgcccctgcc agccaccatg gggctgccac tagcccgcct ggcggctgtg     60
tgcctggccc tgtctttggc aggggggctcg gagctccaga caggtgagag agcagacaca   120
ggggtctggg gcctggcaga gtgtcctggg ggcagggcga ggcgggcggg caagtcgcgt    180 ctggaggag gagctggtcc cagagtgcag cctgcgcggc tctgctgagg ctcctggccc     240
gggttggtcc ctggaagccc ccggccctgc tgactttcaa ggagctggaa ggtcggggct   300
cccctgctat tcctttgggg ttgactgccc gacgacagtg tgggtcttgg ggccagcacc    360
aggtggaaac agcaggtcag gccccagtga actgggtcat tgtccatagg ggaggaaggg   420
gtggccagga tcccaccaga aggccccatt tcaggtggc agagacccctt gaagagttgg    480 ggcagcacag cccttgctgg ggagcggggt gcccagaatg ccctctccta catcccgctt   540
ggcacccggc cgcactcctc accaggccgg gggtagaagc cctgagaccc ctgtggtggg   600
gtgaccaagg cccagcagag ggcccgagga taggaaggaa cctttcccgg ccaggggccc   660
tgtgctgggc tcgaagctgc ttccaggtgc ttcttcaggg gccttctctc gagggtagct    720
tgggcagcct tcccctccg gggccactca cccctcattc ccgctgctc cctcagaggg      780 cagaacccga aaccacggcc acaacgtctg cagcacctgg ggcaacttcc actacaagac    840
cttcgacggg gacgtcttcc gcttccccgg ccctgcgac tacaacttcg cctccgactg     900
ccgaggctcc tacaaggaat tgctgtgca cctgaagcgg ggtccgggcc aggctgaggc    960
ccccgccggg gtggagtcca tcctgctgac catcaaggat gacaccatct acctcacccg    1020
ccacctggct gtgcttaacg gggccgtgtg agtgtggtcg gtggcacccc tcccacatcc   1080
tagcaacggg ggctgatgtt tcccaaaggg atattccttg tagccctaga agacccttc    1140 cgccccagca cacagctcag gagaacagcc ttgaggtttg ggttcaggtc actaattcat   1200
tcaacaaaca ctgatgagcc cccaccattc cccccatagg caaggggttt cagttatccc   1260
tttgcctgtg tgtccctgac agcccctccc ctcgagcccc accaggctcc ggacagactt   1320
ggcacccctg gaggctgcat gtctctggtc ctgtgcatgg agtggccgtg tgtgccctcc    1380
ccaggctaga gttacagaag ccggtgcagg gggctgtggg acccccttcc ccatcccag    1440 ctattgctcc cctattgtct ccagaacaat gaggccctgt aagtgcgttc ccatccagcg   1500
```

```
cctgcccctc ttctgcctgg ggatttagtt tcctgcaagg cgccccagca tgggcatggg    1560
caggcgggtg gaggccctca ggcatgggca tgggcaggcg ggtgggtaga ggccctcagg    1620
cgtgagtgcg ggcgggtggg tggatagaag ccgtcaggca tgggtgcagg cgggtgggta    1680
gaggtcctca ggtgtgggca tgggcaggtg ggtgggtaga ggccgtcagg tgtgggcgcg    1740
ggtgggtggg tagaggccct caggcatggg tgcaggcggg tgggtgggta gaggccctca    1800
ggcgtgggcg cgggtgggtg gatagaggcc gtcaggcgta ggtgcgggcg ggtgggtaga    1860
ggtcctcagg tgtgggcgca ggtgggtggg tgggtagagg ccctcaggca tggcacaggt    1920
gggtgggtag aggccctcag gcatgggcgc aggcgggtgg gtgggtaggg ccctcaggc    1980 atgggtgttg gcaggtgggt gggtagaggc tttcaggcat gggcaggcag gtagaggccc    2040
ttgaggaccg aggcacagag gctgggtgag tgcctctac ctggaccagc aaggggcact    2100
ggcaggaggt ggggtagggc ccctgacgtt ctcaggggca gcctgggggg ctctgggggg    2160
tttgggaccc catgggggga tgttccacca gcaggggggc ctggaagggg gctgggcagc    2220
ctggtcctcc ctcctctccc aacctggtgc cctcaggggcc tctgagggg gaccctgccc    2280 aggaccgtgc cccgaggagg gagtggagag gaggggcgtg caggcaggag gtggctctgc    2340
cggggaagcc cggccagcgg agatggacag gtgctctttg gccactgcct atgtccctcc    2400
accccagagg ccggccaagt tggtgatccc agggcaggag ctgggcctgg cagagccatc    2460
tccaccaccc caggtgccca gcttcagtcc cctctgggcg gcgggtccc gggaggacaa    2520 gctggggcgg gggggcctgg gtggtggacc caagagtgac cccgatgtgc ctccgccagg    2580
gtcagcaccc cgcactacag ccccgggctg ctcattgaga gagcgatgc ctacaccaaa     2640 gtctactccc gcgccggcct caccctcatg tggaaccggg aggatgcact catggtgctc    2700
aggggtcccc ggactcgtgg ggctggtggg ggctccgtca ggcctctggg cagaccccaa    2760
gggagggcag ggagggcagt gctctgaccc ctcaccgaga gggcatgggt ggggcagggc    2820
ctcggcagcg cagggcgtcg gtgctggact tgggggggcag cagcagaagc cgacctggcc    2880 ctgaccccc caggcctcag ccttcccca aacgcactcg gcttctcagg gacctgccct     2940
gccaggccgc tccctggctg ctgacccag ccttcctgcc ccaccttcct ctggctcaaa     3000
caagccacga gtcttggggg ttcctggcgg ctgtgggccg ggcgggaggc cagctcacct    3060
gctccctccc gcaacagctg gagctggaca ctaagttccg gaaccacacc tgtgccctct    3120
gcggggacta caacggcctg cagagctatt cagaattcct ctctgacggt gaggcccgga    3180
gggcttggag gggcagggt aggctacggg ccccccaggag ccctagctga agggccgtgc    3240
atccccaggc gtgctcttca gtcccctgga gtttgggaac atgcagaaga tcaaccagcc    3300
cgatgtggtg tgtgaggatc ccgaggagga ggtggccccc gcatcctgct ccgagcacgt    3360
gagtcccctc ggtccggggt ggggggtcctg gcggagctgg cctctgaata gcatgctcac    3420
cctgcgtctg tccccagcgc gccgagtgtg agaggctgct gaccgccgag gccttcgcgg    3480
actgtcagga cctggtgccg ctggagccgt atctgcgcgc ctgccagcag gaccgctgcc    3540
ggtgcccggg cggtgacacc tgcgtctgca gcaccgtggc cgagttctcc cgccagtgct    3600
cccacgccgg cggccggccc gggaactgga ggaccgccac gctctgccgt aagccccggc    3660
gccttgtggg cagggacccc caggagaccc ccacgctggt gctttcccca gcccgggtg    3720 ggagctgtgt ctgtgccggg caccttgagc tgggggaca ctcaccgcac cgggcacctt    3780
gagctggggg aacactaacc gtgccggggca ccggagctg ggggggacact caccgtgccg    3840 ggcaccttga gctggggga cactcaccgt gccgggcacc gggagctggg gggacactca    3900
```

```
ccacgggcac cgagagctgg ggggacactc accgtgccgg gcaccgggag ctgggggac      3960 actcaccgtg acgggcaccg ggagctgggg ggacactcac cgtgacgggc accgggagct    4020 gggggacac tcaccgtgcc gggcaccggg agctggggg acactcacca cgggcaccgg      4080
gagctggggg gacactcacc gtgccgggca ccttgagctg ggggggacact caccgtgccg   4140 ggcaccggga gctggggga cactcaccgt gccgggcacc gggagctggg ggacactca      4200 ccgcgccggg caccgggagc tgggggaca ctcaccgtgc cgggcaccgg gagctggggg    4260
gacactcacc acgggcaccg agagctgggg ggacactcac cgcgccgggc accgggagct    4320 gggggacac tcactgtgac gggcaccggg agctgggggg acactcaccg tgccgggcac    4380
cgggagctgg ggggacactc accacgggca ctgggagctg ggggacact cactgagggc    4440 accgggagct ggggggacac tcactgtgac gggcaccgag agctgggggg acactcactg   4500
tgacgggcac cgggagctgg ggggacactc actgtgacgg gcaccgggag ctgggggac    4560 actcaccgtg ccgggcaccg ggagctgggg ggacactcac tgagggcacc gggagctggg   4620
gggacactca ccgtgccggg caccgggagc tgggggaca ctcaccacgg gcaccgggag    4680 ctgggggac actcaccgtg ccgggcaccg ggagctgggg ggacactcac cgtgccgggc    4740
accgggagct ggggggacac tcactgaggg caccgggagc tgggggaca ctcactgtga   4800 cgggcaccga gagctggggg gacactcact gtgacgggca ccgggagctg ggggacact    4860 cactgtgacg ggcaccggga gctggggga cactcaccgt gccgggcacc gggagctggg    4920
gggacactca ctgagggcac cgggagctgg ggggacactc accgcgccgg gcaccgggag   4980 ctgggggac actcactgag ggcaccgaga gctgggggga cactcactgt gacgggcacc   5040
gggagctggg gggacactca ccgcgccggg caccgggagc tgggggaca ctcaccgtga    5100 cgggcaccga gagctggggg gacactcact gtgacgggca ccttgagctg ggggacact    5160 caccacgggc actgggagct ggggggacac tcaccgcgcc gggcaccggg agctgggggg   5220
acactcactg agggcaccgg gagctggggg gacactcacc gtgccgggca ccgggagctg   5280 ggggacact cactgagggc accgggagct ggggggacac tcactgaggg caccgggagc   5340 tgggggaca ctcactgagg gcaccaagag ctggggggac actcaccacg gcaccgaga    5400 gctggggga cactcaccgt gacgggcacc gggagctggg gggacactca ccacgggcac    5460
cgggagctgg ggggacactc accgtgacgg gcaccggag ctgggggac actcactgag    5520 ggcaccggga gctggggga cactcaccac gggcaccggg agctggggg acactcaccg    5580 cgccgggcac cgggagctgg ggggacactc accacgggca ctgggagctg ggggacact    5640 caccacgggc actgggagct ggggggacac tcaccacggg caccgggagc tgggggaca    5700 ctcaccgtga cgggcaccgg gagctggggg gacactcacc acgggcaccg ggagctgggg   5760
ggacactcac cacgggcacc gggagctggg gggacactca ccacgggcac cgggagctgg   5820
ggggacactc accgcgggca ctgggagctg ggggacact caccacgggc actgggagct    5880 gggggacac tcaccacggg caccgggagc tgggggaca ctcaccgtga cgggcaccgg    5940
gagctggggg gacactcacc acgggcaccg ggagctgggg gacactcac cacgggcacc   6000 gggagctggg gggacactca ccacgggcac cgggagctgg ggggacactc accgtgccgg   6060
gcaccgggag ctgggggac actcactgag gcaccgggga gctggggga cactcaccac   6120 gggcaccgag agctgggggg acactcactg tgccgggcac cgggagctgg ggggacactc   6180
accacgggca ccgggagctg ggggacact caccgtgacg gcaccgggga gctggggga    6240
```

```
cactcaccac gggcaccggg agctgggggg acactcaccg tgccgggcac cgggagctgg    6300
ggggacactc actgagggca ccgggagctg ggggacact caccacgggc accgagagct    6360
gggggggacac tcactgtgcc gggcaccggg agctggggg acactcacca cgggcaccgg    6420
gagctggggg gacactcacc gtgacgggca ccgggagctg ggggacact cactgagggc    6480
accgggagct gggggggacac tcaccacggg caccgggagc tgggggaca ctcaccacgg    6540
gcaccgggag ctggggggac actcaccgtg ccggcaccg ggagctgggg ggacactcac    6600
cacgggcacc gggagctggg gggacactca ccacgggcac cgggagctgg ggggacactc    6660
accgcgccgg gcaccgggag ctgggggac actcaccgtg gctgagagc ccttctcggt    6720
gcacttcggg gtggagcggc tgctgtgccc cagcctcacc ctcactgcgt ggcctctgcg    6780
gttccagcca agacctgccc cgggaacctg gtgtacctgg agagcggctc gccctgcatg    6840
gacacctgct cacacctgga ggtgagcagc ctgtgcgagg agcaccgcat ggacggctgt    6900
ttctgcccag aaggtgcgtg tggaggatgg ccccgccctg gcactgccca ccagatgaga    6960
ggcagccctg gcctggggtt ctcgcctgcg ctgagggac ggctccgctg ggtggtgggg    7020
gcagcggcgg cacagaagtg cctctccctc cacccgatac cggggagaa ggggcctcgg    7080
tgtgaggccc ttcccaaagg gtggcttcag ggaggccggg aagggggctg ccttcctggt    7140
tatcaccctg gggacagacc tcctcctgcc cggcccctgg cctggtgcct gaggcctttg    7200
ggagcagctc gattgtcagg ggcaggaagg tggcctggag gctggacccc catggccaga    7260
ccccaaccca gggaccaggt ggggaccgca ggcgtcagca caggggacca gtggtgcctg    7320
cgggtgggag gcctggctgg cagccccctcg gtggggattc tggctctttc tgagccagcc    7380
ggggtgacat cgcctccctg gctgtcccag gcaccgtata tgacgacatc ggggacagtg    7440
gctgcgttcc tgtgagccag tgccactgca ggctgcacgg acacctgtac acaccggggcc    7500
aggagatcac caatgactgc gagcagtggt gagtcccggg gccagggctg ggcacagcag    7560
aggctggggc ggctgagccc tgaccctgtg ccccgctgcc caacagtgtc tgtaacgctg    7620
gccgctgggt gtgcaaagac ctgccctgcc ccggcacctg tgccctggaa ggcggctccc    7680
acatcaccac cttcgatggg aagacgtaca ccttccacgg ggactgctac tatgtcctgg    7740
ccaaggtagg ctgcccaggg tctgggcat ggggcagagc tggggctggc atccaggccc    7800
ttggctgtcc cggggtgggt gggctggctg tccctgaagc agagggtgcc tgtgggctgt    7860
cctggggcag gtgaccatgc ttctgctctc tggctggaga ataagaagca ggccttcctt    7920
tctaagccac tgccgggtcc tagggtgcag ggtgctgccc gtcccggccc tcagcagctg    7980
cactgcctct tgccccatca cagggtgacc acaacgattc ctacgctctc ctgggcgagc    8040
tggcccctg tggctccaca gacaagcaga cctgcctgaa gacggtggtg ctgctggctg    8100
acaagaagaa gaatgtgagt ggtcctgccc cctccttctg gagccccagg tccccgagg    8160
ggggcccttc tcagccctga gcaacctcgg ccttccctgc aggtggtggt cttcaagtcc    8220
gatggcagtg tactgctcaa cgagctgcag gtgaacctgc ccacgtgac cggtgagttg    8280
cgccccaggg aggggcccgg gcccttcgag ctccactggg cctgcagtga ttcggacagt    8340
ccagccacct cggacccagg aggctgggtg gaaggttcc acgggggag gtccctgcg    8400
gcacccagca ggctccgtcc tgggtcctct gctggagggg gtggtgggag ggtgacaccc    8460
tcccgctgct cacctgggcc aggcaggtcc cgggagccc gccctcgcc atgcccctta    8520
ccgtgtccct catcgtgccc ctgcccacag cgagcttctc tgtcttccgc ccgtcttcct    8580
accacatcat ggtgagcatg gccattggcg tccggctgca ggtgcagctg gccccagtca    8640
```

```
tgcaactctt tgtgacactg gaccaggcct cccaggggca ggtgcagggt aagtggcccc    8700
accggggttg ccccaacaaa ggcccacagg ggggcctgct agcccagac tcttcccaac     8760
cctgtcctgg cccctcaggc ctctgcggga acttcaacgg cctggaaggt gacgacttca    8820
agacggccag cgggctggtg gaggccacgg gggccggctt tgccaacacc tggaaggcac    8880
agtcaacctg ccatgacaag ctggactggt tggacgatcc ctgctccctg aacatcgaga    8940
gcggtgaggc tcggcaacac gggcgccccc acctagcgtg cctagggtac ccggcccatg    9000
gcctggaagg gcagacgggg ctcccagcag gaagcatggg tggtgagggg cagaagtgag    9060
gtggctctcc tccaggggca gcccggcccc tgctgcttcc tgctgtgggct agtttatggc   9120
ggccatggtg gcagcctgcc aggtgacctg gaagagggcc tgggctggtc cctacctgcc    9180
ccgtcatgtc caggatgctg ggcccttggg ggtgagagac gggaggtggt gggtgccctg    9240
caggggtttc tatctagcca ggagctgcct ggaaatttga ctcacgggga ggaaggggcc    9300
tgggcatcgg tgcacagagg gaaccatatc tggggcctag gcagccaggc agcagggccc    9360
aggggatctc acggggtcc cgggccccgc tgaagttccg atcccccact ccccagccaa     9420
ctacgccgag cactggtgct ccctcctgaa aagacagag ccccctttg gcaggtgcca      9480
ctcggctgtg gaccctgctg agtattacaa ggtgggtggg acccacaccc ccaggccccc    9540
atgccatcaa ggtggactca gggcaccccc agcccccat gccacccgtg aggtggactc      9600
agagcacccg gttgggccca ctggttgctg tgtgtgcgtg tgagcttgcg tctgtgagcg    9660
ccaggccaca ctctgcctcc ctgcctcact gcccgtccac cttgctctgt cgcccagagg    9720
tgcaaatatg acacgtgtaa ctgtcagaac aatgaggact gcctgtgcgc cgccctgtcc    9780
tcctacgcgc gcgcctgcac cgccaagggc gtcatgctgt ggggctggcg ggagcatgtc    9840
tgcagtgagt gccgtccccg tgggctgcat cctggggatg gggtccgggc tttgagctcc    9900
tgggacgggg ctgggggccc tgagcacggg tggtccaggg agaggggttg gccccctgca    9960
gccacggacc aggctccagc ttcgtcggcc ggtggtagca ggaaaccagc aactcctata   10020
gcaaggggcg gccacgtagc aggggcagaa cctggggtgg gcctgagct gtggcggccg    10080
agtgtgggag tgggtcccag agtgtgcact ccctggcccc ctggccaccc tggggatggg   10140
agctgggcgt ctggctcttc ccgtccctca caccaccccg tggtcctctg cagacaagga   10200
tgtgggctcc tgcccaact cgcaggtctt cctgtacaac ctgaccacct gccagcagac    10260
ctgccgctcc ctctccgagg ccgacagcca ctgtctcgag ggctttgcgc ctgtggacgg   10320
ctgcggctgc cctgaccaca ccttcctgga cgagaagggc cgctgcgtac ccctggccaa   10380
gtgctcctgt taccaccgcg gtctctacct ggaggcgggg gacgtggtcg tcaggcagga   10440
agaacgatgg tgggtacctg ctcggggggtc aggtgtggcg tgggggcggg ggaactcctt   10500
ctgaacctgc cccaagcgga gacctgggag tctctacctg gggaagctga gacacccaag   10560
gctgagggggt gcctggggtg gggggcgctg agaggcatca ggctcacatc tgcggggaag   10620
ctgctggctg tctgtggccg tcctgcatgg gccccgctca tccctggcct tttccacagt   10680
gtgtgccggg atgggcggct gcactgtagg cagatccggc tgatcggcca gagtaagtgg   10740
cactgccccg gccacccctc cccagccacc cctccctgcc tgccctggcc acctccccg    10800
gccacccctc ccgggcctgc ctgagaccct cagcttcagc tggagctgag gtggccctc    10860
cgtcccacag gctgcacggc cccaaagatc cacatggact gcagcaacct gactgcactg    10920
gccacctcga agccccgagc cctcagctgc cagacgctgg ccgccggcta tgtgcgtgtt   10980
```

```
gggggcgctg ctgtgggcgg gcagggattc ctggctggct gagcctggct cttgtgctgt    11040
gcccccgcta gggtctgggt gccgagtcct gaggacgcag gccctgttga tgctgtccct    11100
ggccctggga gggaagtggc agcctgtgag ccactggggc acaggggcca gtgtagggcc    11160
cttggccggc agccctcacc agtctcactg ccctgtggcg ggcccaaggg gagggaagcc    11220
tgagcccagg ccagggggag tggtgggagg tctgggacat gacagagact gcatggtcag    11280
gcctttcctg gttgcacatc aatcctgac cccaggagg ctgcagcct cacctgtcca    11340 cccctgaacc ccactctctg ctgtcccca gtaccacaca gagtgtgtca gtggctgtgt    11400
gtgccccgac gggctgatgg atgacggccg gggtggctgc gtggtggaga aggaatgccc    11460
ttgcgtccat aacaacgacc tgtattcttc cggcgccaag atcaaggtgg actgcaatac    11520
ctggtaagct ggcccggcct gtcctggctg cctcccaggc ccacgtgct ccgcaggggt    11580 ggccactgga gagcggtcca aggggcaagt gcctctcctg ggggttccgc ctgggtcttg    11640
cgagatcctg tggtggcccc tgtcccacgg gcagggtggt ctctcatgtc aaccgctggt    11700
cttgaagcca tggggaagg gacatttgga gccacttttg gggcctgcag gtgtcctgtg    11760
tgggaggcac agggagctgt ctgcacggtg cccagggtct cctccagcca cccatgagca    11820
ggtcctgggt cccttcaggc tcctctcctg tcctcctcag cacctgcaag agaggacgct    11880
gggtgtgcac ccaggctgtg tgccatggca cctgctccat ttacgggagt ggccactaca    11940
tcacctttga cgggaagtac tacgactttg acggacactg ctcctacgtg ctgttcagg    12000 tgtggtcacg ggcactgcct ggtcgggctg cttatggtca gggaccctct gcctgcccca    12060
agtgcagtgc ttagctcccc gagaaaccct gagacttggg aaggccggcc tttcctcagc    12120
cccagacccg cacctgcacc cgcaggagga ttcgttcttc tagccagggc tgggtagggg    12180
tggtaaaacc cctctgtact gcccagttct gtggttctcc tctgggtcct cctccgggtc    12240
ctcctccggg tcctcatctg gtcctccct cctctggcct cctctgggtc ctccctcctc    12300
tgggtcctcc tctgggtcct ccctcctctg gcctcctctg gtcctccct cctctgggtc    12360 ctccctcctc tgggtcctcc tccaggtcct cctctgggtc ctccctcctc tgggtcctcc    12420
ctcctctggg tcctcctcca ggtcctcctc tgggtcctcc ctcctctggg tcctcctctg    12480
ggtcctcctc tgagtcctcc ctcctctggg tcctcctcta ggtcctcctc tgtggtcctc    12540
atttgggtcc tcctctgggt cctcctctgg gtccttctct gggtgcacaa ggtgggtgca    12600
ccagccatgg ggactgaggg cacctgtttg gggagctgag taaaggccag ggctaggccg    12660
ctgcccgcgc ggctctccag atccaaatcc cacagccctt tgaggcaccg tgatccccag    12720
ggacagggga caggcctgca gcagggtcag gtccttggat gggccaggcc agggcctggt    12780
ttgtctgctc agtggctgtg accctgccaa ctggggcggg tgtgcccggg acacctggg    12840 gtccagctgt cctggctgac cttgccctcc tggccccag gactactgcg ccagaactc    12900 ctcactgggc tcattcagca tcatcaccga gaacgtcccc tgtggcacta cgggcgtcac    12960
ctgctccaag gccatcaaga tcttcatggg ggtgagtgct gctggccctg ggacgcgtg    13020 agccctgcgg gaccctcaga ccagccagtg actgggcctc tcctccgggc agaggacgga    13080
gctgaagttg gaagacaagc accgtgtggt gatccagcgt gatgagggtc accgtggc    13140 ctacaccacg cgggaggtgg gccagtacct ggtggtggag tccagcacgg gcatcatcgt    13200
catctgggac aagaggacca ccgtgttcat caagctggct ccctcctaca aggtgggctg    13260
cctccctgcc tgccctgccc cctcctggcc agccccccac cccctgccct ggtgtttgca    13320
ggacaagccc ctgtcctccc tccagcccct ttttggagcc cctgtgatgc ttgtctcttg    13380
```

```
cagggcaccg tgtgtggcct gtgtgggaac tttgaccacc gctccaacaa cgacttcacc    13440
acgcgggacc acatggtggt gagcagcgag ctggacttcg ggaacagctg gaaggaggcc    13500
cccacctgcc cagatgtgag caccaacccc gagccctgca gcctgaaccc gcaccgccgc    13560
tcctgggccg agaagcagtg cagcatcctc aaaagcagcg tgttcagcat ctgccacagc    13620
aaggtgggct ggccgggcca tggtggggca gtaggcaga ggagggctgt aggtgggctg    13680
tgactgtggg ctggggccat gggcgggcc gactgtaggc agagcagggc tgtaggggc    13740 ctgtgactat aggccggggc atggcggggc taactaggca gagcagggct gtaggtgggc    13800
tacagctgtg ggcggggcca tgggcgggc cgactaagca gagcagggct gtaggtgggc    13860
tatagctgtg ggcggggcca cgggcgggc cgactgtagg cagagcaggg ctgtaggtgg    13920
actatagctg tgggcgggc catggcggg gccgactgta ggcagagcag gctgtaggt    13980 gggctgtggc tgtgggcggg gccgactagg cagagcgggg ctatgggctg actgtggacg    14040
tggtgagggt gccgtagagc atgctaatga ccagggcgtg gtcatagcag ggtagggtct    14100
tgggtgctcc tggggctggg gggcttctcc acatgctccc cacaccttca ggagtcgccc    14160
tgctgcgtca cgcaccacac ggcgcttgtc ctccagcttt ggctctggcc gctgcctcct    14220
ttggtcacat gaccgtataa tcggcctccc ctctgagacc ctgggctgga ccccggcct    14280 ccctctgcct ccccaggctc agatattcac ccggagggag aaaggacatg tgtccccat    14340 gcccacacat ccccagctac aggcagctgg ggaggacggg ttctaggatg gccatgttac    14400
agctgaggat gcagagggt tgggtgatgg gtctgcacag ccacggcggg acaggtgtct    14460
ctggaccctc tccccaaggt tggccctgcc ggggccctgg ctggctggtg ctgggtaatg    14520
tgccctgtcc caggagcagg gccggcctca gggtcctgag ctccagggca ctggggaagt    14580
cctggctcca tgagggcagc acgggcccag gacagaccag ggtgttctcc ccaggtggac    14640
cccaagccct tctacgaggc ctgtgtgcac gactcgtgct cctgtgacac gggtggggac    14700
tgtgagtgct tctgctctgc cgtggcctcc tacgcccagg agtgtaccaa agaggggcc    14760 tgcgtgttct ggaggacgcc ggacctgtgc cgtaagagcc tgcccgaact gcactcaggg    14820
ccgggacggg ggctgggagg tgctgtattg cgggccgggg tgacactcct tgtccatcca    14880
ggtgatgggt gtgcatcacc caccctttcc ccgacttctc cagtgtcctt ctttggggcc    14940
ctgtgggacc cgggttggca gagcaagctt gatgcgtctg cgtcccagcc ccgaccca    15000 gattcgccct caccccggcc caggcctgag ccctcctgcg tctgaccctg gcctgtctc    15060 ccccaagcca tattctgcga ctactacaac cctccgcatg agtgtgagtg gcactatgag    15120
ccatgtggga accggagctt cgagacctgc aggaccatca atggcatcca ctccaacatc    15180
tccgtgtcct acctggaggg tgagcagggt ggggcgggct tcagcggggg tgatggccga    15240
ggggcctgga ggctgagtgg ggcagccctc gggagaggca acagtccact ggcctggagg    15300
gtgagccagg cggccctcgg gggaggctac ggccgacggg cctggcactg tggggctgaa    15360
ggctgatgtc tggagaccca tggggacacc cggagggagg cctgaccctc agggtaccca    15420
cagcccaggg cagccaggct ccccttgctg caggatcagg agggaagcag gctatcgtgg    15480
aaactgggag tggcaggggt ggaggtgct gaggttcgtg cagagcaggg cgggttgggg    15540
agcatttcag gcacaggtca ggggaggcc ctgccgggtg ctggtgtctg agctgagaac    15600
cagtgacgtg aaggagggac tggtgggaag tttgggagga gtatcccgcc atgggagagg    15660
aacatgggtc ttgggactca gggctgctcg gggggcccga tgagactggg cagggctcct    15720
```

```
cagcaggcag cgttcagggc tcagtggggt ggggagatcc aggccctgcc tttccaatcc    15780
ccggccttcc cagaggggca tcctgcagag aagggcctgc cagggtaggg acggtgggtg    15840
gggtgtggtg gactgcggtg gtcccaaccc tatgccctgt gtccaccagg ctgctacccc    15900
cggtgcccca aggacaggcc catctatgag gaggatctga agaagtgtgt cactgcagac    15960
aagtgtggct gctatgtcga ggacacccac tacccacctg gagcatcggt tcccaccgag    16020
gagacctgca agtcctggta cctaagccca cgtggcaggg ggcctggggg agctgcacat    16080
atgggcacat gagtacacac acacgtgtga gcacacagtg tacacagtac acagacacac    16140
aaccgttcca catgggtgca catgcacaca aacgcacaca gcataccacg tgcatacaca    16200
cggtcacatg catgcatggt gcacacatgc acacatgaat ggatgccaac atgcaggcac    16260
acacagtcac acatgcacac agcgcacaca tggacacatg cctagacgca gatacccagg    16320
catacactca cggttacaca ctcacgcaca tatgcatgga tgcagacacg caggcacaca    16380
cggtcatata gtcatacacc acatgcacac atgcacagac acccaggcac acacagttac    16440
acagtcacac atgcacacat gcatggacgc agacacgcag gtgcacacac acatgcacag    16500
tgcacacatg tacacatgcc tagacacaga tacccaggca cacacagtca cacatgcatg    16560
gacacagagt cacatgtgta cacatacaca cgtgtggaca gacataggca cagtcacgtg    16620
cacacatgca ctcacactca gtcacacatg aacatgtgct cacatgcatg gacactgaca    16680
cgcaaggaca cacagtcaca catgcacaca tgcatagaca cagacaccca ggcacacaca    16740
gttacacagt cacacatgca tggatgcaga cacgcagtca cacagtcaca catgcacaca    16800
ctgcacacat gtacacatgc ctagacacag atatgcaggc acacacacat agtcaaacat    16860
gcacacatgc atggacacaa agtcacacgt gcacacatgc acacatgcat ggacagacac    16920
aggcacacac agtcacgtgc acagatgcac tcacagtcac acatgaacac atgctcacat    16980
gcacagacac tgacacgcag gcacacacag tcacacatgt acacgtgcct agacacagat    17040
acccagacac acacaattac acagtcgcac agtcacacat gcatggatgc agacacacag    17100
gtacacaagg tcacacagtc atataatgca cacatgcaca catgcataga tacagacacc    17160
caggtacaca ctcacggtga cacagtcaca catgcacaca tgcatggagg cagacacaca    17220
agcacacaca gtcacacagt cacacatgca cacaggagcc aggctacaga ggtaccagtc    17280
cctcactgcg gcgggggggtc ttctgttctc atcccatcct ctgggtctgg ctttttcctt    17340
cctctcctcg cccctgctct gttcccacag ttacaaccca gtgggggggct cttccggagc    17400 tggctttggg gcagtgcctg ggggcttttgg gctcggtact agccacatgg ggaagctggg    17460
ggtctgagca gcgtgggcgc gttgtcagtg gagtgggact tgtagccatg tgcttgcttt    17520
gcagcgtgtg taccaactcc tcccaagtcg tctgcaggcc ggaggaaggt aagctgccct    17580
ctgctgccag ccctgcggtg gccgggccca tcctggggaa gcctgtgggg ccttggatcg    17640 gtgggggtg ctggtctcct cctggctct gccccttttgg tccccccca gctcagaccc    17700 acctccgatg tgtatcagcc ctgggggct gctgtgaccc atttttgtttc ttctggggtg    17760 tcggtgtcct gtggggaatt tccgtcaccc tctcccgtga tccagcttct gcgttctgat    17820
gagattccct ttattcaaag agaggggctc tgggacgggt gcagtctcac tggagcattt    17880
cttagctgct tgtggggggct cgggcacacc tggccttctt cctatcttgc tcctgatgag    17940
gtgattcttg gcctcaccct caccccccagg aaagattctt aaccagaccc aggatggcgc    18000
cttctgctac tgggagatct gtggcccccaa cgggacggtg gagaagcact tcaacatctg    18060
ttccattacg acacgcccgt ccaccctgac caccttcacc accatcaccc tccccaccac    18120
```

```
ccccaccacc ttcaccacta ccaccaccac caccaccccg acctccagca caggtaaggc    18180
cccctggttc cctccatgct tcctcgggct ctcaccttcc cctgcatcca gcatccagca    18240
cagagggctc tttcgggggc aggccccggc ctggtgcagc caggctgtga ccctgcaca    18300 ccagctgcag agtgaggtga cagtggcatt cctctgcact gaggtgtgag ggggcctgcc    18360
ctggctcccc tggcctggtg cattgagata gtagcatcct gaccacatcc ccaagcccag    18420
accacagtgg aggatcacct ggggagattt ctgaaaacca gcaggaaact atccctaagg    18480
gttagagaaa ttttcttatg ttcccctgcg tttgttctgg ttgaaatcct agctaccact    18540
gaacaagcca ccaggggtat gatagccaca gaaaaaagaa acttttttta aaaaaggcaa    18600
gattttaaaa gatcttgaac tatataatga tatcctcttt tcttcctgct ttattgcagt    18660
tttatcaaca actccgagta agtgacggtg atgatattca tgatgacaag cagggtggga    18720
ggagcgaagt cttataaaat cacctgcagg atgcttcctt cagggcccag atgtgaggct    18780 ggcgggctg gactcctctg cttatggacc aaagatggat gtattttggc cacttcattc    18840
atggtttgct gaggccaggg gctaaagtga gacctgattg gctgtcggtg acaatattgc    18900
tggttaagag tggagacaaa gccccttccg tcacacttcc ttactggaat gggaagctct    18960
cttgttattg attctttgaa aaaaaagtat tgaaaatagc tgaggaaagg gtccatcaca    19020
cccaggtgtg gccctgggtg gccccgtctc tttgggctca ggttttcagt tgcaaaatga    19080
ggatggaagt ggtgtccagc cctgagctct ctggccctgc actctggttt tttggcaatg    19140
acagggaaaa gagagattgc agctggggga tggtcatgga ggtccctggg tcctctgaat    19200
cctggtggct tcctggaggt gcctctcccc aggtgtgaga gacaagaact tggttttgct    19260
tccctagagc tgtgctgcct ctggtctgac tggatcaatg aggaccaccc cagcagtggc    19320
agcgacgacg gtgaccgaga acatttgat ggggtctgcg gggcccctga ggacatcgag    19380
tgcaggtcgg tcaaggatcc ccacctcagc ttggagcagc taggccagaa ggtgcagtgt    19440
gatgtctctg ttgggttcat ttgcaagaat gaagaccagt ttggaaatgg accatttgga    19500
ctgtgttacg actacaagat acgtgtcaat tgttgctggc ccatggataa gtgtatcacc    19560
actcccagcc ctccaactac cactcccagc cctccaccaa ccagcacgac cacccttcca    19620
ccaaccacca cccccagccc tccaaccacc accacaacca cccctccacc aaccaccacc    19680
cccagccctc caataaccac cacgaccacc cctccaccaa ccaccactcc cagccctcca    19740
ataagcacca caaccacccc tccaccaacc accactccca gccctccaac caccactccc    19800
agccctccaa ccaccactcc cagccctcca acaaccacca caaccacccc tccaccaacc    19860
accactccca gccctccaac gactacgccc atcactccac cagccagcac taccacccttt    19920 ccaccaacca ccactcccag ccctccaaca accaccacaa ccacccctcc accaaccacc    19980
actcccagtc ctccaacgac tacgcccatc actccaccaa ccagcactac tacccttcca    20040
ccaaccacca ctcccagccc tccaccaacc accacaacca ccccctccacc aaccaccact    20100 cccagccctc caacaaccac cactcccagt cctccaacaa tcaccacaac caccccctcca    20160 ccaaccacca ctcccagccc tccaacaacc accacgacca cccttccacc aaccaccact    20220
tccagccctc taacaactac tcctctacct ccatcaataa ctcctcctac attttcacca    20280
ttctcaacga caacccctac taccccatgc gtgcctctct gcaattggac tggctggctg    20340
gattctggaa aacccaactt tcacaaacca ggtggagaca cagaattgat tggagacgtc    20400
tgtggaccag gctgggcagc taacatctct tgcagagcca ccatgtatcc tgatgttccc    20460
```

```
attggacagc ttggacaaac agtggtgtgt gatgtctctg tggggctgat atgcaaaaat   20520
gaagaccaaa agccaggtgg ggtcatccct atggccttct gcctcaacta cgagatcaac   20580
gttcagtgct gtgagtgtgt cacccaaccc accaccatga caaccaccac cacagagaac   20640
ccaactccga caccaatcac caccaccact acggtgaccc caaccccaac acccaccagc   20700
acacagagta caacaccaac acccatcacc accaccaata cggtaacccc aaccccaacc   20760
cccactggca cacagacccc aaccccgaca cccatcacca ccaccaccac tatggtgacc   20820
ccaacaccaa caatcaccag cacacagacc caaccccga cacccatcac caccactacg   20880
gtgaccccaa ccccaacacc caccagcaca cagagaacaa caccgacatc catcaccacc   20940
accaccacgg tgaccccaac cccaacaccc accggcacac agaccccaac cacgacaccc   21000
atcaccacca ccaccacggt gaccccaacc ccaacaccca ccggcacaca gaccccaaca   21060
acgacaccca tcaccaccac caccatggtg accccaaccc caacacccac tggaacacag   21120
acccaaaccc caacacccat caccaccacc actacggtga ccccaaccc tacccccacc   21180
ggcacacaga ccccaacatc gacacccatc agcaccacca ctacggtgac cccaacacca   21240
acacccaccg gcacacagac cccaaccctg acacccatca ccaccaccac tacggtgacc   21300
ccaaccccaa cacccaccgg cacacagacc caaccacga cacccatcac caccaccact   21360
acggtgaccc caaccccaac acccaccggc acaaagagta caaccccgac atccatcacc   21420
accaccacta tggtgacccc aaccccacca cccactggca cacagacccc aaccacgaca   21480
cccatcacca ccaccactac ggtgaccca accccaacac ccaccggcac acagaccca   21540
accccgacac catcaccacc accaccacg gtgaccccaa ccccaacacc caccggcaca   21600
cagaccccaa catcgacacc catcaccacc aacactacgg tgaccccaac cccaacacca   21660
accggcacac cgagtacaac cctgacaccc atcaccacca ccactatggt gaccccaacc   21720
ccaacacca ccggcacaca gaccccaaca tcgacaccca tcagcaccac cactacggtg   21780
accccaacct caacacccac cggcacacag accccaaccc cgacacccat ctccaccacc   21840
actacggtga ccccaacccc gacacccatc tccaccacca ctacagtgac cccaaccca   21900
acacccaccg gcacacagac cccaaccatg acacccatca ccaccaccac cacggtgacc   21960
ccaaccccaa acacccaccgg cacacagacc ccaacaacga cacccatcag caccaccacc   22020
acagtgaccc caaccccaac acccaccggc acacagaccc caacatcgac acccatcacc   22080
accaccacta cggtgacccc aaccccaaca cccaccggca cacagacccc aaccacgaca   22140
cccatcacca ccaccaccac ggtgacccca accccaacac ccaccggcac acagagtaca   22200
accctgacac catcaccacc accaccacg gtgacaccaa ccccaacacc caccggcaca   22260
cagaccccaa ccccgacacc catctccacc accactacgg tgaccccaac ccaacacccc   22320
accggcacac agacccaac cacgacaccc atcaccacca ccaccgggt gaccccaacc   22380
ccaacaccca ccggcacaca gaccccaaca cgacaccca tcagcaccac caccacggtg   22440
accccaaccc caacacccac cggcacacag accccaacat cgacacccat caccaccacc   22500
actacggtga ccccaaccc aacacccacc ggcacacaga ccccaaccac gacacccatc   22560
accaccacca ccacggtgac cccaaccca acacccactg gcacacaggc ccaaccccca   22620
acagccatca ccaccaccac tacggtgacc ccaaccccaa cacccaccgg cacacagacc   22680
ccaacaacga cacccatcac caccaccacc atggtgaccc caaccccaac acccaccggc   22740
acacagaccc caacatcgac acccatcacc accaccacta cggtgacccc aaccccaaca   22800
cccaccggca cacagacccc aaccccgaca cccatctcca ccaccactac ggtgacccca   22860
```

```
accccaacac ccaccggcac acagacccca accatgacac ccatcaccac caccaccacg    22920
gtgaccccaa ccccaacacc caccggcaca cagaccccaa caacgacacc catcagcacc    22980
accaccacgg tgaccccaac cccaacaccc accggcacac agaccccaac atcgacaccc    23040
atcaccacca ccactacggt gaccccaacc ccaacaccca ccggcacaca gaccccaacc    23100
ccgacaccca tcaccaccac caccacggtg accccaaccc caacacccac cggcacacag    23160
accccaacat cgacacccat caccaccacc actacggtga ccccaacccc aacacccacc    23220
ggcacacaga ccccaaccac gacacccatc accaccacca ccacggtgac cccaacccca    23280
acacccaccg gcacacagag tacaaccctg acccccatca ccaccaccac cacggtgaac    23340
accaaccccc aacacccacc ggcacacaaa accccaacat caacacccat caccacccac    23400
cactacggtt gaccccaacc cccaaaaccc accggcacac agaccccaac cccaacaccc    23460
attctccacc accaataacg ggtgacccca accccaacaa cccaccggca cacagacccc    23520
aaccatgaca cccatcacca ccaccaccac ggtgacccca accccaacac ccaccggcac    23580
acagacccca acatcgacac ccatcaccac caccactacg gtgaccccaa ccccaacacc    23640
caccggcaca cagaccccaa ccatgacacc catcaccacc accacggt gaccccaac    23700
cccaacaccc actggcacac aggccccaac cccaacagcc atcaccacca ccactacggt    23760
gaccccaacc ccaacacccac ccggcacaca gaccccaacc acgacaccca tcaccaccac    23820
caccacggtg accccaaccc caacacccac cggcacacag agtacaaccc tgacacccat    23880
caccaccacc accacggtga caccaacccc aacacccacc ggcacacaga ccccaacccc    23940
gacacccatc tccaccacca ctacggtgac cccaacccca cacccaccg gcacacagac    24000
cccaaccatg acacccatca ccaccaccac acggtgacc ccaacccaa cacccaccgg    24060
cacacagacc ccaacaacga cacccatcag caccaccacc acggtgaccc caaccccaac    24120
acccaccggc acacagaccc caacatcgac acccatcacc accaccacta cggtgacccc    24180
aaccccaaca cccaccggca cacagacccc aaccacgaca cccatcacca ccaccaccac    24240
ggtgaccccca accccaacac ccactggcac acaggcccca accccaacag ccatcaccac    24300
caccagtacg gtgaccccaa ccccaacacc caccggcaca cagaccccaa ccacgacacc    24360
catcaccacc accactacgg tgacaccaac cccaacaccc accggcacac agtccccaac    24420
cccaacagcc atcaccacca ccactacggt gaccccaacc ccaacaccca ccggcacaca    24480
gaccccaaca ttgacgccca tcaccaccac cactacggtg accccaaccc caacacccac    24540
cggcacacag accccaaccc cgacacccat ctccaccacc actacggtga ccccaacccc    24600
aacacccacc ggcacacaga ccccaaccac gacacccatc accaccacca ccacggtgac    24660
cccaaccccg acacccaccg gcacacagac cccaaccacg gtactcatca ccaccaccac    24720
tacgatgacc caacccccaa cacccaccag cacaaagagt acaaccgtga cacccatcac    24780
caccacaact acggtgaccg caaccccaac acccaccggc acacagaccc caaccatgat    24840
acccatcagc accaccacta cggtgacccc aaccccaaca cccaccactg gaagcacggg    24900
gcccccacc cacacaagca cagcaccgat tgctgagttg accacatcca atcctccgcc    24960
tgagtcctca acccctcaga cctctcggtc cacctcttcc cctctcacgg agtcaaccac    25020
ccttctgagt accctaccac ctgccattga gatgaccagc acggcccac cctccacacc    25080
cacggcaccc acgaccacga gcggaggcca cacactgtct ccaccgccca gcaccaccac    25140
gtcccctcca ggtaagcaga gccgcttggt tcctctggcc tgggatgctt cttcctcccc    25200
```

```
ttgtgccggg caggactgtc ccaggaaggc tcaaggcacg ttctgggcgc ctctctgccc    25260
acgaagcttg gtcactgtgt gggcagaagc cactgacact ggccagtgct gggcagtgaa    25320
gccaaaggcc attccgcttg cccataggac agccttctga ggagctgctg acaccggcca    25380
gtgctgggca gtggagccct tggctatcct gctcgcccat aagacggcct tcttcagggg    25440
cccactgcta tgtgatgcgg tgctgtggga gcccatcaag gctgggggc agagagaggc     25500 tgccagtgag gtgcctgcgg gtccacctgc ttctggctgc agcccctcct tggggccttt    25560
tcctggtgga cggcatgcca cagccagtgc cttctggacg cctcttgctg gccatcggct    25620
tggccagcaa gctgtgttgc tgccagagca ccaggtcacc tgcaggctct cgtgacactc    25680
ggctgtggtg atactggcct tgccgctcca ccctgcctgg tgactctgag agcctgggag    25740
gtgggcacga ggccctggtc ctccagttct gccacccggt cggctgtctg gctcccttgc    25800
agctggggag tggcagttgg gaccctgtgg catctgagat gtgcaacgtc tcagccctca    25860
ctggtgtctc ctgctctcac aggcaccccc actcgcggta ccacgactgg gtcatcttca    25920
gcccccaccc ccagcactgt gcagacgacc accaccagtg cctggacccc cacgccgacc    25980
ccactctcca cacccagcat catcaggacc acaggcctga ggccctaccc ttcctctgtg    26040
cttatctgct gtgtcctgaa cgacacctac tacgcaccag gtactcaggc tgttcacatc    26100
ctgtgcttgg gtggccgagg ctggccccgg catgtaccaa tgggtcaggt gccagggctg    26160
agatcgcagt agaagcgtct caggaggcag cagccgtcga gggtggctgt gtccagggca    26220
cggcttccct tgggtggcct ctgtggggac ctccgctgtg gggacctcca cggggtccag    26280
cggctagccc tgcctccggc tagccctgcc tctggacggt gtgatcgtgg gtctgtctcc    26340
cttcgcaggt gaggaggtgt acaacggcac atacggagac acctgttatt tcgtcaactg    26400
ctcactgagc tgtacgttgg agttctataa ctggtcctgc ccatccacgc cctccccaac    26460
acccacgccc tccaagtcga cgcccacgcc ttccaagcca tcgtccacgc cctccaagcc    26520 gacgccggc accaagcccc ccgagtgccc agactttgat cctcccagac aggtcagtgg     26580
gctgcaggcg gctttgtccc catggcactc tgcgcagcat gtccgggcag ctgaggcccc    26640
aggcaccact tcctgctggt cgtctgaggg ccgaggcctc cagcaaccct tgggtgcagg    26700
gtctgccgag ccctccacat tttcaccgtg ccccgctgtg cctggcgagg tggctggctg    26760
cagtgaggtc cgtggaagcc acttcggcct ccagcctccc ggctcagcac ccgcccctcc    26820
tgagcgcaga ccaccccatc ctgtgccggt ccccctgacg tcccttgcct cccgtcccca    26880
ggagaacgag acttggtggc tgtgcgactg cttcatggcc acgtgcaagt acaacaaacac   26940 ggtggagatc gtgaaggtgg agtgtgagcc gccgccatg cccacctgct ccaacggcct     27000
ccaacccgtg cgcgtcgagg accccgacgg ctgctgctgg cactgggagt gcgactgtga    27060
gtccggggcc cccaggccct ccccgcatct cctgccctct ccgtgggtgg ggctgcagg     27120 gcccgtctcc cggggcgga agggctgagg ctccttgggc acagatccca ctgaggtgtt     27180
cgctgaggct gggtgacttc tgagggtctt ctcacagccc tgcttttgcc tcattgggtg    27240
gggagggcct gggcaggtgg agggcttgcc tggtggagtt agggctcctc cctggaacaa    27300
gggtgcttct gaggcaagag ggggctgagt tgaagtttga accctggtcc gtcctgcaga    27360
atgggccact gtgggtgcgc agggcaagt gcagctcaga catccccgtg cccacgcaca     27420
ggagtggggt tttcaggccc cagcttcctg ctggctcttc ctgactatgc ccagcccag    27480 cccttgcacc cgacccggc cgaggggcac aggtggcacg gctcactccg gctcccttgc     27540
aggctactgc acgggctggg gcgacccgca ctatgtcacc ttcgacggac tctactacag    27600
```

```
ctaccagggc aactgcacct acgtgctggt ggaggagatc agcccctccg tggacaactt   27660
cggagtttac atcgacaact accactgcga tcccaacgac aaggtgtcct gccccgcac    27720 cctcatcgtg cgccacgaga cccaggaggt gctgatcaag accgtgcata tgatgcccat   27780
gcaggtgcag gtaggcacag cgtggccaca ggaggctggc atggaggcgg gtgctgacat   27840
gggccccaat gcaccctggt tccccagggg ccagaggact gggctgtggg ggtgccaagg   27900
catagcctct cctagagttg ggctagaagg taggatgggg tgggcgactg gctccgggac   27960
atatcagctc ttcctgcagg ccctccaggt gtgtcctggg cccctcgagc cctggcacca   28020
tgccacgctg ggcacagtct ctgcagcaga agctgcctcc tgaggacaga gtcagggaca   28080
gggctctgca cacccttggc tgagatgccc ctacttgcag gggaatcatt ggttctgagg   28140
ctcaggaggc cccgggagcc tgcgccgggc tccacagtcc caggtgctc  ccaggagagc   28200 tccttcactg gctcacccat gggaccaggg tctggttggg agcagtggag tggaagcaag   28260 aaaggggca ggaaagcggg gtaggcaggg ccctctccct acatgtgtag gtcagagagc    28320
aggcggggtg gggcagccct ggagctctca caaggagagg accgaggcag ctgcagctcc   28380
catggtgtgt cggccacagg tgcaggtgaa caggcaggcg gtggcactgc cctacaagaa   28440
gtacgggctg gaggtgtacc agtctggcat caactacgtg gtggacatcc ccgagctggg   28500
tgtcctcgtc tcctacaatg gcctgtcctt ctccgtcagg ctgccctacc accggtttgg   28560
caacaacacc aagggccagt gtggtgagtt ccgtgacccc catggccccc gaggccccca   28620
cggctcccac cgtcccctgt gccccatgt cctgccccag ggcgggtggc caggccaggc    28680
tgaggctgag gctgcgtgta acacccatg  ggcctggctg tgggcctctt gccccgctgc   28740
tcggggctgc tgtggccatc acccgggttc agtctctgtg aggagccaac aggaggggc    28800 ctggcctggt ctctgccctc ggccctggct ggccggtcct gggcatctgg gctggagaag   28860
ggcagggctt accctgtctg caacgtggcc tctctcactg atacaggcac ctgcaccaac   28920
accacctccg acgactgcat tctgcccagc ggggagatcg tctccaactg tgaggctgcg   28980
gctgaccagt ggctggtgaa cgaccctcc aagccacact gccccacag cagctccacg    29040 accaagcgcc cggccgtcac tgtgcccggg ggcggtaaaa cgaccccaca caaggactgc   29100
accccatctc ccctctgcca gctcatcaag acaggtgac  cccgcccagg cctgcctgtg    29160
gccacgacac caataagctg agggcctctg tgccccagcc cccagctctt gcaaagagga   29220
aggaggcagc gcgtggggcc tggcgctggg gctgggaagg cacggagccg cggaaccagg   29280
atcaggcgct aggtcgccgt ggggtccagg acccaggccc ttgggttcca cggggctgag   29340
ctgctacgtg cggcctgtgc ctttgctgaa ctccagtctc tcctggctcc cgggaaggtg   29400
cagggctggc cgagtgtgag gcccggagta aaccagtcaa cccaggacag agctcagggc   29460
tgatattggg agggcagatt tgggctttga cagagagggg gtgctcctaa cgctggcagt   29520
catggggggt cagcatcctg tccctggaag tatagggggcc aggtataggc tgggtgtcca   29580
tctgccaggg ttgctggagg gggtcctgaa gctgatgacc acatagacgt ggtttctatc   29640
tctgggagcc gggctgcaga gccaccttgc tcggccatcc cttggtctgt ccctgagctg   29700 tcccctggc tggcctgtcc cttgacccc  catcagccac aggcgcctct ctggcgggtg    29760
ccggactcca ggaggacagt ccgggcagag acgctggggt agagagcagg ggagaggcag   29820
gtgccacctg agtgtgacct tgtgcctctcc ctgcgcagcg tgtttgccca gtgccacgca   29880
ctggtgcccc cgcagcacta ctacgatgcc tgcgtgttcg acagctgctt catgcccggc   29940
```

```
tcgagcctgg agtgcgccag tctgcaggcc tacgcagccc tctgtgccca gcagaacatc    30000
tgcctcgact ggcggaacca cacgcatggg gcctgctgta agtgcccatc tgccctgcc     30060 ctggagctgg gggcctgcag gccagacgtg gtctctaggc tctgccaggt gctgtgccca    30120
gcctgaagct agacctagat gggctgcggc cagggacgca gagatggcgg gtgtgagacc    30180
agggctgggg ccatggggtg gggaaggcca ggctggaggg gctgaggtgc tggggcttct    30240
gccagcatcg ctaaatgcaa ctgggtgccc accacccagc tcgggacaac ctcgagggtg    30300
gaggttgatg cccaggcagc tggtcaccct cctccgtgtg tggggcactg gcagctgtc     30360 actcaagggg gtccaggctc ctccgcctga catgaggcag ccctctgacc tctgcccatg    30420
tccctcagtg gtggagtgcc catctcacag ggagtaccag gcctgtggcc ctgcagaaga    30480
gcccacgtgc aaatccaggt atgttgtttg agggtccacc aggaccgtgg gctcgccttc    30540
tgcagtgcgg agggtggcat catctgggca tagcagtccc acctgccagc tccccagccc    30600
caccccacct gtctgacaat gccctcccgc cccagctcc tcccagcaga acaacacagt     30660
cctggtggaa ggctgcttct gtcctgaggg caccatgaac tacgctcctg gctttgatgt    30720
ctgcgtgaag acctgcggta cgccaccac tcacactgtc ccctcctgcc tccctcctgc     30780
ctcctcctgg gtgtccacgg aggctgggac caggacgctg accacccccc acctctgatc    30840
cctgttgcac aaggactctg ctaacacaac ttgtctcctg ggtgtccatg gaggctggga    30900
ccaggaggct gaccaccccc acccctgctc cctgctgcac aaggactctg ctaacacaac    30960
ttgtttcttc cctcttccta ggctgtgtgg gacctgacaa tgtgcccaga gaggtaggcc    31020
ccaccgtgtt gctgggggat ccttccacaa attctgaatt ctggggagtg agggatggac    31080
atgaaaacct ggagcctcaa agattgagga atgaggtcat ctaagtcctg gatggctgag    31140
ttggcatgga caccacccac tcacccaccc atccttccac ccaccccactc atccacctgt    31200 gcacccatct acccactcac ctaccctcc atccttccac ctacctagtc atcacccact     31260
catctatgca ccccccacc cacccactca tccatccatc catccaccat ccacctaccc     31320
aaccatccac ccatccatcc accatccatc taccatccac catccaccca accatccacc    31380
atccatccat ccacccatca tccatctacc atccacccac ccaccatcc atccatccat     31440 ccaccatctg tctaccatcc acccacccac tcatccatcc atccatccac catctgtcta    31500
ccatccaccc acccacctat ccatccaccc atccatccat ccatccatcc atccatccat    31560
ccatccatcc acccaccatc tgtctaccat ccacccaccc acctatccac ccatccaccc    31620
acccatccat ccacccaacc atccaccatc catccatcca tccatccatc caccatccat    31680
ctaccatcca ccctccatc catccacgca tccacccaac catccatcca tccatccacc     31740
atccacccac catccaccca tttatccatc cattctccct ccctccattc accacccatt    31800
ggtcatatga tactctgtct agaagctctg acatgacatc ttggccacct ctgtgctgcc    31860
catgcctcct acctgtggta gcagccatgt ggatgattcc ttagctaaat tctgtacaaa    31920
cctgagaggc ctgagtggag aatttgccac gtgccaagcc cctgcttgtc gatgctggtg    31980
agcaggtaat ggctttgtga tatcagtgaa tgagcagcta ctgtcctatc ccagaacctg    32040
cctggtgtgc tcagaagtga ggagggacat ggttttcccc caggatccct cagcactctg    32100
ctcagggtgg ctgtttctcc ccgctgacca cagctgcagc tccggggctg tggtgaggtg    32160
gggcctgcct ggtgccacct gtcctctcta ctcacccttc tttccctgca gtttggggag    32220
cacttcgagt tcgactgcaa gaactgtgtc tgcctggagg gtggaagtgg catcatctgc    32280
caacccaaga ggtgcagcca gaagcccgtt acccactgcg tggaagacgg cacctacctc    32340
```

```
gccacggagg tcaaccctgc cgacacctgc tgcaacatta ccgtctgcag taaggccatc    32400
ccctggggcc catgccacct ctcaggggtg cacacatccc tgtaggctgg gctgcctgct    32460
gtcccctcct tggcaagtga ggaaacagct ggcttggggg cctctgctgt gccccttgag    32520
agggcttggg aggggccgc tgggcccagt ccaggcatcc ctgctgcagg gcctgacctg    32580
ggtggggagg ggaccttgg aggtgctgga ggcccgaccc tgtgcagtgg ccccgggggc    32640
tttgcctggg aggagccacc ctcacggccg cgtgcgcacc ctgtcttcag agtgcaacac    32700
cagcctgtgc agtggccccg ggggcttggc ctgggaggag ccaccctcac ggccgcgtgc    32760
acaccctgtc ttcagagtgc aacaccagcc tgtgcaaaga gaagccctcc gtgtgccgc    32820 tgggattcga agtgaagagc aagatggtgc ctggaaggtg ctgtcctttc tactggtgtg    32880
gtaagcaggg ctggtgggca gggcaggag gaggctgccg cccggggtgg ggtgctgta    32940 aggggggttgg ctccctcctg ggggtctcag attctgggga cacagatggc tgtacgcttg    33000
gctgatgcac ccaccccagc cctgagcgct cgctccatcc actgggtgtg caccgggagt    33060
gggggtctgg ccaggtggcc gccccggggc agtctccaac gaacggcctt ctccgttctt    33120
tctcccaaga gtccaagggg gtgtgtgttc acgggaatgc tgagtaccag gtgagccctg    33180
ggctgggtga gagggaggag gggaggaggt cggctgcagc gtggggtcc tggcaggctg    33240 ttgggctggc tgggatgctg gagaggcccc tgcctcatgt ctctccctgt gcccgaagcc    33300
cggttctcca gtttattcct ccaagtgcca ggactgcgtg tgcacggaca aggtggacaa    33360
caacaccctg ctcaacgtca tcgcctgcac ccacgtgccc tgcaacacct cctgcagccc    33420
tgtaagcggc caccctcctc cttcagcctg cccttttccc tcctcccaga caagcacccg    33480
ggcccatgtc tgcatcgtga ccctttcttt cctcctttca acgccaacct gtccctgtcc    33540
ccacctctcc atcctgacac ctgcccagcc tggggcctcc tccaggtggg ggggtctcgg    33600
cagccctgca ggctttgtgt ggtgtggggt acagcctggg agttcagttg cagtggcgtg    33660
tctatgtgcg cagggcttcg aactcatgga ggccccggg gagtgctgta agaagtgtga    33720
acagacgcac tgtatcatca aacgcccga caaccagcac gtcatcctga aggtaggtgt    33780
gcactgccgg cccccgacgcg gccgggttgc ttgagcccag gcaaggcgc gggccaccca    33840 ggatccccca gctgagtcct cccagtcctg ggcgcagctg tgatgggcgc cctggggctg    33900
ccatgacaaa tgagcaggcg tcttcagggc agaaagggat tctcctggtt ctgcggccca    33960
gaaatccata gagcaaaggg cctcagggct gtgctccctc ggaggcgcta ggcaaggacc    34020
tttcccagcc tctggtcact ctaggtgccc cttggctgtg accacgaggt ttccttccct    34080
gtgtctgcct ctcctctccc ttttaaggat ttaggcaccc caagcaggat gatctcatct    34140
taggatcctt cacttaatga caccttcaaa gaccccttt ccaaggcagg tcacattcat    34200
agattcagag ttagaacaca gacagacctt tgagggttgt gtgggctcca ggctggtgcc    34260
tgatgtgggg ccccgcccat gtcacttgtc ctgtggccct gggcctcacc aggaagcctc    34320
cccggccagg tgtctccagg gtgtcttcct ggccgggctg gggctgggcc tgctgccctc    34380
cctcaccaga gctccctgcc ccacagcccg gggacttcaa gagcgacccg aagaacaact    34440
gcacattctt cagctgcgtg aagatccaca accagctcat ctcgtccgtc tccaacatca    34500
cctgccccaa ctttgatgcc agcatttgca tcccggtgag ttggccacct ggggcctggc    34560
tgtgtgtact ctgccgggag tggggtgcc tggtgttctg ggggctggg gccccagtgc    34620 tgcgacagtg acctcgggcc tggtctgagc tgccgcagga ggctttgcct ggggctttct    34680
```

| | |
|---|---|
| gcagcagcta cccccgccca cggcatcgtg ggaaggtgct ctcatcccca ggaatgtccg | 34740 |
| ggggtcccgg gctcattctc ctttccctct agggctccat cacattcatg cccaatggat | 34800 |
| gctgcaagac ctgtgagtac agggcacagc ctgggggta ggcagggtgg gggcacaagg | 34860 |
| gctggtgccc tcagcccgc ctgggtggc tggaggctgg acaacggcct ctgggtgggc | 34920 |
| agtgagggct gggggctgag gccgagcctg ggaggggac gcagcgaggg agagcctcct | 34980 |
| cgaagatgtg gaggccctgc cctaagccgc tgcccgctct ccccaggcac ccctcgcaat | 35040 |
| gagaccaggg tgccctgctc caccgtcccc gtcaccacgg aggtttcgta cgccggctgc | 35100 |
| accaagaccg tcctcatgaa tcattgctcc gggtcctgcg ggacatttgt catgtgagtc | 35160 |
| ccaggctggg agtgtgcctg gagggggtgg tggagacccc agggaggcga gaggccagcg | 35220 |
| ctggccccgg aaggtcaccc ctcactccgc cctccccca ggtactcggc caaggcccag | 35280 |
| gccctggacc acagctgctc ctgctgcaaa gaggagaaaa ccagccagcg tgaggtggtc | 35340 |
| ctgagctgcc ccaatggcgg ctcgctgaca cacacctaca cccacatcga gagctgccag | 35400 |
| tgccaggaca ccgtctgcgg gctccccacc ggcacctccc gccgggcccg gcgctcccct | 35460 |
| aggcatctgg ggagcgggtg agcggggtgg gcacagcccc cttcactgcc ctcgacagct | 35520 |
| ttacctcccc cggaccctct gagcctccta agctcggctt cctctcttca gatatttatt | 35580 |
| gtctgagtct tgttcagtc cttgctttcc aataataaac tcaggggac atgc | 35634 |

<210> SEQ ID NO 31
<211> LENGTH: 21849
<212> TYPE: DNA
<213> ORGANISM: Homo sapiens
<220> FEATURE:
<221> NAME/KEY: misc_feature
<222> LOCATION: (1)..(21849)
<223> OTHER INFORMATION: CEACAM5

<400> SEQUENCE: 31

| | |
|---|---|
| gatgctgaga agtactcctg ccctaggaag agactcaggg cagagggagg aaggacagca | 60 |
| gaccagacag tcacagcagc cttgacaaaa cgttcctgga actcaagctc ttctccacag | 120 |
| aggaggacag agcagacagc agagaccatg gagtctccct cggcccctcc ccacagatgg | 180 |
| tgcatcccct ggcagaggct cctgctcaca ggtgaaggga ggacaacctg ggagagggtg | 240 |
| ggaggaggga gctggggtct cctgggtagg acagggctgt gagacggaca gagggctcct | 300 |
| gttggagcct gaatagggaa gaggacatca gagagggaca ggagtcacac cagaaaaatc | 360 |
| aaattgaact ggaattggaa aggggcagga aaacctcaag agttctattt tcctagttaa | 420 |
| ttgtcactgg ccactacgtt tttaaaaatc ataataactg catcagatga cactttaaat | 480 |
| aaaaacataa ccagggcatg aaacactgtc ctcatccgcc taccgcggac attggaaaat | 540 |
| aagccccagg ctgtggaggg ccctgggaac cctcatgaac tcatccacag gaatctgcag | 600 |
| cctgtcccag gcactggggt gcaaccaaga tcacacaaat ccctgccctc atgaagctca | 660 |
| tgctctcatg gggaggaaga cagacataca aagagatcta gaatgtgagg tcaggtgttg | 720 |
| acaagagccc tggagggaat agagcaggga aaggtcagaa aaggaagacc cagggtctct | 780 |
| agaggaggtg tcaggaagg gatctcccaa gaatgccctg atgtgagcag acctgaagg | 840 |
| caatggggag ggagccgtga agacccctgg aaaagcagat tccacacagg gaaatgccaa | 900 |
| ggtcagaggt gctaaggaaa taggagacac actgctgacc ttgacctagt aggacacaca | 960 |
| cacacacaca cacacacaca cactcactca ctccagggct gggggatgaa gagacctgct | 1020 |
| caggacccag gaccccattt ttccaccta atgcataggt cccaatattg accgatgctc | 1080 |

```
tctgctctct cctagcctca cttctaacct tctggaaccc gcccaccact gccaagctca    1140
ctattgaatc cacgccgttc aatgtcgcag aggggaagga ggtgcttcta cttgtccaca    1200
atctgcccca gcatcttttt ggctacagct ggtacaaagg tgaaagagtg gatggcaacc    1260
gtcaaattat aggatatgta ataggaactc aacaagctac cccagggccc gcatacagtg    1320
gtcgagagat aatataccccc aatgcatccc tgctgatcca gaacatcatc cagaatgaca    1380
caggattcta caccctacac gtcataaagt cagatcttgt gaatgaagaa gcaactggcc    1440
agttccgggt ataccgtgag tgattccccc atgacctctg ggtgttgggg gtcagttcta    1500
cttcccacac acaggattat caggcctggg ctgtgcctgt ggcccctct gcattacgca    1560 ccatgttagg gtttgggcat ttagtgcagg atacacacag aagagacaaa cttcaacaga    1620
tcagaattcc tttccggcat ccagaccctg cagacactca ctgcagagga aggacagtct    1680
gatgtggggg acttagcagg gggaggtcag tctcagccaa gcaccccgtg ccctccccgt    1740
aaacctgacc ctgagaaaga ccctggagaa ctgcatcaga gcctggcctg agggaccct    1800 gggatattca cagagaagct cagccccagg gctcctggtt ccaggtgact caggggagcc    1860
tgtgccaggg ctgtgttgtg gcctcctggg caaggctaac tggaagcaag gacttagcag    1920
ctgtccaagg gctgtggctc ctggagctgg attctggatg cagaatcgga cttctggcc    1980 acacttgttc cctgtcccca gagtctcatt tggacaagga cagagccttg tcctttactt    2040
gagactcaat gtggggagga tagatagaca aggttattag ggtgtcagtc cattgccctg    2100
gggacatagg tgactccatg ggaagctcag tgtccccagg aagaggaaca gaggagagaa    2160
gatgctcccg gcagctcctt gtccaccagg gatcaggccc agggccttct ctcttggagg    2220
caaataaaca taaatgatgt tcatttgagc agctcctctg tgcagagctg agatcaagta    2280
attgtaaata ttttgaggtt aattcacaaa caacctcaca gccaaatagc acttatccta    2340
cttattgaaa ggaaattgag gcacaggag acagtcacta acaagggtca cacaggccat    2400
aggtgtcaga ttgaagtcac atgaggtctg tctgtagcca cagccccctc ctctcctcaa    2460 ctggggtgg gtggggctgt ttgttgttag gcatctgcat ctgagaccag tcatgggctt    2520
gcgttctttt gtcttgggca tccacagctc agaagcggag attctggtct ggagagtgat    2580
aagtaaatgg agaaataatc agttttactc tagaactaga tcacctcaac agtcagggtc    2640
agtgccggga ttgtccaggc ctctccctga gatccacagc cccctcacat gacctcaaat    2700
cctgtgtttc ccgatgtgtc agtgtcactc ccacggaagg ataaaggaaa ggacttcgct    2760
ttctctcccc actcacaccc tgtgccaaca gaggcccaaa gtgagacaca cgcttgctca    2820
gtagctctct catgaagggg ggaatgagtg aaggaatgat ccataacctc tatagagact    2880
ggatcctgga tgcagaatcc tgggaggttc tgaccacacc tgttccgtgt ccatcagggg    2940
ctgagatcca tgtaccattc ctctgacccc ctgtcccgaa agccacccta tctcatgtga    3000
ctctggggtt ccttggccat gggagggttt tcaaggctcc ctggtcctgg tcggacagc    3060 caagggactc ctagtcctgg ggtctccgag gtcactatac cccgcatggc tcattgccat    3120
gggcatttct gactttcttc tattcctcca tgttcttcgt cttcctccct cttcattcca    3180
gctgagatgc ccatccctga acatcttcct ccactcttag gccttcccca gacactccct    3240
tgaacaaggc tggctgtcct gtttttcttgc cgctcacact gtgtcctggc ccacttccca    3300
ggcaatAggg aaggcacaga aatcacaggc aataggaag gcacagatgg agcccctgcc    3360
aggctccatc acaagccaat gtcaacaggt caccaggaga atgagcttcc gctgtgttcc    3420
```

-continued

```
tgcccagggc tctttacttc catgaggcca acacacggaa caggcagcag gacgggaatg    3480
agcgactcct ccatccactc cctacactga ctcaccaggg ggtcagaggc agaaggacag    3540
gtctgcagtc cccaaagccc gcatgcttat ttcactcact tcactaccca ctccatcttc    3600
atcctggtgt ggggctcaca tcctccagtg gatcctggga cctcccccag gtggagctgg    3660
ccaggcaggt gctgtctgat aggtttgctg cccattccac atacacctgt gtcctcatga    3720
tgatgccatt gtcataaggt ggagtccctt ggactgagaa gtgaaccagc cactggcgtc    3780
tcacttagac tctacccagt tacaaaaact taaactctag ttgtgttttc tgaggttgat    3840
aggagaggaa gaaaaccttt cacatgcctg ttttgaggct tctcctcttt ttgcctaact    3900
ctgcacagga actaggggca gggagcgctt tctaaattta ctaacatcac acacattgct    3960
tctcctaact tggcatcatt tctccccttta tgtaattgac acacctaaga gttcctctct    4020
gaccggttct gtcctcttaa caggtctcac atccctctct ctgttcaggg agtcactgat    4080
ttcaaaccac tttcagcatc ttcctttgag cataatgtga tcactttgga attcagagca    4140
gacctaaacc ttagcataat attaaaagaa gtactacttc cagcaattga tcttagatct    4200
ttaggccatt gataagaatt tccacttatg gaaaaatttt aatgtttccc ccaaatgtct    4260
ttcacttttt taactatagt cagaaaataa catgagatct aaactcctga caaatttttta    4320
agggcaaatt atagtactac agattgagta tcccaaatcc taaaatccaa aatctgaaat    4380
gctccaaaat ccaacatttt ttgaccactg acatgattct caaagaaat gctcactgaa     4440
ggccgggcac ggtggctcat gcctgtaatc ccagcacttc gggaggccaa ggcgggaaga    4500
tcacaaagtc aagagatcaa gaccatcctg gccaacatgg tgaaacccccg tctctactaa    4560
aaatacaaaa attagctggg cgtggtggca tgcacctaca gtctcagcta ctttggaggc    4620
tgaggcagga gaatcgcttg aacccgggag gtggaggttg cagtgagctg agatcgtgcc    4680
actgcactcc agcctggcaa cagagcgaga ctccatctca aaaaaagaa aagaaagaa     4740
aagaaaagaa aaaagaaagg ctcactggag cactttggat tccgtatttt cagatttggg    4800
gtgctaaact ggtaagtata ttgcaaatat tcaaaactca aaaacagtca gaaatccaaa    4860
acactttag tcctaagcct tacacataag acatactcaa tctgtatgaa ctataggcac     4920
caagctgaac agcagatccc tagaacctcc tcatcctgca taactgaaac tgcagaccca    4980
tgaacaactc tccattcccc cagttcccag gctttgacaa ccaccattct actctctgat    5040
tccacaagtg tgactactct agggacttca tataagtgga atcctacagt atctgccctg    5100
tgagtggctt atttcattta gcataatgtc caatgggaga aaataattgc aaaacttctt    5160
ctcaaagttc tgtctcataa ctgtcaaaca cacatggtcc ttgagggcca gatttccagc    5220
agttcatgct ccccttttc caccagtcag ttctgcattt gcaaatgtcc acatgtattt    5280
atggagagat ccacagcatc ctcgcctgcc ctctgcaagg ggagaaggga cattaaagac    5340
caaagacagg ccgggtgcag tggctcatgc ttgtaatccc agcactttgg gaggccaagg    5400
tgggcagaac acctgaggtc agaagttcaa gaccagcctg accaatatgg tgaaaccccca    5460
tctctactaa aaatacaaaa tttagctggg tgtggtggtg ggcgcctgta gtcccagcta    5520
ctcgggaggc tgagacagga gaatcgcttg aacccgggag gcagaggttg ccatgagccg    5580
agatcgtgcc tggccaacac agcaagactc catctcaaaa aacaaacaaa caaacaaaga    5640
ccaaagacaa agaacataca tatggttctg ctgttaaatc cgggcagctc ctgcctgtca    5700
cctgaagttc tagatcattc cctggactcc actctatctt taggggtctc tggctcaagt    5760
cagtcatcat caaacacctg ggaaaaactg ccccaccttg tgcctccact gcctaacgac    5820
```

```
                                                 -continued tgagctgacc tccaggcttg cctctggtgt ccctgtgtt atttctactg aaacatccag   5880
tcccaggcca ggctgcacaa tatgtacagg gtttaaggac aatgggaaga cccatcacta   5940
tccatttcta ggatgtcctt gcaaagggaa accacagaaa aaatatacct agggaaacaa   6000
agtaggactg aaggtggaag ggacccagca cttgaatgtt ccaggtgagg accctacagt   6060
gggccaagta gtcaactggt cagggaggga ccaggagagg caccaggagc tgtgacctcc   6120
cccccagtcc tgtgtctgtt cacagcccaa tgctgctgct taattcacac ttgagaaagt   6180
ctgtgcttcc cccacaccga gcaggcagcc tcgcagtctc tgagatctca gatcatcgtg   6240
catctgtctt gtgacacatg cacccaccgt gggtttttaa gggctcaggt gggctgagag   6300
gtggaaggtg ccaactctga ttgaaagatg cctgtgagga atcaaaggtg ccacacaggg   6360
caatcttctc tctgttatct gcacagcgga gctgcccaag ccctccatct ccagcaacaa   6420
ctccaaaccc gtggaggaca aggatgctgt ggccttcacc tgtgaacctg agactcagga   6480
cgcaacctac ctgtggtggg taaacaatca gagcctcccg gtcagtccca ggctgcagct   6540
gtccaatggc aacaggaccc tcactctatt caatgtcaca agaaatgaca cagcaagcta   6600
caaatgtgaa acccagaacc cagtgagtgc caggcgcagt gattcagtca tcctgaatgt   6660
cctctgtgag tatatctgct cctctctggc ccaggctgcc agcccaaatc cacagggcca   6720
gaggcaggat ttctcagtcc ctctcaggtt caagtacaca gaccctcaac cctggacatc   6780
cagactgtct gtgactttct gccccagaaa aacctgggca gaccaagtct tgaccaagaa   6840
taggagggga gggctgctt ctgtcctggg aggctcaggg tccacaccct atgatgggag   6900
aaacaggtga atatctcaga ctcaggctca gtagatacaa gaggggtttg gctgagactt   6960
taggattgtg attcagctta gagggacact gtggtccttc catagaccag gaacttccac   7020
ttccctctga caatatcacc tgtggcttta ttttgtttgc tccagatggc ccggatgccc   7080
ccaccatttc ccctctaaac acatcttaca gatcagggga aaatctgaac ctctcctgcc   7140
acgcagcctc taacccacct gcacagtact cttggtttgt caatgggact ttccagcaat   7200
ccacccaaga gctctttatc cccaacatca ctgtgaataa tagtgatcc tatacgtgcc   7260 aagcccataa ctcagacact ggcctcaata ggaccacagt cacgacgatc acagtctatg   7320
gtaagtggat ccacgaagca ctgacatcat gttttgaggt ggagtctgtc tggttttcaa   7380
acaagagcca ggaagacatt ttctatccca gcctgtgtcc agtgggcaca agcaaatccc   7440
agattctccc actgaacctc cccaatatgt ctctacagac tcttttcttc ttgttctgat   7500
ttctcatggc gggcccagg tccagcttgg aatgtgggga ggaggctccc tcagccccac   7560
agccctgtgt agtggaggaa gcttcacaga gcgggaagga gcaagggttc tcaaggtcaa   7620
gttgcttctc tctgtcacca atgtgtccct ttctgtcacc tctttgtgtt cttttgccta   7680
ctccatgagc tacaagcaac attcaaggct ttgaaacaag ctcatacttt tttcccaaat   7740
gagagaagga agcccttgg gtgagggaga cacagctcag actgctccct gctctgctct   7800
gggctcccct gggtgactgg ccttgcctga ctccacctag gtgggaacga ggtgtgtgga   7860
gaaggagccc gggtggtctg tcctgaattc ggctaaatca agctgccaat caacaccaaa   7920
gcttcccttc gtcccagtca ggctgcagga aaatggaaag agaggagcc tcagggcaga   7980 ctcctgagct gcgtcctggc tctgatgtca ccagctatat gaggctgtgg gcacagcaca   8040
tgggacacag cacaggggac agcaagtgac ccacacttgg agaaatcagg agattccaca   8100
caggggctct gcacggcagg gaatggcagt gtcaaaaatc gtgtgtttat acagatggta   8160
```

```
acagtacata tctaacacaa acttaccatc ttaacttttc tacacatgca gttcagtggt    8220
attaaatata ttccccttgt tctgcttcca tcaccaccat ctaccacag gactcttttc     8280
ttcctcccaa aatgaaactc tgttcccatc aaactcctgg gcagagctgc cccatctatg    8340
gcccacagtc tgatccctga cttgtcacct ctagacatgc tcctagtctc ctgcactatt    8400
tctgctcaaa catccatctc catcatcacc tatctctagg atgtccttaa atagcaaagc    8460
ctcagagcaa acacaacttg gctgggtggt gtgggactgt gcagctggaa gaaacgcagc    8520
tccttcaaat tccaggtgag gaccccaatg ggccaggcag ccagccagtc aggaaaggac    8580
cagaagtgct gggggctgtg accccagcc ctgtgtctgt ccacaaccca atgctactgc     8640
ccaattcaca cttgagaaag tctgtgcttc tcccacacaa aacagccagc ctcatggtct    8700
ctgagccctc agatcattgt gcatctgtct tgtgacgcac acacacctgc catgagcttt    8760
taaggactca gttgggctga gaggtgggag atgccaactc tgattgatag atgcccgtgg    8820
aggaatcaca ggtgccacac agggcaatct tctctctgtt atctgcacag cagagccacc    8880
caaacccttc atcaccagca acaactccaa ccccgtggag gatgaggatg ctgtagcctt    8940
aacctgtgaa cctgagattc agaacacaac ctacctgtgg tgggtaaata atcagagcct    9000
cccggtcagt cccaggctgc agctgtccaa tgacaacagg accctcactc tactcagtgt    9060
cacaaggaat gatgtaggac cctatgagtg tggaatccag aacgaattaa gtgttgacca    9120
cagcgaccca gtcatcctga atgtcctctg tgagtatctt ctgttcctct gtggctcagg    9180
ctgccagccc aaatccacat agccaaagtc caggcctctc agtccctctc aggcccaagg    9240
acagagactt tacccctgg acatccaggc tggcctacc cccagcaaat ccatgcaggc      9300
ccagtcctga ccaagaatag gaggggaggg tctgctcctg tcctgtaaca ctcgggatcc    9360
acagctagtg atgggagaaa cagatgaatg tctcagactc tggctaattg gatacagtag    9420
gggtttggtt aggacttcag gattgtgact tggctcaggg ggacactgtt gccctttcac    9480
agaccaggag cttccccttt gctctgatga cattccctg tggccctatt ctctttgctc     9540
cagatggccc agacgacccc accatttccc cctcatacac ctattaccgt ccaggggtga    9600
acctcagcct ctcctgccat gcagcctcta acccacctgc acagtattct tggctgattg    9660
atgggaacat ccagcaacac acacaagagc tctttatctc caacatcact gagaagaaca    9720
gcggactcta tacctgccag gccaataact cagccagtgg ccacagcagg actacagtca    9780
agacaatcac agtctctggt aagtggatcc ctggaccgtt agcaatatgt tctggagcgg    9840
aatctgtctg gttttcagaa aagagccagg aagaaatttt ctttcctagt atgcatccaa    9900
tgggcacaag caatcccaaa ttcaatcctg agcactccca atttgtctct acaaacactc    9960
ttccccttgt ttttctgatt tctcatggct gaccttgtgt ccaccctgag aaatgtgggg    10020
aggggtcttc atcagccctg agccctatgt agtggaaggg gcttcacaga gggggaagca    10080
agaagggtcc tcaaggtcaa gttgctcctc tctgtcacca atatgtccct ttctgacacc    10140
actttgtgtt cttttaccta atccatgagc tacaaggaac aactgaggct ttgaaacaag    10200
ctcacacttt ttccccaaat gagaggagga tgcccttgg atgagggagg agcagctcag     10260
actctgctcc cggctccgct ccgggctccc ccagtgactg gccctgccct gatttcacct    10320
ggggtgggat ccgggcatgt ggagaaggtg ctcaggtggc ctgtcctgaa tctggctaag    10380
tcaagatgcc agatgaagcc aagccttccc agggtcaggc tacagggaaa taagaagaga    10440
gggagcctcg gggcagactc ctgagctgtg tcctggagtc tgaagtcacc ggctgtatga    10500
gattgtgggc acagcacatg ggacacagca cagaagacag tcagtggcac acacttggag    10560
```

```
acacacagag attcacccat ggggactcaa catggcaggg aaggggcagt gccaaaaagt    10620
gtgtgtttat agacagggta agaataccag ccactatata tatctaacat aagacaccat    10680
tttaaccttt ctatgtatgc agtttagtag cattaaatat tttcccatta ttctgctacc    10740
atcatccacca tccacccaca gaactctttt cttcttccta aaatgaaact ctgttcccat    10800
caaactcttg ggtagagctg cccacctgtg gcccacagcc tgaccsctga actcacctct    10860
agacttgctc ctggtctcct gagctatttc tgcttaaaca cccatcccg tcatcaccca    10920
tctccaggat agccttgaaa caaaaggctc agagaaaaca ccccacggtt gggtggtgtg    10980
ggaccgtgca gctgaacgga attcagcacc cacaagtccc caggttggcc aggccgtcag    11040
ccatcaggga agaaccaaag gaggtgctgg gggctgtgac tcccagtcct gggtctgtcc    11100
acaacccaac gctgctgccc aattcacact tgagaaagtc tgtgcttccc ccacacaaag    11160
cagccggcct tacagtctct gagccctcag atcatcgtac atctgtcttg tgatacacac    11220
acctgccatg ggcttttaag gactcgggtg ggctgaaggg tgggagttgc caactctgat    11280
tgaaagatgc ctgtgaggaa tcaaaagtgc cacacagggc aatcttctct ctgttatctg    11340
cacagcggag ctgcccaagc cctccatctc cagcaacaac tccaaacccg tggaggacaa    11400
ggatgctgtg gccttcacct gtgaacctga ggctcagaac acaacctacc tgtggtgggt    11460
aaatggtcag agcctcccag tcagtcccag gctgcagctg tccaatggca acaggaccct    11520
cactctattc aatgtcacaa gaaatgacgc aagagcctat gtatgtggaa tccagaactc    11580
agtgagtgca aaccgcagtg acccagtcac cctggatgtc ctctgtgagt atcttctgtt    11640
cctctgtggc cctggtttcc aacccaaatc cacacagcca gaggccagga ctctcagttc    11700
tcctcaggtc caaagaggca gactcccacc cctggacacc caggctggcc ataacttcct    11760
gtcccaggaa aatttgggca acctcagcct ggaccaagaa taggagggga gaggctgctc    11820
ctgtcctagg aggctcagag tccacagcct atgatgggag aaacagatga acgtctcaga    11880
cccagactca gtggacatga gggttatggt ttggactttt tttttttttt tttttttttt    11940
gagacggagt ctcgctcttt cgcccaggct ggactgcagt ggtgtgatct cggctcactg    12000
caagctccgc ctcctaggtt cacaccattc tcctgcctca gcctcccgag taactgggat    12060
tacacacacg tgccgccatg cccagctaat gttttttgta tttttagtag agacggggtt    12120
tcaccatgtt ggtcaggctg gtctcgaact cctgatctgc ccgcctcggc ctcccaaagt    12180
gctgggatta caggcgtgag ccaccgcacc cggccgattt ggactttta acacaggatt    12240
gggacaggat tcagagggac actgtggccc ttctacaatc aggagcttcc cctttcctct    12300
gatgacatca cctgtggctt tgttctcttt gttccagatg ggccggacac ccccatcatt    12360
tccccccag actcgtctta cctttcggga gcgaacctca acctctcctg ccactcggcc    12420
tctaacccat ccccgcagta ttcttggcgt atcaatggga taccgcagca acacacacaa    12480
gttctcttta tcgccaaaat cacgccaaat aataacggga cctatgcctg ttttgtctct    12540
aacttggcta ctggccgcaa taattccata gtcaagagca tcacagtctc tggtaagtgg    12600
ctccctggag catcagcatc atattctggg gtggagtcta tctggttctc accaaagagc    12660
caagaagaca ttttctttcc cagtctgtgt tccatgggca caaggaaatc ccaaattcta    12720
tcctgagccc cctcactcca tctcggccaa ctctctcctc cccggcttct ctgatatctc    12780
acggctgacc tcgggtccag cctggaatgt ggggagggc ctcccttagc cccagaaggc    12840
ccccaatagt gaaagggact tcatagtcca gaagaaagaa gggtccttaa ggtcgagttg    12900
```

```
ctcctctcta tcaccaatat gtcccttttct gtcacctctt tgtgttttttt cacctactct    12960 gtgagctaca aggaacaagg aggctttgaa accagcccac acttttttccc caaatgagag    13020 gaggaagccc cttggatgag gcaggagcag ctcagactct gctccctgct ctgcgcccgg    13080
ctcacccggt gactggctct gccctggctc cacttggggt gggaccgggg catgtggaga    13140
aggtgtccag gtggcctgtt ttgaatctgg gtaaatcaag ctgccaatcc acagcagagc    13200
ctcccttggg tcaggttgca gggaaatggg aaaagaggga gcctcgggac agactcctga    13260
gctgtgtcct ggctctgaag tcactggctg tatgaggctg tggacacagc acataggaca    13320
cagcagagga aagtgagtga cacacacttg gagaaatagg gagattcagc catagggggct    13380 ctgcatggga gggaacaggc agtgccaaaa agtgtgtgtt tatagagagg gtaagactat    13440
cagccactat atatatctaa cataaaactt accattaacc atttctaagt gtacaattaa    13500
gtgaaacagc ataaatatca atcaagtata ttgcccggtg tggtggctca tccctgtaat    13560
cccagcactt tgggaggcca aggcgagtgg atcacctgag gtcaggagtt caagatacag    13620
aaaaaaaaaa atagctaggc atggtggtgg gtgcctgtaa tcccagctac tcgggaggct    13680
gaggcaggag aatcgctcga acctgggcgg tgtagtttgc agtgagccga gattgagcca    13740
ctgcactcca gcctgggtga cagagtgaga ctacatcaca aaaaaaaaaa aaaaaaggaa    13800
aaaataaatc aagtcttttt atactcatgt ctaaccatca catcacacta tccatttcca    13860
gaactttttc atcttaccat actaaacctc tgtacccaat aaacagtaac tccttctctc    13920
ccctaaactc tggtaatctc cattctactt tctgtctcta ggtaatcaac tattctaacg    13980
atcttacaaa aatggaatta tataatagtt gtccttttgt gtctgcccta tttcacttag    14040
cataatgtct tcaaggttca tccatttttgc accatgtatc acaatttctt ccttgttaag    14100
gttgaagaac attccattgt atggatacac ctcattttttc tatccactta tctttcaatg    14160
gacttttcag ttgtttccac cttttggcta ttgtgagtaa tgctgctgtg aacatcagtg    14220
tacaaatatc tgttcaaatc actgccttca attcttttttg gtgtatgtcc agaaatggaa    14280
ttggtagatc aaatgttaat tcttttttttt gtttgtttgt ttgtttgttt gtttgttttt    14340
tgagatggag tctcgctctg tcgaccaggc tggagtgcac tggcgcgatc tcggctcact    14400
gcaagctccg cctcccgtgt tcacgccatt ctcctgcctc agcctcccga gtagctggga    14460
ctacaggtgc ccgccaacaa gcttggctaa tttttttttt tttattttta gtagagactg    14520
agtttcacag tgttagccag gatggtctcg atctcctgac ctcgtgatcc gcctgccttg    14580
gcctcccaaa gtgctgggat tacaggcatg agccaccgtg tccggcccca aatgttaatt    14640
atttatttaa ttttttgagg aaccaccata ccatttttcca cagtagctaa tatttcacat    14700
ttctatcagc aatgcactag agttccaatt ttttccacctc cttgaaaaca cttattgttt    14760
tgtggccatc ctgatgtgtg tgaggtggag tatcattgtg gctttgactt gcatatctct    14820
aagtgttagt gatgttgagc atatttgcat gtgcttgttg gccatttgta tatcttccta    14880
ggagaaatct ctactttagt cctttgtcca tttattaatt gggattttgg attttttgtgg    14940 ttgttgattt gtaagagttc ttcatatatt ctggaaatta atcccttatc agatatatga    15000
tttgcaaata tatttcccat ttcataggtt gccttttcac tttctcgata atgttctttta    15060 atatataaaa gtttttaatt ttcgaggccc tgcacggtgg ttcctgtaat cccagcactt    15120
tgggaggccg aggcaggtag attacaaggt caggagatca agaccatcct ggctaacaca    15180
gtgaaacccc gtctctacta aaaatacaaa aaaaattatc caggcgtggt ggtgggcgcc    15240
tgtagtccca gctactcaag aggctgaggc aggagaatgg catgaaccca ggaggcatag    15300
```

-continued

```
cttgcagtga gctgagatcg caccactgca ctccagccag ggtgacagag cgagactctg    15360
tcaaaaaaaa aaaaaaaaag tttttaattt tcatgaagtc cagtttatca attttttct     15420 tttgttgcct atttgttgtt ataaccaaga catgactgtg aaattaaatg tcattaagct    15480
tttttcccta tgttttcttc tcagagtttt atacttttca ctcttacatt taggtctttg    15540
atccatttta ggttaatttg catatatggt atcaggcaaa gattcaactt gttcttgtgc    15600
atggatattc agctttccct atatcatttg ttgaaaagac tgtcctttcc ccattaaatg    15660
gtcttggcac cgttatcaaa atcatttgg ccatatatgc aagcatttct ttctgggctc     15720
tatattctat tgctttggtt tcaatatctt cctttatgcc aataccacac tgtattgatt    15780
actgtggctt tatagcaaat gctgaaatca ggaagtgtga gtcctccagc ttcattcttt    15840
attttccagg ttgtttggct atttagagtc ctgagattcc atatgaattt caggatatgt    15900
ttttctattt ctgcaaaaaa tgtcactggg actctggtac aaattgcgtt gaacctgcag    15960
ctcactttga gtggtattgt cctcctagca atattgagac ttcccatcca tgaaaaaaaa    16020
atgtctttcc atctattgat gttgtcttta atttccttca gcagtgtttt atagttttca    16080
gggtacaatc ctttcacctc cttggttaag cttatttcta actattttat actattttat    16140
gttaatgtga attggaaatt ttttcttaat ttccttttag attgttcatt gttagtgtgt    16200
agaagtacaa ctgatgtttg cgtgttgatt ttgtatcctg caacatcact gaatttattt    16260
attaactcta acaagttttt taatcttcag ggttttctac agagaagtcc aagttatctg    16320
aaaacacaga tcattttact tctttccaat ttggatgtct ttttttttct tgcctaattt    16380
ctctggctag gacttctaat actgtgtcga atagacgtgg caaaagcagg cattcttgtc    16440
ttgttcctgg tcttacaggg aaagcttttca gtctttctcc attgagtatc atgttagcat   16500
tgggcttttc acacattgcc tttattatgc tgaggtggtt tccttccatt cataattaga    16560
gtgtttttgt tgtgaaagaa tggtgaattt tgtcaaatgc ttttattggt tctatctaat    16620
tataggccta ttaaattttt ttgtgtttcc aggaatttgt ccatttcatc taggttattc    16680
aacagtttgt tggcatacaa ttattcatag cattcttgta gtccttaata tttctgtaga    16740
atttgtagca ttggtagcaa tatctccatt ttcttttttt ttttcttttt tttttttaag    16800
agacagggtc tcactctgta gcccagcaca agctagagtg cagtggtgcc atcatagctt    16860
actgcagcct caacctccaa ggctcaagtg atcttctgcc ccagcctctt gagaagctgg    16920
gactacagac atgtgacacc aagcctggat agttttttaa agaaattttg tagacactgt    16980
gtctgcctat gttgcccagg ctggtcttga cctcctgacc tcaagtaatc ctcttgcttg    17040
agtctcccaa tgtgctggga ttaaatgtgt gagccgctat acctccattt tcatttctga    17100
ttttagtaat ttgaatcttc tctcttttt cttagtcaat ctaataaatg attgtcaatt     17160
ttgttgatct tttttgaaga accaactttt ggtttcattg attccttcta tgttttttca   17220
attttccatt ttatttattt aaactctaat ccttattatt tccttcatgt actatctgtg    17280
gtttgaggtg gttctttttc tgtatcctga agttgtaaag ttaggttgtt gatttgagat    17340
ctctctttat atttaatgta tttaccatta aatttctcac acaagattct taacttctct    17400
gagccttcaa ttcttcaact gaaaattgta ataattctca tcaccaggaa atggaggaaa    17460
aatgaaaatt gcaataagaa tgactgttta acagtattgt tttaaagatt taatgtaata    17520
ttcgattaag ctttcagcaa aatgctacac acagagggaa acttcataaa tattagctgc    17580
tattatcact actgttatta ttagcttgaa gttaggcagt tctagagcca aatcctagat    17640
```

```
ccacttctca ctaattatat gactttggat aagttttttc accactccaa gtctctgtca   17700
tttcatctgt aagatggaaa tcatgcctac ccaacagggt tattgtatgg atcaaatgag   17760
atgccagaaa agcatttaca gtagctaaca tagcattaat catcagcctg agttgactag   17820
tgagagccaa gccccaaatg aaacccact aggacatggt tactggctaa aaatggggga   17880
gagaaaaaaa agttaagtgc aaagaatcaa gcctggtatg ttagttttca tccactgaga   17940
ttcagccaag atggaattag aggtgcaaga taatttaccg gggggaacca ccatgaggaa   18000
aagtggagta gaagtgggag gagcctgaga gagccctcag accacgatgc agatctgatt   18060
cctgagaagg agaaagagga gagagtttta gatagtgatg cagttctcag agtttccaca   18120
aggctggtgg ggcgtcctca agcccctcac ccatgagaga aagcagagt cccccagaac   18180 tgggcttttc attccctgg tgggagccca tgagaagcga gttctctgtg caacggactt   18240
agtaaataca gaatgcacta gcctgggcct tctgccaatc aagtccctgc cacagagacc   18300
caacagactt atttatgcct accacaactg agacactgag aaaagatgc aaccatgaaa   18360 agatagaaag ttctaatgac acgcaaaaat agcaatcaga ctttctcaaa tttcaaagcc   18420
ttcagaaata gctgagtgca gacaggccag ggtggaattg acagaagact gatcaccaac   18480
tagcaacaca gtgagagaga aaaaattgca actttcccac aaaactaatg cattccttga   18540
agcaacaagt agagactgct tcatgctgag agctggaacc tggggcaccc cactgtaaaa   18600
taacatcaca ttcattcctt ctcttttctt tccatgacgg acgattcagc atctggaact   18660
tctcctggtc tctcagctgg ggccactgtc ggcatcatga ttggagtgct ggttggggtt   18720
gctctgatat agcagccctg gtgtagtttc ttcatttcag gaagactggt aggtataatg   18780
gcctttcctc ttgttctgtt tcctgcagtg ctgactgcca tgcttgggag agggaaggga   18840
tttcttcacc tgtatctggg actggatctc ttcctcctac ccccaagctc ctgcttctca   18900
gcactaattc ctgcaggtct cttcttccct ggtcttcatg ctccctgtac gccactgtct   18960
cttagatata attatcccca ccctctgctc atttgtttcc cagattcaat acattgtcaa   19020
agcctcttgg tcctttttta acatctcaca cttgtgtcat tctctccatt cccataaacc   19080
tcaacaactg ctcaaagtcc tgcttgaccc cttgttgcca gtctttgaaa tctttcttgc   19140
atatgactgc ctcattacct tcctaaaatc tagttcactc gcctactcaa gaagacacag   19200
gggcctactg tggtgtatta gataagttca catttcttct ctttactaat cttttttact   19260
tccttaccca ccactcccctt atataattcc atcatcctaa tagatctgtt tccctacaca   19320
tccctgcctc tccaccccac atgtacacag aattcttagt tccggtgtta cacctaaaaa   19380
catgtcaaac agggtgacct ccttccactg tctgcactgt ggagttaccc acacccttaa   19440
tcacaagcaa cttctgacct catgaagaac aaagactgta gcattaacct gtgagtctta   19500
agctcaggac acaactgtgc ctgtgactga gaacctttc ctgataacca attcatatgt   19560
tcataacaga tacagaaatg aagaaggcaa ggtccttaat tctataacag agacaaaaac   19620
ctgaaaaata atcataatgc caaaatagaa aggagtgaac atcacaagaa attagagaaa   19680
tctgacggaa aatatagcta cacattggaa tcactcagaa acattttata aaatggatac   19740
ttaagtccca ccgataaatt ccgatttact ggtctggagt gggacccagg cattcgtaat   19800
ttttaagcct ccccagatgc tactaatgtg tagccaggat ggagaaaccc tgttctaaat   19860
aggtaggact tggggctaaa cccatgactt tcagctagga ggattagaat tgcccatgga   19920 gttttttctgg ctgggcacgg tggctcacgc ctataatccc agcactttgg gaggccaagg   19980
cggacggatc aggagttcaa gaccagcctg accaacatgg tgaaaccccc tctctactaa   20040
```

| | | | |
|---|---|---|---|
| aaatacaaaa | aaatcagctg | ggcatggtgg | cacgtgcctg | taattccagc | tactcagaag | 20100 |
| gctgaggcag | gagaatcgct | tgaacccggg | aggtggagat | tgcagtgagc | cgagatcgtg | 20160 |
| ccactgcact | ccagcctggg | cgacagagca | agactccgtc | tcaaaaaaaa | aaaaaaaaaa | 20220 |
| agaattgcct | gtggagtttt | tcaacatacg | taagcctata | ctttgttggc | cctgttcatt | 20280 |
| aatgggctcc | accaggaaat | taggaatcta | gttgagaaac | agaagctgaa | tggaaaggcc | 20340 |
| accttatttg | atatgttaaa | ttatatggga | agcactgtca | aatcattagt | gatgttaaac | 20400 |
| cttctctaag | ttatatttat | gagtatgtta | ttgatgtatt | ccaaaagtta | tataagaaat | 20460 |
| tctagaaatc | taattggtta | tcagccataa | tgtcatatgc | cacagaagta | actaaatttc | 20520 |
| tatgtgagtt | gtgttcttat | tataataaat | tatcatcaga | ttttaactg | tactcatttt | 20580 |
| aaatctttgt | cattcacaga | cagttgtttt | gcttcttcct | taaagcattt | gcaacagcta | 20640 |
| cagtctaaaa | ttgcttcttt | accaaggata | tttacagaaa | agactctgac | cagagatcga | 20700 |
| gaccatccta | gccaacatcg | tgaaacccca | tctctactaa | aaatacaaaa | atgagctggg | 20760 |
| cttggtggcg | cacacctgta | gtcccagtta | ctcgggaggc | tgaggcagga | gaatcgcttg | 20820 |
| aacccgggag | gtggagattg | cagtgagccc | agatcgcacc | actgcactcc | agtctggcaa | 20880 |
| cagagcaaga | ctccatctca | aaagaaaag | aaaagaagac | tctgacctgt | actcttgaat | 20940 |
| acaagtttct | gataccactg | cactgtctga | gaatttccaa | aactttaatg | aactaactga | 21000 |
| cagcttcatg | aaactgtcca | ccaagatcaa | gcagagaaaa | taattaattt | catgggacta | 21060 |
| aatgaactaa | tgaggataat | attttcataa | ttttttattt | gaattttgc | tgattctttta | 21120 |
| aatgtcttgt | ttcccagatt | tcaggaaact | tttttctt | taagctatcc | acagcttaca | 21180 |
| gcaatttgat | aaaatatact | tttgtgaaca | aaaattgaga | catttacatt | ttctccctat | 21240 |
| gtggtcgctc | cagacttggg | aaactattca | tgaatattta | tattgtatgg | taatatagtt | 21300 |
| attgcacaag | ttcaataaaa | atctgctctt | tgtatgacag | aatacatttg | aaaacattgg | 21360 |
| ttatattacc | aagactttga | ctagaatgtc | gtatttgagg | atataaaccc | ataggtaata | 21420 |
| aacccacagg | tactacaaac | aaagtctgaa | gtcagccttg | gtttggcttc | ctagtgtcaa | 21480 |
| ttaaacttct | aaaagtttaa | tctgagattc | cttataaaaa | cttccagcaa | agcaacttta | 21540 |
| aaaaagtctg | tgtgggccgg | gcgcggtggc | tcacgcctgt | aatcccagca | ctttgatccg | 21600 |
| ccgaggcggg | cggatcacga | ggtcaggaga | tccagaccat | cctggctaac | acagtgaaac | 21660 |
| cccgtctcta | ctaaaaatac | aaaaaagtt | agccgggcgt | ggtggtgggg | gcctgtagtc | 21720 |
| ccagctactc | aggaggctga | ggcaggagaa | cggcatgaac | ccgggaggca | gggcttgcag | 21780 |
| tgagccaaga | tcatgccgct | gcactccagc | ctgggagaca | aagtgagact | ccgtcaaaaa | 21840 |
| aaaaaaaa | | | | | | 21849 |

```
<210> SEQ ID NO 32
<211> LENGTH: 1869
<212> TYPE: DNA
<213> ORGANISM: Homo sapiens
<220> FEATURE:
<221> NAME/KEY: misc_feature
<222> LOCATION: (1)..(1869)
<223> OTHER INFORMATION: RNA18SN5

<400> SEQUENCE: 32
```

| | | | |
|---|---|---|---|
| tacctggttg | atcctgccag | tagcatatgc | ttgtctcaaa | gattaagcca | tgcatgtctg | 60 |
| agtacgcacg | gccggtacag | tgaaactgcg | aatggctcat | taaatcagtt | atggttcctt | 120 |

-continued

```
tggtcgctcg ctcctctcct acttggataa ctgtggtaat tctagagcta atacatgccg    180
acgggcgctg acccccttcg cggggggggat gcgtgcattt atcagatcaa aaccaacccg    240
gtcagcccct ctccggcccc ggccgggggg cgggcgccgg cggctttggt gactctagat    300
aacctcgggc cgatcgcacg cccccgtgg cggcgacgac ccattcgaac gtctgccta    360
tcaactttcg atggtagtcg ccgtgcctac catggtgacc acgggtgacg gggaatcagg    420
gttcgattcc ggagagggag cctgagaaac ggctaccaca tccaaggaag gcagcaggcg    480
cgcaaattac ccactcccga cccggggagg tagtgacgaa aaataacaat acaggactct    540
ttcgaggccc tgtaattgga atgagtccac tttaaatcct ttaacgagga tccattggag    600
ggcaagtctg gtgccagcag ccgcggtaat tccagctcca atagcgtata ttaaagttgc    660
tgcagttaaa aagctcgtag ttggatcttg ggagcgggcg ggcggtccgc cgcgaggcga    720
gccaccgccc gtccccgccc cttgcctctc ggcgccccct cgatgctctt agctgagtgt    780
cccgcgggc ccgaagcgtt tactttgaaa aaattagagt gttcaaagca ggcccgagcc    840
gcctggatac cgcagctagg aataatgaaa taggaccgcg gttctatttt gttggttttc    900
ggaactgagg ccatgattaa gagggacggc cggggggcatt cgtattgcgc cgctagaggt    960
gaaattcttg gaccggcgca agacggacca gagcgaaagc atttgccaag aatgttttca   1020
ttaatcaaga acgaaagtcg gaggttcgaa gacgatcaga taccgtcgta gttccgacca   1080
taaacgatgc cgaccggcga tgcggcggcg ttattcccat gacccgccgg gcagcttccg   1140
ggaaaccaaa gtctttgggt tccggggga gtatggttgc aaagctgaaa cttaaaggaa   1200
ttgacgaag ggcaccacca ggagtggagc ctgcggctta atttgactca acacgggaaa   1260
cctcacccgg cccggacacg gacaggattg acagattgat agctctttct cgattccgtg   1320
ggtggtggtg catggccgtt cttagttggt ggagcgattt gtctggttaa ttccgataac   1380
gaacgagact ctggcatgct aactagttac gcgacccccg agcggtcggc gtcccccaac   1440
ttcttagagg gacaagtggc gttcagccac ccgagattga gcaataacag gtctgtgatg   1500
cccttagatg tccggggctg cacgcgcgct acactgactg gctcagcgtg tgcctaccct   1560
acgccggcag gcgcgggtaa cccgttgaac cccattcgtg atggggatcg gggattgcaa   1620
ttattcccca tgaacgagga attcccagta agtgcgggtc ataagcttgc gttgattaag   1680
tccctgccct ttgtacacac cgcccgtcgc tactaccgat tggatggttt agtgaggccc   1740
tcggatcggc cccgccgggg tcggcccacg gccctggcgg agcgctgaga agacggtcga   1800
acttgactat ctagaggaag taaaagtcgt aacaaggttt ccgtaggtga acctgcggaa   1860
ggatcatta                                                         1869
```